United States Patent
Inukai et al.

(10) Patent No.: US 9,586,967 B2
(45) Date of Patent: Mar. 7, 2017

(54) PYRROLO PYRIMIDINE DERIVATIVE

(71) Applicant: ONO PHARMACEUTICAL CO., LTD., Osaka (JP)

(72) Inventors: Takayuki Inukai, Osaka (JP); Jun Takeuchi, Osaka (JP); Tomoko Yasuhiro, Osaka (JP); Mark Allan Wolf, Williamsville, NY (US); Vijay Dattaram Pawar, Choa Chu Kang (SG); Anjan Chakrabarti, Dover (SG); Santhosh Kumar Chittimalla, Clementi (SG)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/034,905

(22) PCT Filed: Nov. 6, 2014

(86) PCT No.: PCT/JP2014/079461
§ 371 (c)(1),
(2) Date: May 6, 2016

(87) PCT Pub. No.: WO2015/068767
PCT Pub. Date: May 14, 2015

(65) Prior Publication Data
US 2016/0264579 A1    Sep. 15, 2016

(30) Foreign Application Priority Data

Nov. 8, 2013 (JP) .................................. 2013-231797

(51) Int. Cl.
C07D 487/04    (2006.01)

(52) U.S. Cl.
CPC .................................. *C07D 487/04* (2013.01)

(58) Field of Classification Search
None
See application file for complete search history.

(56) References Cited

U.S. PATENT DOCUMENTS

| | | |
|---|---|---|
| 2008/0293733 A1 | 11/2008 | Bearss et al. |
| 2010/0144730 A1 | 6/2010 | Lind et al. |
| 2011/0269958 A1 | 11/2011 | Engelhardt et al. |
| 2013/0137708 A1 | 5/2013 | Garske et al. |
| 2013/0281428 A1 | 10/2013 | Ohki et al. |

FOREIGN PATENT DOCUMENTS

| | | |
|---|---|---|
| JP | 2009-542684 A | 12/2009 |
| JP | 2010-523712 A | 7/2010 |
| JP | 2011-528026 A | 11/2011 |
| WO | 00/17202 A1 | 3/2000 |
| WO | 00/17203 A1 | 3/2000 |
| WO | 01/72751 A1 | 10/2001 |
| WO | 2011/153553 A2 | 12/2011 |
| WO | 2011/153553 A3 | 12/2011 |
| WO | 2013/115280 A1 | 8/2013 |

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002.*
Rouhi, "The Right Stuff, from research and development to the clinic, getting drug crystals right is full of pitfalls", Chemical & Engineering News, Feb. 24, 2003, pp. 32-35.*
Ullmann's Encyclopedia of Industrial Chemistry, Copyright © 2002 by Wiley-VCH Verlag GmbH & Co. KGaA , pp. 1-51.*
The Organic Chemistry of Drug Design and Drug Action, Silverman, Academic Press, 1992, pp. 352-355, see pp. 354-355.*
Rosa M. Suarez et al, "Inhibitors of the TAM subfamily of tyrosine kinases: Synthesis and biological evaluation", European Journal of Medicinal Chemistry, 2013, 61, pp. 2-25.
Vyacheslav A. Korshunov, "Axl-dependent signalling: a clinical update", Clinical Science (2012) 122, pp. 361-368.
Christine Gjerdruma, et al., "Axl is an essential epithelial-to-mesenchymal transition-induced regulator of breast cancer metastasis and patient survival", Proceedings of the national academy of sciences of the United States of America, vol. 107, No. 3, Jan. 19, 2010, pp. 1124-1129.
Il-Kyoo Park, et al., "Inhibition of the receptor tyrosine kinase Axl impedes activation of the FLT3 internal tandem duplication in human acute myeloid leukemia: implications for Axl as a potential therapeutic target", Myeloid Neoplasia, Blood, Mar. 14, 2013, vol. 121, No. 11, at http://www.bloodjournal.org/content/121/11/2064?sso-checked=true, total 11 pages.

* cited by examiner

Primary Examiner — Karl J Puttlitz
(74) Attorney, Agent, or Firm — Sughrue Mion, PLLC

(57) ABSTRACT

A compound represented by the general formula (1) has a pyridone ring structure introduced into a pyrrolo pyrimidine skeleton, so that the compound has a strong Axl inhibitory activity. Consequently, the compound can be used as a therapeutic agent for Axl-related diseases including cancers such as acute myeloid leukemia, melanoma, breast cancer, pancreatic cancer, and glioma, kidney diseases, immune system diseases, and circulatory system diseases.

7 Claims, No Drawings

PYRROLO PYRIMIDINE DERIVATIVE

TECHNICAL FIELD

The present invention relates to a compound represented by the general formula (I):

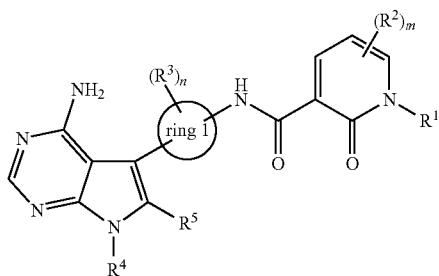

(wherein all of the symbols have the same meanings as given below), a salt thereof, a solvate thereof, an N-oxide thereof, or a prodrug thereof (hereinafter, also abbreviated as the compound of the present invention).

BACKGROUND ART

Axl (also known as: UFO, ARK, Tyro7) is a receptor tyrosine kinase belonging to a TAM family (Axl, Mer and Tyro3) cloned from tumor cells. Gas6 (growth-arrest-specific protein 6) gene specifically expressed at the time of cell proliferation arrest has been cloned. The expressed protein is known as a ligand for Axl. Axl activated by binding of Gas6 transfers a signal via phosphorylation. Since the signal activates an Erk1/2 pathway or a PI3K/Akt pathway, the activation of Axl is known to be involved in pathologic conditions of cancers, immune system diseases, circulatory system diseases, and the like (see, Non-Patent Literature 1).

In particular, the relation between Axl and various types of cancers is well known. For example, it is known that the expression of Axl is involved in metastasis and prognosis of breast cancer (see, Non-Patent Literature 2), and that Axl is involved in the pathologic conditions of acute myeloid leukemia (AML) (see Non-Patent Literature 3). Therefore, it is considered that compounds which inhibit the activation of Axl are useful for treatment of various types of cancers, immune system diseases, and circulatory system diseases.

By the way, as prior art of the compound of the present invention, a compound represented by the general formula (A):

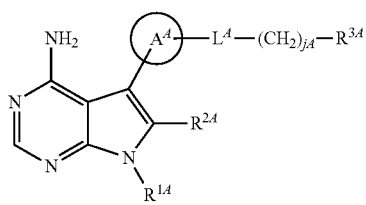

(wherein $A^A$ represents a 6-membered aromatic ring or a 5- to 6-membered heteroaromatic ring, which may have a substituent such as halogen; $L^A$ represents —O—, —S—, —N(C(O)R$^4$)—, or the like; $R^4$ represents hydrogen, an acyl group, or the like; $R^{1A}$ represents hydrogen, a C1-C6 alkyl group, or the like; $R^{2A}$ represents hydrogen, a substituted or unsubstituted aliphatic compound, or the like; $R^{3A}$ represents a substituted or unsubstituted cycloalkyl group, a substituted or unsubstituted aromatic ring, or the like; and jA represents an integer from 0 to 6 (where the definitions of the groups are excerpted)) is known to be a VEGF kinase inhibitor (see Patent Literatures 1, 2, and 3).

Furthermore, a compound represented by the general formula (B):

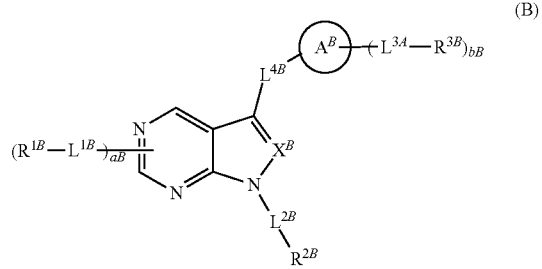

(wherein $X^B$ represents =N— or =C(-L$^{6B}$-R$^{6B}$)—; $L^{1B}$, $L^{2B}$, $L^{3B}$, $L^{4B}$, and $L^{6B}$ independently represent a bond, —C(O)—N(R$^{7B}$)—, a substituted or unsubstituted alkylene group, or the like; $R^{1B}$, $R^{2B}$, $R^{3B}$, $R^{6B}$, and $R^{7B}$ independently represent hydrogen, halogen, —NH$_2$, a substituted or unsubstituted alkyl group, a substituted or unsubstituted cycloalkyl group, a substituted or unsubstituted heterocycloalkyl group, or the like; aB represents an integer from 0 to 2; and bB represents an integer from 0 to 5 (where the definitions of the groups are excerpted)) is known to be a Lrrk-2 inhibitor (see Patent Literature 4).

A compound having pyrrolo pyrimidine derivative having a pyridone ring, represented by the following structural formula:

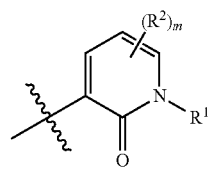

is a compound of the present invention. Any of the prior art literatures neither mention nor suggest that the compound of the present invention has significant Axl inhibitory activity.

PRIOR ART LITERATURES

Patent Literatures

[Patent Literature 1] WO2000/017202
[Patent Literature 2] WO2000/017203
[Patent Literature 3] WO2001/072751
[Patent Literature 4] WO2011/153553

Non-Patent Literatures

[Non-Patent Literature 1] Clinical Science, Vol. 122, p. 361-368, 2012
[Non-Patent Literature 2] Proceedings of the national academy of sciences of the United States of America, Vol. 107, No. 3, p. 1124-1129, 2010

[Non-Patent Literature 3] Blood, Vol. 121, p. 2064-2073, 2013

SUMMARY OF INVENTION

Technical Problem

A problem to be solved by the present invention is to find a compound having Axl inhibitory activity, which is useful for treatment of cancers such as AML, and to provide the compound as pharmaceuticals.

Solution to Problem

In order to solve the above-mentioned problems, the inventors of the present invention have keenly studied to find a compound strongly inhibiting Axl. As a result, surprisingly, the inventors have found that a pyridone ring represented by the following structural formula:

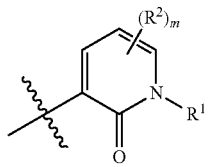

improves the Axl inhibitory activity, and the inventors have completed the present invention.

That is to say, the present invention relates to:
[1] a compound represented by the general formula (1)

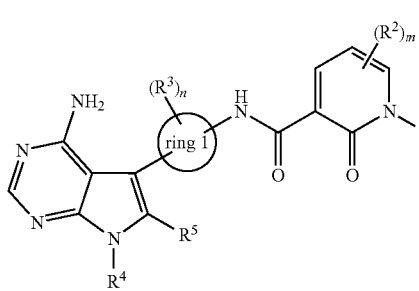

(I)

[wherein $R^1$ represents (1) a C1-8 alkyl group optionally substituted with one to five $R^{11}$, (2) a C3-7 carbon ring optionally substituted with one to five $R^{12}$, or (3) a 4- to 7-membered heterocycle optionally substituted with one to five $R^{13}$, wherein when the C1-8 alkyl group represented by $R^1$ is a branched alkyl group, the C1-3 alkyl groups branched from the same carbon atom together optionally form a saturated C3-7 carbon ring,
$R^2$ represents (1) a C1-8 alkyl group optionally substituted with one to five $R^{21}$, (2) a C2-8 alkenyl group optionally substituted with one to five $R^{22}$, (3) a C2-8 alkynyl group optionally substituted with one to five $R^{23}$, (4) an —$OR^{24}$ group, (5) a C3-7 carbocyclic ring optionally substituted with one to five $R^{25}$, (6) 4- to 7-membered heterocycle optionally substituted with one to five $R^{26}$, (7) a halogen atom, (8) a C(O)$R^{27}$ group, or (9) a C(O)NR$^{28}$R$^{29}$ group, wherein, when m is 2 or more, $R^2$s are on neighboring carbon atoms, and each $R^2$ represents a C1-3 alkyl group optionally substituted with an amino group or a C2-3 alkenyl group optionally substituted with an amino group, $R^2$s bonded to the neighboring carbon atoms together with the carbon atoms may form a 5- to 7-membered cyclic group optionally substituted with one to three $R^{20}$,
$R^3$ represents (1) a C1-4 alkyl group, (2) a halogen atom, (3) a C1-4 haloalkyl group, or (4) an —$OR^{31}$ group,
$R^4$ represents (1) a hydrogen atom, (2) a C1-8 alkyl group optionally substituted with one to five $R^{41}$, (3) a C3-10 carbocyclic ring optionally substituted with one to five $R^{42}$, or (4) a 4- to 10-membered heterocycle optionally substituted with one to five $R^{43}$,
$R^5$ represents (1) a hydrogen atom, (2) a C1-4 alkyl group, (3) a halogen atom, or (4) a C1-4 haloalkyl group,
$R^{11}$ represents (1) an —$OR^{101}$ group, (2) an $SO_2R^{102}$ group, (3) an NR$^{103}$R$^{104}$ group, or (4) a C3-7 carbon ring optionally substituted with one to three halogen atoms,
$R^{12}$ represents (1) a C1-4 alkyl group optionally substituted with an amino group, or (2) a C1-4 haloalkyl group, and (3) a halogen atom,
$R^{13}$ represents (1) a C1-4 alkyl group optionally substituted with an amino group, or (2) a C1-4 haloalkyl group, and (3) a halogen atom,
$R^{101}$ represents (1) a hydrogen atom, or (2) a C1-4 alkyl group,
$R^{102}$ represents (1) a hydrogen atom, or (2) a C1-4 alkyl group,
$R^{103}$ and $R^{104}$ each independently represents (1) a hydrogen atom, or (2) a C1-4 alkyl group,
$R^{20}$ represents (1) a C1-4 alkyl group, (2) a halogen atom, (3) a C1-4 haloalkyl group, (4) an oxo group, (5) an —$OR^{201}$ group, or (6) a COOR$^{205}$ group, wherein when two $R^{20}$s represent a C1-3 alkyl group and are on the same carbon atom, the $R^{20}$s together may form a C3-7 saturated carbon ring,
$R^{21}$, $R^{22}$, and $R^{23}$ each independently represents (1) a hydrogen atom, (2) —$OR^{202}$, or (3) NR$^{203}$R$^{204}$,
$R^{24}$ represents (1) a hydrogen atom, (2) a C1-4 alkyl group, or (3) 4- to 10-membered heterocycle,
$R^{25}$ and $R^{26}$ each independently represents (1) a C1-4 alkyl group, or (2) a halogen atom,
$R^{27}$ represents (1) a hydrogen atom, (2) a C1-4 alkyl group, or (3) a C3-7 carbocyclic ring,
$R^{28}$ and $R^{29}$ each independently represents (1) a hydrogen atom, (2) a C1-4 alkyl group, or (3) a C3-7 carbocyclic ring,
$R^{201}$ represents (1) a hydrogen atom, or (2) a C1-4 alkyl group,
$R^{202}$ represents (1) a hydrogen atom, or (2) a C1-4 alkyl group,
$R^{203}$ and $R^{204}$ each independently represents (1) a hydrogen atom, (2) a C1-4 alkyl group, or (3) a C(O)$R^{210}$ group,
$R^{205}$ represents (1) a hydrogen atom, or (2) a C1-4 alkyl group,
$R^{210}$ represents (1) a C1-4 alkyl group optionally substituted with NR$^{211}$R$^{212}$ or a cyano group, (2) a C2-4 alkenyl group optionally substituted with NR$^{213}$R$^{214}$ or a cyano group, or (3) a C2-4 alkynyl group optionally substituted with NR$^{215}$R$^{216}$ or a cyano group,
$R^{211}$, $R^{212}$, $R^{213}$, $R^{214}$, $R^{215}$, and $R^{216}$ each independently represents (1) a hydrogen atom, or (2) a C1-4 alkyl group,
$R^{31}$ represents (1) a hydrogen atom, (2) a C1-4 alkyl group, or (3) a C1-4 haloalkyl group,
$R^{41}$ represents (1) an —$OR^{401}$ group, (2) an $SO_2R^{402}$ group, (3) an NR$^{403}$R$^{404}$ group, or (4) 5- to 7-membered cyclic group optionally substituted with one to three $R^{405}$,
$R^{42}$ represents (1) a C1-4 alkyl group optionally substituted with a hydroxyl group or an NR$^{406}$R$^{407}$ group, (2) a halogen atom, (3) a hydroxyl group, or (4) an oxo group, $R^{43}$ represents (1) a C1-4 alkyl group optionally substituted with a hydroxyl group or an $NR^{408}R^{409}$ group, (2) a halogen atom, (3) a hydroxyl group, or (4) an oxo group, $R^{401}$ represents (1) a hydrogen atom, or (2) a C1-4 alkyl group, $R^{402}$ represents (1) a hydrogen atom, or (2) a C1-4 alkyl group, $R^{403}$ and $R^{404}$ each independently represents (1) a hydrogen atom, or (2) a C1-4 alkyl group, $R^{405}$ represents (1) a halogen atom, (2) a hydroxyl group, (3) an amino group, or (4) a C1-4 alkyl group, $R^{406}$, $R^{407}$, $R^{408}$, and $R^{409}$ each independently represents (1) a hydrogen atom, or (2) a C1-4 alkyl group, ring1 represents a 5- to 7-membered cyclic group, when a plurality of $R^{11}$, $R^{12}$, $R^{13}$, $R^{20}$, $R^{21}$, $R^{22}$, $R^{23}$, $R^{25}$, $R^{26}$, $R^{41}$, $R^{42}$, or $R^{405}$ is present, any of them may be the same as or different from each other, m is an integer from 0 to 3, n is an integer from 0 to 3, when m is 2 or more, a plurality of $R^2$s may be the same as or different from each other, when n is 2 or more, a plurality of $R^3$s may be the same as or different from each other], a salt thereof, a solvate thereof, an N-oxide thereof, or a prodrug thereof,

[2] the compound according to the above-mentioned [1], wherein the ring1 is benzene or pyridine,

[3] the compound according to the above-mentioned [1], which is represented by the general formula (I-1)

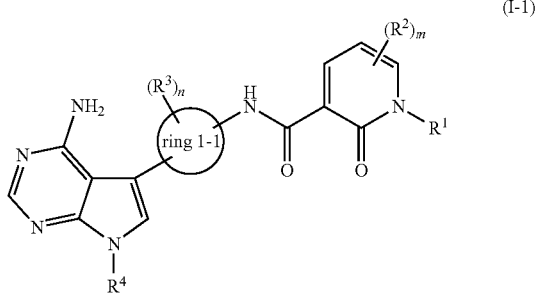

(I-1)

[wherein ring 1-1 represents benzene or pyridine, and the other reference marks mean the same as those in the above-mentioned [1]],

[4] the compound according to the above-mentioned [1] to [3], which is (1) N-[5-(4-amino-7-methyl-7H-pyrrolo[2,3-d]pyrimidin-5-yl)-2-pyridinyl]-2',5'-dioxo-1'-phenyl-2',5',6',8'-tetrahydro-1'H-spiro[cyclopropane-1,7'-quinoline]-3'-carboxamide, (2) N-[4-(4-amino-7-methyl-7H-pyrrolo[2,3-d]pyrimidin-5-yl)phenyl]-2-oxo-1-phenyl-5-(trifluoromethyl)-1,2-dihydro-3-pyridinecarboxamide, (3) N-[4-(4-amino-7-methyl-7H-pyrrolo[2,3-d]pyrimidin-5-yl) phenyl]-6-[(2-butynoylamino)methyl]-2-oxo-1-phenyl-1,2-dihydro-3-pyridinecarboxamide, (4) N-[4-(4-amino-7-methyl-7H-pyrrolo[2,3-d]pyrimidin-5-yl)phenyl]-2,5-dioxo-1-phenyl-1,2,5,6,7,8-hexahydro-3-quinolinecarboxamide, (5) N-[4-(4-amino-7-cyclopentyl-7H-pyrrolo[2,3-d]pyrimidin-5-yl)phenyl]-2-oxo-1-phenyl-1,2-dihydro-3-pyridinecarboxamide, (6) N-{4-[4-amino-7-(2-hydroxy-2-methylpropyl)-7H-pyrrolo[2,3-d]pyrimidin-5-yl]phenyl}-2,5-dioxo-1-phenyl-1,2,5,6,7,8-hexahydro-3-quinolinecarboxamide, (7) N-[4-(4-amino-7-methyl-7H-pyrrolo[2,3-d]pyrimidin-5-yl)phenyl]-2-oxo-1-phenyl-1,2-dihydro-3-quinolinecarboxamide, (8) N-[4-{4-amino-7-[cis-3-(hydroxymethyl)cyclobutyl]-7H-pyrrolo[2,3-d]pyrimidin-5-yl}phenyl)-2,5-dioxo-1-phenyl-1,2,5,6,7,8-hexahydro-3-quinolinecarboxamide, (9) N-[5-(4-amino-7-methyl-7H-pyrrolo[2,3-d]pyrimidin-5-yl)-2-pyridinyl]-2,5-dioxo-1-phenyl-1,2,5,6,7,8-hexahydro-3-quinolinecarboxamide, (10) N-[4-(4-amino-7-methyl-7H-pyrrolo[2,3-d]pyrimidin-5-yl)phenyl]-1-[(1R)-2-hydroxy-1-phenylethyl]-2-oxo-1,2-dihydro-3-pyridinecarboxamide, (11) N-[4-(4-amino-7-cyclopentyl-7H-pyrrolo[2,3-d]pyrimidin-5-yl)phenyl]-4-ethoxy-1-(4-fluorophenyl)-2-oxo-1,2-dihydro-3-pyridinecarboxamide, (12) N-[4-(4-amino-7-methyl-7H-pyrrolo[2,3-d]pyrimidin-5-yl)phenyl]-5-cyclopropyl-2-oxo-1-phenyl-1,2-dihydro-3-pyridinecarboxamide, (13) N-[4-(4-amino-7-methyl-7H-pyrrolo[2,3-d]pyrimidin-5-yl)phenyl]-7-(2-butynoyl)-2-oxo-1-phenyl-1,2,5,6,7,8-hexahydro-1,7-naphthyridine-3-carboxamide, or (14) N-{4-[4-amino-7-methyl-6-(trifluoromethyl)-7H-pyrrolo[2,3-d]pyrimidin-5-yl]phenyl}-2,5-dioxo-1-phenyl-1,2,5,6,7,8-hexahydro-3-quinolinecarboxamide,

[5] a pharmaceutical composition containing the compound represented by the general formula (I) as defined in the above-mentioned [1], a salt thereof, a solvate thereof, an N-oxide thereof, or a prodrug thereof,

[6] the pharmaceutical composition according to the above-mentioned [5], which is an Axl inhibitor,

[7] the pharmaceutical composition according to the above-mentioned [6], which is an agent for preventing and/or treating an Axl-related disease,

[8] the pharmaceutical composition according to the above-mentioned [7], wherein the Axl-related disease includes cancers, kidney diseases, immune system diseases, or circulatory system diseases,

[9] the pharmaceutical composition according to the above-mentioned [8], wherein the cancer is acute myeloid leukemia, melanoma, breast cancer, pancreatic cancer, or glioma,

[10] the pharmaceutical composition according to the above-mentioned [5], which is a metastasis suppressing agent for tumor cells,

[11] a method for preventing and/or treating an Axl-related disease, or suppressing metastasis of tumor cells, the method including administering an effective amount of the compound represented by the general formula (I) as defined in the above-mentioned [1], a salt thereof, a solvate thereof, an N-oxide thereof, or a prodrug thereof, to a mammal,

[12] the compound represented by the general formula (I) according to the above-mentioned [1], a salt thereof, a solvate thereof, an N-oxide thereof, or a prodrug, for preventing and/or treating an Axl-related disease, or for suppressing metastasis of tumor cells, and

[13] use of a compound represented by the general formula (I), a salt thereof, a solvate thereof, an N-oxide thereof, or a prodrug, as defined in the above-mentioned [1], to manufacture an agent for preventing and/or treating an Axl-related disease, or for suppressing metastasis of tumor cells.

Effects of Invention

A compound of the present invention has strong Axl inhibitory activity, and Axl selective inhibitory activity, and therefore is useful for treatment of acute myeloid leukemia or the like.

DESCRIPTION OF EMBODIMENTS

The present invention will be described in detail hereinafter.

In the present invention, a halogen atom denotes a fluorine atom, a chlorine atom, a bromine atom, and an iodine atom.

In the present invention, the C1-8 alkyl group includes a straight or branched C1-8 alkyl group. Examples thereof include methyl, ethyl, propyl, butyl, pentyl, hexyl, heptyl, octyl, isopropyl, isobutyl, sec-butyl, tert-butyl, and an isomer thereof.

In the present invention, the C1-4 alkyl group includes a straight or branched C1-4 alkyl group. Examples thereof include methyl, ethyl, propyl, butyl, isopropyl, isobutyl, sec-butyl, and tert-butyl.

In the present invention, the C1-3 alkyl group includes a straight or branched C1-3 alkyl group. Examples thereof include a methyl group, an ethyl group, a propyl group, and an isopropyl.

In the present invention, the C1-4 haloalkyl group denotes, for example, a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, and a 4-bromobutyl group.

In the present invention, the C2-8 alkenyl group includes a straight or branched C2-8 alkenyl group. Examples thereof include ethenyl, propenyl, butenyl, pentenyl, hexenyl, heptenyl, and octenyl, and an isomer thereof.

In the present invention, the C2-4 alkenyl group includes a straight or branched C2-4 alkenyl group. Examples thereof include ethenyl, propenyl, butenyl, and an isomer thereof.

In the present invention, the C2-3 alkenyl group includes a straight or branched C2-3 alkenyl group. Examples thereof include ethenyl, propenyl, and an isomer thereof.

In the present invention, the C2-8 alkynyl group includes a straight or branched C2-8 alkynyl group. Examples thereof include ethynyl, propynyl, butynyl, pentynyl, hexynyl, heptynyl, octynyl, and an isomer thereof.

In the present invention, the C2-4 alkynyl group includes a straight or branched C2-4 alkynyl group. Examples thereof include ethynyl, propynyl, butynyl, and an isomer thereof.

In the present invention, the C3-7 carbon ring denotes a C3-7 monocyclic carbon ring, and a carbon ring which may be partially or completely saturated, and examples thereof include cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene, or benzene ring.

In the present invention, the C5-7 carbon ring denotes a C5-7 monocyclic carbon ring, and a carbon ring which may be partially or completely saturated, and examples thereof include cyclopentane, cyclohexane, cycloheptane, cyclopentene, cyclohexene, cycloheptene, cyclopentadiene, cyclohexadiene, cycloheptadiene, or benzene ring.

In the present invention, examples of the saturated C3-7 carbon ring include cyclopropane, cyclobutane, cyclopentane, cyclohexane, and cycloheptane.

In the present invention, examples of the saturated C5-7 carbon ring include cyclopentane, cyclohexane, and cycloheptane.

In the present invention, the 4- to 10-membered heterocycle denotes 4- to 10-membered monocyclic or bicyclic heterocycle, which includes one to five heteroatoms selected from an oxygen atom, a nitrogen atom and a sulfur atom, and a part or all of which is saturated. Example thereof include azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetan, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepin, indole, isoindole, indolizine, benzofuran, iso benzofuran, benzothiophene, isobenzothiophene, indazole, purine, benzoxazole, benzothiazole, benzimidazole, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydrobenzoxazole, perhydrobenzoxazole, dihydrobenzothiazole, perhydrobenzothiazole, dihydrobenzimidazole, perhydrobenzimidazole, dioxaindan, benzodithiolane, dithianaphthalene, quinoline, isoquinoline, quinolizine, phthalazine, pteridine, naphthyridine, quinoxaline, quinazoline, cinnoline, chromene, dihydroquinoline, tetrahydroquino line, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathian, dihydrobenzoxazine, dihydrobenzothiazine, pyrazinomorpholine, benzodioxan, chroman, or benzodithiane ring.

In the present invention, the 4- to 7-membered heterocycle denotes 4- to 7-membered monocyclic heterocycle, which includes one to five heteroatoms selected from an oxygen atom, a nitrogen atom and a sulfur atom, and a part or all of which is saturated. Example thereof include azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetan, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, or thiadiazepin ring.

In the present invention, the 5- to 7-membered cyclic group denotes C5-7 carbon ring and 5- to 7-membered heterocycle. Herein, the C5-7 carbon ring has the same meaning as defined above, the 5- to 7-membered heterocycle includes 5- to 7-membered unsaturated heterocycle and 5- to 7-membered saturated heterocycle. Examples of 5- to 7-membered heterocycle include pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, dihydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole, (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, or thiadiazepin ring.

In the present invention, "when the C1-8 alkyl group represented by $R^1$ is a branched alkyl group, the C1-3 alkyl group branched from the same carbon atom optionally may form a saturated C3-7 carbon ring together" denotes that in a partial structure of the following general formula (I):

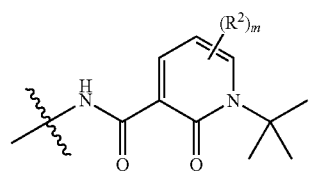

(wherein all of the symbols have the same meanings as defined above), for example, when $R^1$ is a branched alkyl chain as represented in the above-mentioned general formula, the alkyl chain branched from the same carbon atom, together with the carbon atom bound thereto, forms a saturated carbon ring, as shown in the following general formula:

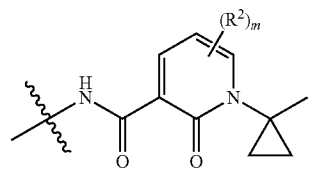

(wherein all of the symbols have the same meanings as defined above).

In the present invention, "when $R^2$s are on the neighboring carbon atoms, and $R^2$ represents a C1-3 alkyl group optionally substituted with an amino group or a C2-3 alkenyl group optionally substituted with an amino group, the $R^2$s bonded to the neighboring carbon atoms together with the carbon atoms may form a 5- to 7-membered cyclic group optionally substituted with one to three $R^{20}$s" denotes that in a partial structure of the following general formula (I):

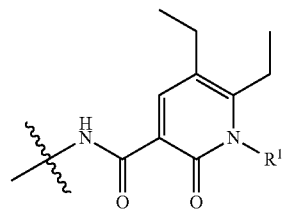

(wherein all of the symbols have the same meanings as defined above), for example, when a plurality of $R^2$s is an alkyl group as represented in the above-mentioned general formula, the $R^2$ together with a carbon atom neighboring thereto forms, as shown in the following general formula:

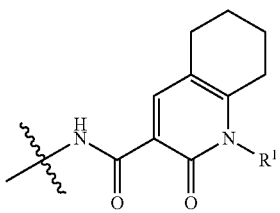

(wherein all of the symbols have the same meanings as defined above), a 5- to 7-membered cyclic group such as a cyclohexane ring.

In the present invention, it is preferable that $R^1$ is a C1-8 alkyl group optionally substituted with one to five $R^{11}$, or a C3-7 carbon ring optionally substituted with one to five $R^{12}$.

In the present invention, ring1 is preferably benzene or pyridine.

In the present invention, it is preferable that the compound represented by the general formula (I) is a compound represented by the general formula (I-1):

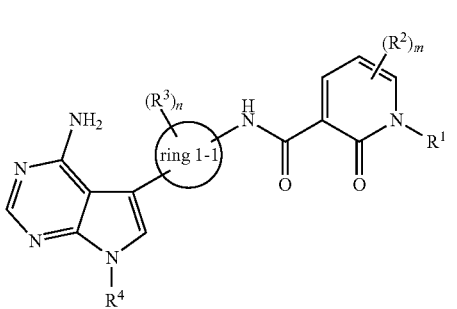

(wherein all of the symbols have the same meanings as defined above).

In the present invention, it is preferable that two binding arms in the ring1 and ring1-1 are bound to a para position.

In the present invention, as the preferable compound, the compounds described in Examples are preferable. More preferable compounds include: (1) N-[5-(4-amino-7-methyl-7H-pyrrolo[2,3-d]pyrimidin-5-yl)-2-pyridinyl]-2',5'-dioxo-1'-phenyl-2',5',6',8'-tetrahydro-1'H-spiro[cyclopropane-1,7'-quinoline]-3'-carboxamide, (2) N-[4-(4-amino-7-methyl-7H-pyrrolo[2,3-d]pyrimidin-5-yl)phenyl]-2-oxo-1-phenyl-5-(trifluoromethyl)-1,2-dihydro-3-pyridinecarboxamide, (3) N-[4-(4-amino-7-methyl-7H-pyrrolo[2,3-d]pyrimidin-5-yl)phenyl]-6-[(2-butynoylamino)methyl]-2-oxo-1-phenyl-1,2-dihydro-3-pyridinecarboxamide, (4) N-[4-(4-amino-7-methyl-7H-pyrrolo[2,3-d]pyrimidin-5-yl)phenyl]-2,5-dioxo-1-phenyl-1,2,5,6,7,8-hexahydro-3-quinolinecarboxamide, (5) N-[4-(4-amino-7-cyclopentyl-7H-pyrrolo[2,3-d]pyrimidin-5-yl)phenyl]-2-oxo-1-phenyl-1,2-dihydro-3-pyridinecarboxamide, (6) N-{4-[4-amino-7-(2-hydroxy-2-methylpropyl)-7H-pyrrolo[2,3-d]pyrimidin-5-yl]phenyl}-2,5-dioxo-1-phenyl-1,2,5,6,7,8-hexahydro-3-quinolinecarboxamide, (7) N-[4-(4-amino-7-methyl-7H-pyrrolo[2,3-d]pyrimidin-5-yl)phenyl]-2-oxo-1-phenyl-1,2-dihydro-3-quinolinecarboxamide, (8) N-[4-{4-amino-7-[cis-3-(hydroxymethyl)cyclobutyl]-7H-pyrrolo[2,3-d]pyrimidin-5-yl}phenyl]-2,5-dioxo-1-phenyl-1,2,5,6,7,8-hexahydro-3-quinolinecarboxamide, (9) N-[5-(4-amino-7-methyl-7H-pyrrolo[2,3-d]pyrimidin-5-yl)-2-pyridinyl]-2,5-dioxo-1-phenyl-1,2,5,6,7,8-hexahydro-3-quinolinecarboxamide, (10) N-[4-(4-amino-7-methyl-7H-pyrrolo[2,3-d]pyrimidin-5-yl)phenyl]-1-[(1R)-2-hydroxy-1-phenylethyl]-2-oxo-1,2-dihydro-3-pyridinecarboxamide, (11) N-[4-(4-amino-7-cyclopentyl-7H-pyrrolo[2,3-d]pyrimidin-5-yl)phenyl]-4-ethoxy-1-(4-fluorophenyl)-2-oxo-1,2-dihydro-3-pyridinecarboxamide, (12) N-[4-(4-amino-7-methyl-7H-pyrrolo[2,3-d]pyrimidin-5-yl)phenyl]-5-cyclopropyl-2-oxo-1-phenyl-1,2-dihydro-3-pyridinecarboxamide, (13) N-[4-(4-amino-7-methyl-7H-pyrrolo[2,3-d]pyrimidin-5-yl)phenyl]-7-(2-butynoyl)-2-oxo-1-phenyl-1,2,5,6,7,8-hexahydro-1,7-naphthyridine-3-carboxamide, or (14) N-{4-[4-amino-7-methyl-6-(trifluoromethyl)-7H-pyrrolo[2,3-d]pyrimidin-5-yl]phenyl}-2,5-dioxo-1-phenyl-1,2,5,6,7,8-hexahydro-3-quinolinecarboxamide.

[Isomer]

In the present invention, unless specifically directed, all of the isomers are included. For example, an alkyl group includes straight chain and branched chain groups. In addition, all of geometrical isomers of double bonds, rings, and fused rings (E-, Z-, cis-, trans-isomers), optical isomers by the presence of an asymmetric carbon atom (R-, S-isomer, α-, β-configurations, enantiomers, diastereomers), optical active isomers having optical rotation property (D, L, d, l-isomers), polar isomers according to chromatographic separation (more polar isomer, less polar isomer), equilibrium compound, rotamers, mixtures thereof at any rate, and racemic mixtures are included in the present invention. Furthermore, the present invention also encompasses all isomers by tautomers.

Furthermore, the optical isomer of the present invention is not only limited to an optical isomer having purity of 100%, but also may include other optical isomers having purity of less than 50%.

In the present invention, unless otherwise noted, as apparent to a person skilled in the art, a symbol:

represents binding toward the back side of the plane of the paper (that is to say, the α-configuration),

represents binding toward the front side of the plane of the paper (that is to say, the β-configuration), and

represents α-configuration, β-configuration or an arbitrary mixture thereof.

The compound represented by the general formula (I) is converted into the corresponding salt by the well-known method. A salt is preferably a water-soluble salt. Examples of a suitable salt include salts of an alkali metal (potassium, sodium, and the like), salts of an alkaline earth metal (calcium, magnesium, and the like), ammonium salts, or salts of a pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, and the like), acid addition salts (inorganic acid salts (hydrochloride, hydrobromide, hydroiodide, sulfate, phosphate, nitrate, and the like), organic acid salts (acetate, trifluoro acetate, lactate, tartrate, oxalate, fumarate, maleate, benzoate, citrate, methanesulfonate, ethanesulfonate, benzenesulfonate, toluenesulfonate, isethionate, glucuronate, gluconate, and the like).

The compound represented by the general formula (I) and a salt thereof can be also converted into a solvate. It is preferable that the solvate is low-toxic and water-soluble. Examples of a suitable solvate include solvates with water, or an alcoholic solvent (for example, ethanol).

The N-oxide of the compound represented by the general formula (I) denotes compounds represented by the general formula (I) in which a nitrogen atom is oxidized. Furthermore, the N-oxide of the compound represented by the general formula (I) may be salts of alkali (earth) metal salt, ammonium salt, organic amine salt, and acid addition salt mentioned above.

The prodrug of the compound represented by the general formula (I) denotes a compound which is converted to the compound represented by the general formula (I) by a reaction with an enzyme, stomach acid, and the like, in a living body. Prodrugs of the compound represented by the general formula (I) include: compounds in which the hydroxyl group is acylated, alkylated, phosphorylated, or borated, when the compounds represented by the general formula (I) have a hydroxyl group (for example, the compounds represented by the general formula (I) in which the hydroxyl group is acetylated, palmitoylated, propanoylated, pivaloylated, succinylated, fumarylated, alanylated, or dimethylaminomethylcarbonylated); and compounds in which the carboxyl group is esterified or amidated (for example, compounds represented by the general formula (I) in which the carboxyl group is made into ethyl ester, isopropyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide, and the like). These compounds can be produced by well-known methods. Furthermore, the prodrug of the compound represented by the general formula (I) may be hydrate or non-hydrate. Furthermore, the prodrug of the compound represented by the general formula (I) may be a compound which is changed into the compound represented by the general formula (I) under the physiological condition, as described in "Development of Medicaments", vol. 7 "Molecular Design", p. 163-198, published by Hirokawa Shoten in 1990. In addition, the compound represented by the general formula (I) may be labeled with an isotope thereof (for example, $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, and the like).

[Process for Producing Compound of the Present Invention]

The compound of the present invention can be produced by the well-known methods, for example, the method described in Comprehensive Organic Transformations: A Guide to Functional Group Preparations, 2nd Edition (Richard C. Larock, John Wiley & Sons Inc, 1999), or methods described in Examples, or the like, with appropriate modification and in combination thereof.

In general formula (I), a compound where $R^5$ is a hydrogen atom, m is 2 or more, $R^2$s are on the neighboring carbon atoms and represent a C1-3 alkyl group, and the $R^2$ together with the carbon atoms neighboring thereto forms a C5-7 saturated carbon ring substituted with an oxo group, that is, a compound represented by the general formula (I-a):

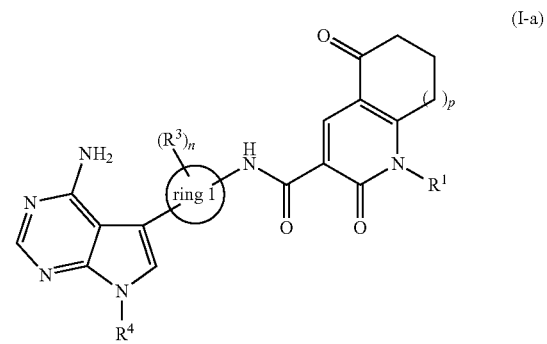

(wherein p is an integer from 0 to 2, and other symbols have the same meanings as defined above) can be produced by the process represented by the following reaction process schemes 1 and 2:

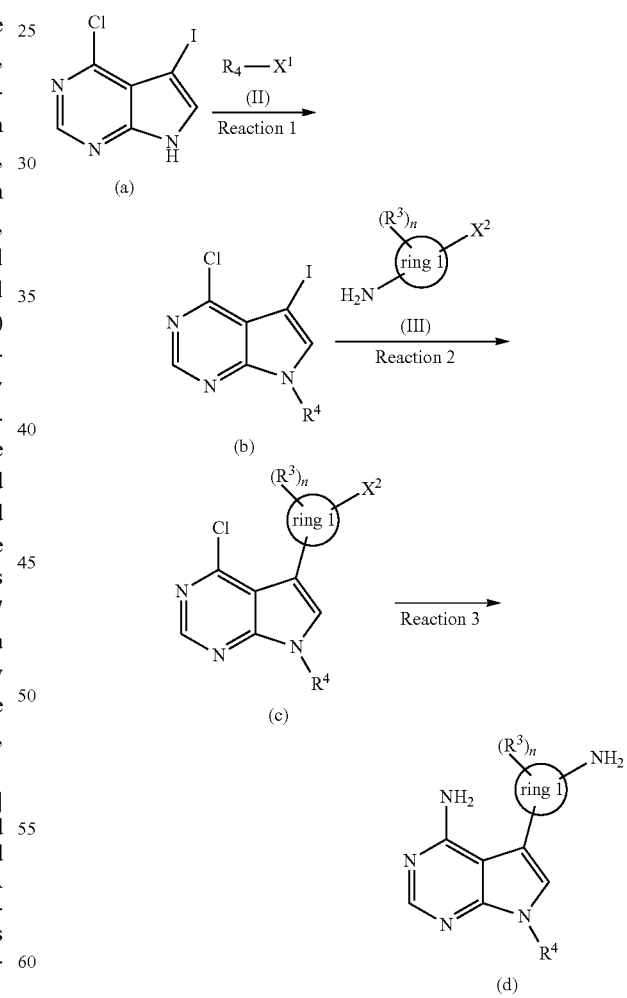

(wherein $X^1$ represents a halogen atom or a hydroxyl group and $X^2$ represents a boronic acid group (—B(OH)$_2$) or a boronic acid ester group (—B(ORi)(ORii) (wherein Ri and Rii represent a C1-3 alkyl group, Ri and Rii together may form a ring), for example, 4,4,5,5-tetramethyl-1,3,2-dioxaborolan-2-yl), and other symbols have the same meanings as defined above).

In the reaction process scheme 1, when $X^1$ represents a halogen atom, the reaction 1 can be carried out by subjecting a compound represented by formula (a), that is, 4-chloro-5-iodo-7H-pyrrolo[2,3-d]pyrimidine (CAS Registry Number: 123148-78-7), and a compound generated by the general formula (II) to an aromatic nucleophilic substitution reaction. This reaction is well-known, and is carried out, for example, in an organic solvent (chlorobenzene, dimethylsulfoxide (DMSO), N,N-dimethylacetamide, N,N-dimethylformamide, chloroform, dioxane, dichloromethane, diethyl ether, tetrahydrofuran, methyl t-butyl ether, and the like), and in the presence or absence of a base (sodium hydride, butyl lithium, potassium hydroxide, potassium tert-butoxide, lithium diisopropylamide (LDA), and the like) at 0 to 200° C.

Furthermore, in the reaction process scheme 1, when $X^1$ represents a hydroxyl group, the reaction 1 can be carried out by subjecting a compound represented by formula (a) and a compound represented by the general formula (II) to Mitsunobu reaction. The Mitsunobu reaction is well-known, and is carried out, for example, in an organic solvent (dichloromethane, diethyl ether, tetrahydrofuran, acetonitrile, benzene, toluene, and the like), in the presence of an azo compound (diethyl azodicarboxylate (DEAD), diisopropyl azodicarboxylate, 1,1'-(azodicarbonyl)dipiperidine, 1,1'-azobis(N,N-dimethylformamide), and the like), and a phosphine compound (for example, triphenylphosphine, tributylphosphine, trimethylphosphine, polymer support triphenylphosphine, and the like) at 0 to 60° C.

In the reaction process scheme 1, the reaction 2 can be carried out by subjecting a compound represented by the general formula (b) and a compound represented by the general formula (III) to a Suzuki coupling reaction. The reaction is well-known, and can be carried out, for example, in an organic solvent (for example, toluene, benzene, N,N-dimethylformamide (DMF), tetrahydrofuran, methanol, acetonitrile, dimethoxyethane, and acetone), in the presence of a base (sodium ethylate, sodium hydroxide, potassium hydroxide, triethylamine, sodium carbonate, sodium hydrogen carbonate, potassium carbonate, cesium carbonate, thallium carbonate, tripotassium phosphate, cesium fluoride, barium hydroxide, tetrabutyl ammonium fluoride, and the like), and in the presence of a palladium catalyst (tetrakis(triphenylphosphine)palladium (Pd(PPh$_3$)$_4$), (dichlorobis(triphenylphosphine)palladium (Cl$_2$Pd(PPh$_3$)$_2$), palladium acetate (Pd(OAc)$_2$), and the like) at a temperature from room temperature to 120° C.

In the reaction process scheme 1, the reaction 3 can be carried out by subjecting a compound represented by the general formula (c) to an azidation reaction, and then to a reduction reaction of an azide group. This azidation reaction is well-known, and is carried out, for example, in an organic solvent (for example, acetonitrile, dimethylsulfoxide (DMSO), N,N-dimethylacetamide, N,N-dimethylformamide, acetone, methanol, ethanol, and hexamethylphosphoric triamide), and in the presence of an azidation agent (for example, sodium azide, potassium azide, and trimethylsilyl azide) at a temperature from room temperature to 100° C. Furthermore, this reduction reaction of an azide group is well-known, and examples of the reaction include (1) a reduction reaction using hydrogen, (2) a hydride reduction reaction, (3) a reduction reaction using silane, (4) a Staudinger reaction, and (5) a reduction reaction using metal.

These methods will be specifically described:

(1) The reduction reaction using hydrogen is carried out, for example, by adding hydrogen gas into an organic solvent (for example, methanol, dioxane, and tetrahydrofuran) in the presence of a catalyst (for example, palladium-carbon) at a temperature from 0 to 100° C.

(2) The hydride reduction reaction is carried out, for example, by reacting a hydride reducing agent (for example, sodium borohydride, zinc borohydride, sodium cyanohydride, lithium triethylborohydride, and lithium aluminum hydride) in an organic solvent (for example, methanol, and dimethyl ether) at a temperature from 0 to 100° C.

(3) The reduction reaction using silane is carried out, for example, by reacting a silane compound (for example, phenyl silane, triethylsilane, and tris(trimethylsilyl)silane) in an organic solvent (for example, dioxane, and toluene) at a temperature from 0 to 100° C.

(4) The Staudinger reaction is carried out, for example, by reacting a phosphine compound (for example, triphenylphosphine, tributylphosphine, and trimethylphosphine) in an organic solvent (for example, methanol, dichloromethane, and tetrahydrofuran) at a temperature from 0 to 100° C.

(5) The reduction reaction using metal is carried out by reacting metal (for example, copper, and zinc) in an acidic solvent (for example, acetic acid, ammonium acetate, a buffer solution with pH4.2-7.2, or a mixed solution of a solution thereof and an organic solvent such as tetrahydrofuran) at a temperature from 0 to 100° C.

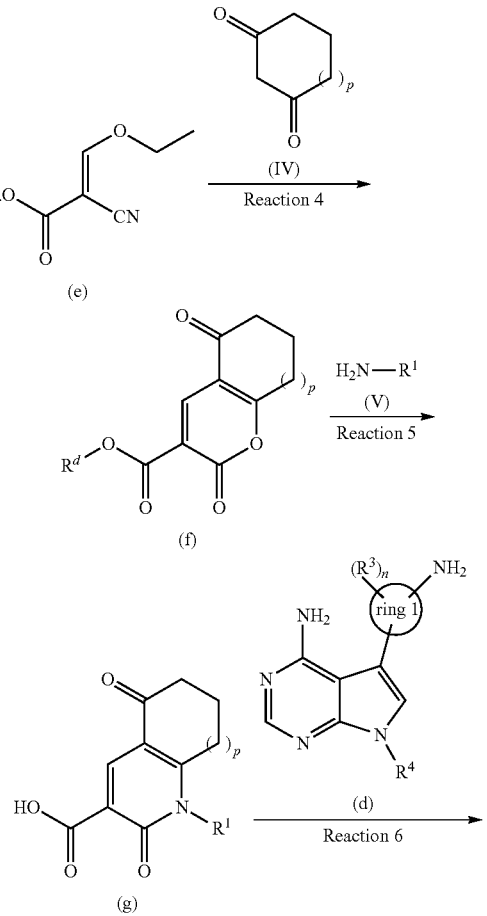

Reaction process scheme 2

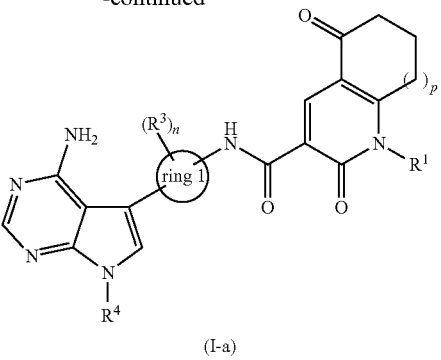

(I-a)

(wherein $R^d$ represents a C1-4 alkyl group, and other symbols have the same meanings as defined above).

In the reaction process scheme 2, the reaction 4 can be carried out by a reaction using a compound represented by the general formula (e) and a compound represented by general formula (IV). This reaction is well-known, and is carried out, for example, in an organic solvent (N,N-dimethylformamide and the like) in the presence of a base (tert-butoxy potassium and the like) at a temperature from 0 to 100° C.

In the reaction process scheme 2, the reaction 5 can be carried out by subjecting a compound represented by the general formula (f) and a compound represented by the general formula (V) to an addition reaction. This addition reaction is well-known, and is carried out, for example, in an alcohol solvent (methanol, ethanol, and the like) at a temperature from 0 to 100° C.

In the reaction process scheme 2, the reaction 6 can be carried out by using and subjecting the compound represented by the general formula (d) and the compound represented by the general formula (g) to an amidation reaction. The amidation reaction is well known, and examples thereof include:

(1) a method using an acid halide,
(2) a method using a mixed acid anhydride, and
(3) a method using a condensing agent.

These methods are specifically described below:

(1) The method using an acid halide is carried out, for example, by reacting a carboxylic acid with an acid halogenating agent (oxalyl chloride, thionyl chloride, and the like) in an organic solvent (chloroform, dichloromethane, diethyl ether, tetrahydrofuran, and the like) or in the absence of any solvent at −20° C. to reflux temperature, and then reacting the obtained acid halide in the presence of a base (pyridine, triethylamine, dimethylaniline, dimethylaminopyridine, diisopropylethylamine, and the like) in amine and an organic solvent (chloroform, dichloromethane, diethyl ether, tetrahydrofuran, and the like) at 0 to 40° C. Additionally, the method can be also carried out by reacting the obtained acid halide with an amine at 0 to 40° C. by using an alkaline aqueous solution (sodium bicarbonate water or sodium hydroxide solution, and the like) in an organic solvent (dioxane, tetrahydrofuran, and the like).

(2) The method using a mixed acid anhydride is carried out, for example, by reacting carboxylic acid with an acid halide (pivaloyl chloride, tosyl chloride, mesyl chloride, and the like) or an acid derivative (ethyl chloroformate, isobutyl chloroformate, and the like) in the presence of a base (pyridine, triethylamine, dimethylaniline, dimethylaminopyridine, diisopropylethylamine, and the like) in an organic solvent (chloroform, dichloromethane, diethyl ether, tetrahydrofuran, and the like) or in the absence of any solvent at 0 to 40° C., and then reacting the obtained mixed acid anhydride with amine in an organic solvent (chloroform, dichloromethane, diethyl ether, tetrahydrofuran, and the like) at 0 to 40° C.

(3) The method using a condensing agent is carried out, for example, by reacting a carboxylic acid with an amine in an organic solvent (chloroform, dichloromethane, dimethyl formamide, diethyl ether, tetrahydrofuran, and the like) or in the absence of any solvent at 0 to 40° C. in the presence or absence of a base (diisopropylethylamine (DIPEA), pyridine, triethylamine, dimethylaniline, dimethylaminopyridine, and the like), using a condensing agent (O-(7-aza-1-benzotriazolyl)-N,N,N,N'-tetramethyluronium hexafluorophosphate (HATU), (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, 1-propylphosphonic acid cyclic anhydride (PPA), and the like) and using, or not using, 1-hydroxybenztriazole (HOBt).

These reactions (1), (2), and (3) are desirably carried out under the atmosphere of an inert gas (argon, nitrogen, etc.) in anhydrous conditions.

In the general formula (I), the compound represented by the general formula (I-b):

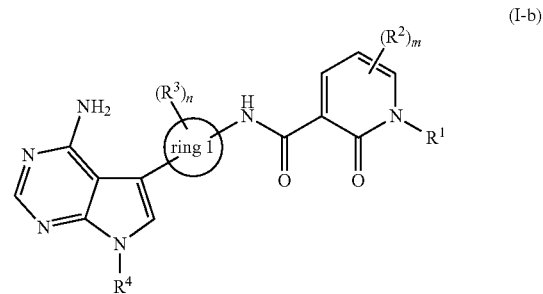

(I-b)

(wherein $R^{2-1}$ represents (1) a C1-8 alkyl group optionally substituted with one to five $R^{21}$, (2) a C2-8 alkenyl group optionally substituted with one to five $R^{22}$, (3) a C2-8 alkynyl group optionally substituted with one to five $R^{23}$, (4) an —$OR^{24}$ group, (5) a C3-7 carbocyclic ring optionally substituted with one to five $R^{25}$, (6) 4- to 7-membered heterocycle optionally substituted with one to five $R^{26}$, (7) a halogen atom, (8) a $C(O)R^{27}$ group, or (9) a $C(O)NR^{28}R^{29}$ group, and other symbols have the same meanings as defined above) can be produced by the reaction process scheme 3.

Reaction process scheme 3

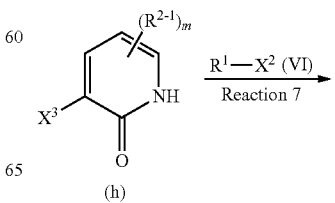

(h)

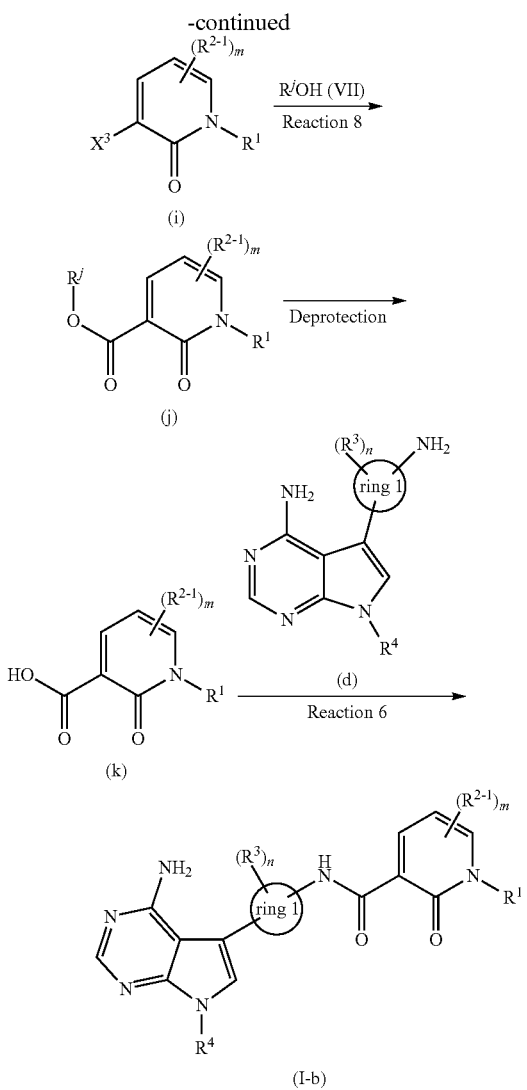

(wherein $X^3$ represents a halogen atom, $R^j$ represents a C1-4 alkyl group, and other symbols have the same meanings as defined above).

In the reaction process scheme 3, the reaction 7 can be carried out by subjecting a compound represented by the general formula (h) and a compound represented by the general formula (VI) to an Ullmann reaction (Chan-Lam-Evans coupling). The reaction is well-known, and can be carried out using a copper catalyst (for example, copper acetate (II)) in, for example, an organic solvent (for example, dichloromethane and acetonitrile) in the presence of a base (for example, triethylamine, pyridine, N,N-diisopropylethylamine) in the presence or in the absence of a drying agent (for example, molecular sieves) at a temperature from room temperature to 200° C.

In the reaction process scheme 3, the reaction 8 can be produced by subjecting a compound represented by the general formula (I) and the compound represented by the general formula (VII) to an esterification reaction. The esterification reaction is well-known, and is carried out, for example, by reacting a palladium catalyst (for example, tetrakis(triphenylphosphine) palladium (Pd(PPh$_3$)$_4$), (dichlorobis (triphenylphosphine)palladium (Cl$_2$Pd(PPh$_3$)$_2$), palladium acetate (Pd(OAc)$_2$)) with carbon monoxide in an organic solvent (for example, DMF, acetonitrile, and benzene) in the presence or absence of a base (for example, potassium carbonate, triethylamine, diisopropylethylamine, diazabicycloundecene (DBU), and sodium acetate), with or without a phosphine compound (for example, triphenylphosphine, tributylphosphine, trimethylphosphine, and 1,1'-bis(diphenylphosphino)ferrocene (dppf)) at a temperature from room temperature to 200° C.

In the reaction process scheme 3, a compound represented by the general formula (k) can be produced by subjecting a compound represented by the general formula (j) to the below-mentioned deprotection reaction.

In the reaction process scheme 3, a compound represented by the general formula (I-b) can be produced by subjecting a compound represented by the general formula (k) and a compound represented by the general formula (d) to a procedure having the same object as in the reaction 6 described in the reaction process scheme 2.

In the reaction process schemes 1, 2, and 3, when a compound represented by each general formula includes a protective group, a deprotection reaction can be carried out if necessary. The deprotection reaction of the protective group is known, and can be carried out by the methods mentioned below. Examples thereof include: (1) a deprotection reactions by alkaline hydrolysis, (2) a deprotection reaction in acidic conditions, (3) a deprotection reaction by hydrogenolysis, (4) a deprotection reaction of a silyl group, (5) a deprotection reaction using metal, (6) a deprotection reaction using a metal complex, and the like.

These methods will be specifically described:

(1) The deprotection reaction by alkaline hydrolysis condition is carried out, for example, in an organic solvent (for example, methanol, tetrahydrofuran, dioxane, etc.) with hydroxide of alkaline metal (for example, sodium hydroxide, potassium hydroxide, lithium hydroxide, etc.), hydroxide of alkaline earth metal (for example, barium hydroxide, calcium hydroxide, etc.), or carbonate (for example, sodium carbonate or potassium carbonate, etc.), or an aqueous solution thereof or a mixture thereof at 0 to 40° C.

(2) The deprotection reaction in acidic conditions is carried out, for example, in an organic solvent (for example, dichloromethane, chloroform, dioxane, ethyl acetate, methanol, isopropyl alcohol, tetrahydrofuran, anisole, etc.), organic acid (for example, acetic acid, trifluoroacetic acid, methanesulfonic acid, p-tosyl acid, etc.), or inorganic acid (for example, hydrochloric acid, sulfuric acid, etc.), or a mixture thereof (for example, hydrogen bromide/acetic acid, etc.) in the presence or absence of 2,2,2-trifluoroethanol at 0 to 100° C.

(3) The deprotection reaction by hydrogenolysis is carried out, for example, in a solvent (for example, ethers (tetrahydrofuran, dioxane, dimethoxyethane, diethyl ether, etc.), alcohols (for example, methanol, ethanol, etc.), benzenes (for example, benzene, toluene, etc.), ketones (for example, acetone, methyl ethyl ketone, etc.), nitriles (for example, acetonitrile, etc.), amides (for example, N,N-dimethylformamide, etc.), water, ethyl acetate, acetic acid, or a mixture of two or more thereof, etc.) in the presence of a catalyst (for example, palladium-carbon, palladium black, palladium hydroxide-carbon, platinum oxide, Raney nickel, etc.) under hydrogen atmosphere at normal pressure or elevated pressure, or in the presence of ammonium formate at 0 to 200° C.

(4) The deprotection reaction of a silyl group is carried out, for example, in a water-miscible organic solvent (for example, tetrahydrofuran, acetonitrile, etc.), by using tetrabutylammonium fluoride at 0 to 40° C. The reaction is also carried out, for example, in organic acid (for example, acetic acid, trifluoroacetic acid, methanesulfonic acid, p-tosyl acid, etc.), or in inorganic acid (for example, hydrochloric acid, sulfuric acid, etc.) or a mixture thereof (for example, hydrogen bromide/acetic acid, etc.) at −10 to 100° C.

(5) The deprotection reaction using a metal is carried out, for example, in an acidic solvent (for example, acetic acid, a buffer solution of pH 4.2 to 7.2, a mixed solution of the solution and an organic solvent thereof such as tetrahydrofuran, etc.) in the presence of powder zinc, if necessary, with an ultrasonic wave applied at 0 to 40° C.

(6) The deprotection reaction using a metal complex is carried out, for example, in an organic solvent (for example, dichloromethane, N,N-dimethylformamide, tetrahydrofuran, ethyl acetate, acetonitrile, dioxane, ethanol, etc.), water or a mixed solvent thereof in the presence of a trap reagent (for example, tributyltin hydride, triethylsilane, dimedone, morpholine, diethylamine, pyrrolidine, etc.), an organic acid (for example, acetic acid, formic acid, 2-ethylhexanic acid, etc.) and/or in the presence of an organic acid salt (for example, sodium 2-ethylhexanate, potassium 2-ethylhexanate, etc.) in the presence or absence of a phosphine reagent (for example, triphenylphosphine, etc.) using a metal complex (for example, tetrakis(triphenylphosphine)palladium(0), dichlorobis(triphenylphosphine)palladium (II), palladium acetate (II), chlorotris(triphenylphosphine) rhodium (I), etc.) at 0 to 40° C.

In addition to the above-mentioned methods, the deprotection reaction can be carried out by, for example, the method described in T. W. Greene, Protective Groups in Organic Synthesis, Wiley, New York, 1999.

Examples of a protective group for a hydroxyl group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group, and the like.

Examples of a protective group for an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group, and the like.

The protective groups for a hydroxyl group and an amino group are not particularly limited to the above-described groups, and may include, in addition to the above-mentioned groups, groups that can be detached easily and selectively. For example, those described in Protective Groups in Organic Synthesis (T. W. Greene, John Wiley & Sons Inc., 1999) may be used.

In each reaction in the present specification, compounds used as starting raw material, for example, the compound represented by the general formula (a), (e), (h), (II), (III), (IV), (V), (VI), or (VII) is well known or can be produced by well-known methods.

In each reaction in the present specification, as apparent to the skilled persons in the art, the reactions involving heating can be carried out using a water bath, an oil bath, a sand bath or a microwave.

In each reaction in the present specification, a solid-supported reagent which is supported on a high molecular polymer (e.g., polystyrene, polyacrylamide, polypropylene, polyethylene glycol, etc.) may be appropriately used.

In each reaction in the present specification, the reaction products can be purified by usual purification methods, for example, by distillation at normal or reduced pressure, by high performance liquid chromatography using silica gel or magnesium silicate, thin layer chromatography, ion-exchange resin, scavenger resin, or column chromatography, or washing, recrystallization, or the like. The purification may be done after each reaction or after several reactions.

[Toxicity]

The toxicity of the compound of the present invention is sufficiently low, and the compound can be safely used as pharmaceuticals.

[Application to Pharmaceuticals]

Since the compound of the present invention has Axl inhibitory activity, it can be used as an agent for preventing and/or treating Axl-related diseases in mammals, especially in human.

In the present invention, examples of the Axl-related diseases include cancer, kidney diseases, immune system disease, and circulatory system disease.

In the present invention, the cancer includes acute myeloid leukemia, chronic myeloid leukemia, melanoma, breast cancer, pancreatic cancer, glioma, esophageal adenocarcinoma, large intestine cancer, renal cell carcinoma, thyroid cancer, non-small cell lung cancer, prostate cancer, stomach cancer, uveal malignant melanoma, ovarian cancer, endometrial cancer, and lymphoma.

In the present invention, examples of the kidney diseases include glomerular nephritis, chronic nephritis, IgA nephritis, sequential (secondary) nephritis, nephrosis nephritis, acute renal failure, chronic renal failure, diabetic nephropathy, gouty nephropathy, interstitial nephritis, and nephropyelitis.

In the present invention, examples of the immune system disease include psoriasis, and rheumatoid arthritis.

In the present invention, examples of the circulatory system disease include atherosclerosis and thrombosis.

Furthermore, since the compound of the present invention has Axl inhibitory activity, it can be used as a metastasis suppressing agent to tumor cell.

The compound of the present invention may be administered as a combination drug in combination with other drugs in order to accomplish the following purposes:
1) to supplement and/or enhance the preventive and/or therapeutic effect of the compound;
2) to improve the kinetics, improvement of absorption, and reduction of the dose of the compound; and/or
3) to eliminate the side effects of the compound.

A combination drug of the compound of the present invention and other drugs may be administered in the form of a compounding agent including these components mixed into one formulation, or may be administered in separate formulations. Administration as separate formulations includes simultaneous administration and administration at different times. In the administration at different times, the compound of the present invention may be administered before the other drug. Alternatively, the other drug may be administered before the compound of the present invention. The method for the administration of these drugs may be the same as each other or different from each other.

Diseases on which the preventive and/or therapeutic effect of the above-mentioned combination drug works are not particularly limited but may be those in which the preventive and/or therapeutic effect of the compound of the present invention is supplemented and/or enhanced.

The other drugs for supplementing and/or enhancing the preventive and/or therapeutic effect of the compound of the present invention against cancer include, for example, alkylating agents, antimetabolites, anticancer antibiotics, plant alkaloids, hormones, platinum compounds, anti-CD20 antibodies, anti-CD52 antibodies, G-CSF formulations, acute promyelocytic leukemia differentiation-inducing agents, kinase inhibitors, topoisomerase inhibitors, aromatase inhibitors, and other anticancer drugs.

The other drug for supplementing and/or enhancing the preventive and/or therapeutic effect of the compound of the present invention against kidney diseases include, for example, steroids, immunosuppressants, angiotensin II antagonistic drugs, angiotensin-converting enzyme inhibitors, antiplatelet drugs, and anticoagulant drugs.

The other drugs for supplementing and/or enhancing the preventive and/or therapeutic effect of the compound of the present invention against immune system diseases include, for example, immunosuppressants, steroids, disease-modifying anti-rheumatic drugs, prostaglandins, prostaglandin synthase inhibitors, phosphodiesterase inhibitors, metalloprotease inhibitors, anti-cytokine protein formulations such as anti-TNF-α formulations, anti-IL-1 formulations, and anti-IL-6 formulation, cytokine inhibitors, and nonsteroidal anti-inflammatory agents.

The other drugs for supplementing and/or enhancing the preventive and/or therapeutic effect of the compound of the present invention against circulatory system diseases include antiplatelet drugs, angiotensin II antagonistic drugs, angiotensin-converting enzyme inhibitors, HMG-CoA reductase inhibitors, and thiazolidine derivative.

Examples of the alkylating agents include nitrogen mustard-N-oxide hydrochloride, cyclophosphamide, ifosfamide, melphalan, thiotepa, carboquone, busulfan, nimustine hydrochloride, dacarbazine, ranimustine, carmustine, chlorambucil, bendamustine, and mechlorethamine.

Examples of the antimetabolites include methotrexate, mercaptopurine, 6-mercaptopurine riboside, fluorouracil, tegafur, tegafur uracil, carmofur, doxifluridine, cytarabine, enocitabine, tegafur gimestat otastat potassium, gemcitabine hydrochloride, cytarabine ocfosfate, procarbazine hydrochloride, and hydroxycarbamide.

Examples of the anticancer antibiotics include actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, zinostatin stimalamer, Gemtuzumab Ozogamicin, and the like.

Examples of the plant formulations include vinblastine sulfate, vincristine sulfate, vindesine sulfate, irinotecan hydrochloride, etoposide, flutamide, vinorelbine tartrate, docetaxel hydrate, paclitaxel, and the like.

Examples of the hormones include estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, aminoglutethimide, androgen bicalutamide, Fulvestrant, and the like.

Examples of the platinum compounds include carboplatin, cisplatin, nedaplatin, and oxaliplatin, and the like.

Examples of the anti-CD20 antibodies include rituximab, ibritumomab, ibritumomab uxetan, and ocrelizumab.

Examples of the anti-CD52 antibodies include alemtuzumab.

Examples of the G-CSF formulation include pegfilgrastim, filgrastim, lenograstim, and nartograstim.

Examples of the differentiation-inducing agent for acute promyelocytic leukemia include tamibarotene, tretinoin, and arsenic trioxide formulations.

Examples of the kinase inhibitors include EGFR inhibitors including erlotinib hydrochloride, gefitinib, cetuximab, and panitumumab; HER2 inhibitors including lapatinib and trastuzumab; BCR-ABL inhibitors including imatinib, dasatinib, and nilotinib; multikinase inhibitors including sunitinib, vandetanib, crizotinib, and sorafenib.

Examples of the topoisomerase inhibitor include topotecan, teniposide, irinotecan, and sobuzoxane.

Examples of the aromatase inhibitor include exemestane.

Examples of the other anticancer agents include L-asparaginase, octreotide acetate, porfimer sodium, mitoxantrone acetate, aceglatone, ubenimex, eribulin mesilate, cladribine, krestin, bexarotene, denileukin diftitox, temozolomide, nelarabine, fludarabine, bevacizumab, pemetrexed, pentostatin, bortezomib, lenalidomide, and calcium folinate.

Examples of the immunosuppressant include azathioprine, ascomycin, everolimus, salazosulfapyridine, cyclosporine, cyclophosphamide, sirolimus, tacrosimus, bucillamine, methotrexate, and leflunomide.

Examples of the steroid include amcinonide, hydrocortisone sodium succinate, prednisolone sodium succinate, methylprednisolone sodium succinate, ciclesonide, difluprednate, betamethasone propionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfate, mometasone furoate, fluocinonide, fluocinolone acetonide, fludroxycortide, flunisolide, prednisolone, alclometasone propionate, clobetasol propionate, dexamethasone propionate, deprodone propionate, fluticasone propionate, beclometasone propionate, betamethasone, methylprednisolone, methylprednisolone suleptanate, methylprednisolone sodium succinate, dexamethasone sodium phosphate, hydrocortisone sodium phosphate, prednisolone sodium phosphate, diflucortolone valerate, dexamethasone valerate, betamethasone valerate, prednisolone valerate acetate, cortisone acetate, diflorasone acetate, dexamethasone acetate, triamcinolone acetate, paramethason acetate, halopredone acetate, fludrocortisone acetate, prednisolone acetate, methylprednisolone acetate, clobetasone butyrate, hydrocortisone butyrate, hydrocortisone butyrate propionate, and betamethasone butyrate propionate.

Examples of the angiotensin II antagonistic drug include Losartan, candesartan, valsartan, irbesartan, olmesartan, telmisartan, and the like.

Examples of the angiotensin-converting enzyme inhibitor include alacepril, imidapril hydrochloride, quinapril hydrochloride, temocapril hydrochloride, delapril hydrochloride, benazepril hydrochloride, captopril, trandolapril, perindopril erbumine, enalapril maleate, lisinopril, and the like.

Examples of the antiplatelet drugs include dipyridamole, and dilazep hydrochloride hydrate.

Examples of the anticoagulant drugs include warfarin and heparin.

Examples of the disease-modifying anti-rheumatic drugs include D-penicillamine, actarit, auranofin, salazosulfapyridine, hydroxychloroquine, bucillamine, methotrexate, leflunomide, lobenzarit sodium, aurothioglucose, and sodium aurothiomalate.

Examples of the prostaglandins (hereinafter, abbreviated as "PG") include PGE1 formulations (examples: alprostadil alfadex, alprostadil), PGI2 formulations (example: beraprost sodium), PG receptor agonists, and PG receptor antagonists. Examples of the PG receptor include PGE receptors (EP1, EP2, EP3, and EP4), PGD receptors (DP, and CRTH2), PGF receptors (FP), PGI2 receptors (IP), and TX receptors (TP).

Examples of the prostaglandin synthase inhibitor include salazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, piproxen, piroxicam, piroxicam cinnamate, zaltoprofen, and pranoprofen.

Examples of the phosphodiesterase inhibitor include rolipram, cilomilast, Bay19-8004, NIK-616, roflumilast (BY-217), cipamfylline (BRL-61063), atizoram (CP-80633), ONO-6126, SCH-351591, YM-976, V-11294A, PD-168787, D-4396, and IC-485.

Examples of the anti-TNF-α formulation include anti-TNF-α antibodies, soluble TNF-α receptor, anti-TNF-α receptor antibodies, and soluble TNF-α binding protein, and particularly infliximab and etanercept.

Examples of the anti-IL-1 formulation include anti-IL-1 antibodies, soluble IL-1 receptor, anti-IL-1Ra antibodies and/or anti-IL-1 receptor antibodies, and particularly anakinra.

Examples of the anti-IL-6 formulation include anti-IL-6 antibodies, soluble IL-6 receptor, and anti-IL-6 receptor antibodies, and particularly tocilizumab.

Examples of the cytokine inhibitor include suplatast tosylate, T-614, SR-31747, and sonatimod.

Examples of the HMG-CoA reductase inhibitor include atorvastatin, fluvastatin, lovastatin, pitavastatin, pravastatin, rosuvastatin, and simvastatin.

Examples of the thiazolidine derivative include pioglitazone, ciglitazone, rosiglitazone, and troglitazone.

Furthermore, the combination drugs to be combined with a compound of the present invention includes not only ones discovered to date, but also ones that may be discovered in the future.

The compound of the present invention is usually administered systemically or locally, by oral or parenteral administration. Examples of oral agents include liquid medicines for internal use (for example, elixirs, syrups, pharmaceutically acceptable water-based agents, suspensions, and emulsions), and solid medicine for internal use (for example, tablets (including sublingual tablets and orally disintegrating tablets), pills, capsules (including hard capsules, soft capsules, gelatin capsules, and microcapsules), powders, granules, and lozenges). Examples of parenteral agents include liquid medicines (for example, injection agents (for example, subcutaneous injection agents, intravenous injection agents, intramuscular injection agents, intraperitoneal injection agents, and drip agents), eye drops (for example, aqueous eye drops (aqueous eye drops, aqueous eye drop suspensions, viscous eye drops, and solubilized eye drops, etc.), and nonaqueous eye drops (for example, nonaqueous eye drops and nonaqueous eye drop suspensions), and the like), agents for external use (for example, ointments (ophthalmic ointments, and the like)), and ear drops, and the like. These formulations may be controlled release agents such as rapid release formulations, sustained release formulations, and the like. These formulations can be produced by well-known methods, for example, by the methods described in The Japanese Pharmacopoeia.

Liquid medicines for internal use as the oral agent can be produced by, for example, dissolving or suspending an active ingredient in a generally used diluent (for example, purified water, ethanol, or mixture liquid thereof, or the like). The liquid medicine may include a wetting agent, a suspension agent, a sweetening agent, a flavoring material, an aromatic substance, a preservative, a buffer agent, and the like.

Solid medicines for internal use as the oral agent are formulated by, for example, mixing the active ingredient with, for example, a vehicle (for example, lactose, mannitol, glucose, microcrystalline cellulose, and starch), a binder (for example, hydroxypropyl cellulose, polyvinylpyrrolidone, and magnesium metasilicate aluminate), a disintegrant (for example, sodium carboxymethylcellulose), a lubricant (for example, magnesium stearate), a stabilizer, a dissolution adjuvant (for example, glutamic acid and aspartic acid), and the like, and formulating according to standard methods. As necessary, coating may be carried out with a coating agent (for example, sugar, gelatin, hydroxypropyl cellulose, and hydroxypropyl methyl cellulose phthalate), and coating of two or more layers may be employed.

Agents for external use as parenteral agents are produced by well-known methods or generally used prescriptions. For example, an ointment may be produced by incorporation or melting of an active ingredient into base material. The ointment base material is selected from well-known material or generally used material. For example, a single material or a mixture of two or more of materials are selected from higher fatty acids and higher fatty acid esters (for example, adipic acid, myristic acid, palmitic acid, stearic acid, oleic acid, adipate esters, myristate esters, palmitate esters, stearate esters, and oleate esters), waxes (for example, beeswax, spermaceti, and ceresin), surfactants (for example, polyoxyethylene alkyl ether phosphate esters), higher alcohols (for example, cetanol, stearyl alcohol, and cetostearyl alcohol), silicone oils (for example, dimethylpolysiloxane), hydrocarbons (for example, hydrophilic petrolatum, white petrolatum, purified lanolin, and liquid paraffin), glycols (for example, ethylene glycol, diethylene glycol, propylene glycol, polyethylene glycol, and macrogol), plant oils (for example, castor oil, olive oil, sesame oil, and turpentine oil), animal oils (for example, mink oil, egg yolk oil, squalane, and squalene), water, absorption promoters, and anti-irritants. Furthermore, a humectant, preservative, stabilizer, antioxidant, fragrance, and the like, may be included.

The injection agents as parenteral agents include solutions, suspensions, emulsions and solid injection agents to be dissolved or suspended in a solvent before use. The injection agent is used by, for example, dissolving, suspending or emulsifying an active ingredient in a solvent. Examples of the solvent include distilled water for injection, physiological saline, vegetable oils, alcohols such as propylene glycol, polyethylene glycol, ethanol, and mixtures thereof. Furthermore, the injection agent may contain a stabilizer, a dissolution aid (glutamic acid, aspartic acid, and Polysorbate 80 (registered trademark), etc.), a suspending agent, an emulsifying agent, a soothing agent, a buffer, a preservative, and the like. Such an injection agent is produced by sterilizing at the final step or employing an aseptic process. Furthermore, it is also possible to employ an aseptic solid product such as a freeze-dried product produced and sterilized or dissolved in aseptic distilled water for injection or other solvent before use.

When the compound of the present invention or combination agents of the compound of the present invention and other agents are used for the above-mentioned purposes, they are usually administered systemically or locally, usually by oral or parenteral administration. The doses to be administered are different depending upon ages, body weights, symptoms, therapeutic effects, administration method, treatment time, and the like. The doses per adult person are generally from 1 ng to 1000 mg per dose, once or several times per day, by oral administration, from 0.1 ng to 100 mg per dose, once or several times per day, by parenteral administration, or continuous administration 1 to 24 hours per day intravenously. Needless to say, as mentioned above, the doses to be used vary dependent upon various conditions. Therefore, doses lower than the ranges specified above may be sufficient in some cases, and doses higher than the ranges specified above are needed in some cases.

EXAMPLES

Hereinafter, the present invention is described in detail with reference to Examples mentioned below, but the present invention is not limited thereto.

Solvents given in parentheses shown in chromatographic separation and TLC each indicates the eluting solvent or the developing solvent used, and the ratio is expressed in ratio by volume. The description "NH silica" denotes that CHROMATOREX NH TLC PLATE (catalog No.; 3800003) manufactured by FUJI SILYSIA CHEMICAL LTD. is used.

LC-MS/ELSD was carried out in the following conditions:

{Column: Waters ACQUITY $C_{18}$ (particle diameter: 1.7×$10^{-6}$ m; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (rate of mobile phase (A):mobile phase (B)): [0 min] 95:5; [0.1 min] 95:5; [1.2 min] 5:95; [1.4 min] 5:95; [1.41 min] 95:5; [1.5 min] 95:5; detector: UV (PDA), ELSD, MS}

Alternatively, as to compounds described in Examples 10(1), 10(2), 10(3), 10(4), 15(1), 51, 51(1), 51(2), 51(3), 64, 68, and 131, LC-MS/ELSD was carried out in the following conditions:

{Column: Waters Xterra MS $C_{18}$ (particle diameter: 5.0×$10^{-6}$ m; column length: 50×4.6 mm I.D.); flow rate: 1.5 mL/min; column temperature: 40° C.; mobile phase (A): 0.1% trifluoroacetic acid aqueous solution; mobile phase (B): 0.1% trifluoroacetic acid-methanol solution; gradient (rate of mobile phase (A):mobile phase (B)): [0 min] 95:5; [1 min] 95:5; [4 min] 0:100; [4.5 min] 0:100; [4.51 min] 95:5; [6 min] 95:5; detector: UV (PDA), ELSD, MS}

The description in a parenthesis in the NMR data shows a solvent used for measurement.

Mass spectrum (MS) was obtained by using Quadrupole Mass Spectrometer by either the Electro Spray Ionization (ESI) method or the Atmospheric Pressure Chemical Ionization (APCI) method.

Name of the compounds used in this specification are named by using ACD/Name (registered trademark) manufactured by Advanced Chemistry Development Inc., which is a computer program for naming compounds according to the regulation of IUPAC, or named according to the naming method of IUPAC.

Example 1

4-chloro-5-iodo-7-methyl-7H-pyrrolo[2,3-d]pyrimidine

Under argon atmosphere, to a tetrahydrofuran (THF) solution (40 mL) of 4-chloro-5-iodo-7H-pyrrolo[2,3-d]pyrimidine (5000 mg) (CAS Registry Number: 123148-78-7), sodium hydride (55% in mineral oil) (858 mg) was added. The resulting mixture was stirred at 0° C. for 30 minutes. Thereafter, iodomethane (1.33 mL) was added thereto, and the mixture was stirred at room temperature for two hours. Water was added thereto, followed by extraction with ethyl acetate. The extracted solution was washed with water and a saturated saline solution, and dried over anhydrous sodium sulfate. Thereafter, the solvent was removed by evaporation under reduced pressure to obtain the title compound (5386 mg) having the following physical property values.

TLC: Rf 0.84 (ethyl acetate);
$^1$H-NMR (DMSO-$d_6$): δ 3.81, 7.97, 8.63.

Example 2

4-(4-chloro-7-methyl-7H-pyrrolo[2,3-d]pyrimidin-5-yl)aniline

Under argon atmosphere, to a 1,4-dioxane solution (200 mL) of the compound (10 g) produced in Example 1, 4-(4,4,5,5-tetramethyl-1,3,2-dioxaborolan-2-yl)aniline (9.0 g), 2 mol/L potassium phosphate aqueous solution (50 mL), and tetrakis(triphenylphosphine)palladium (3.9 g) were added. The mixture was stirred at a bath temperature (90° C.) for 14 hours, and left to cool to room temperature. Then, water was added thereto, followed by extraction with ethyl acetate. The extracted solution was washed with water and a saturated saline solution, and dried over anhydrous sodium sulfate. Thereafter, the solvent was removed by evaporation under reduced pressure. The resulting product was purified by column chromatography on silica gel (ethyl acetate→ethyl acetate:methanol=9:1) to obtain the title compound (8.8 g) having the following physical property values.

TLC: Rf 0.70 (ethyl acetate);
$^1$H-NMR (DMSO-$d_6$): δ 3.85, 5.15, 6.60, 7.13, 7.61, 8.60.

Example 3

5-(4-aminophenyl)-7-methyl-7H-pyrrolo[2,3-d]pyrimidine-4-amine

Under argon atmosphere, to a DMF solution (70 mL) of the compound (9.2 g) produced in Example 2, sodium azide (4.6 g) was added. The mixture was stirred at a bath temperature (80° C.) for four hours, and left to cool to room temperature. Then, water was added thereto, followed by extraction with ethyl acetate. The extracted solution was washed with water and a saturated saline solution, and dried over anhydrous sodium sulfate. Thereafter, the solvent was removed by evaporation under reduced pressure. The resulting product was suspended in water (3 mL) and THF (110 mL), and 1 mol/L trimethylphosphine in THF solution (106 mL) was added thereto. The resulting mixture was stirred at a bath temperature (60° C.) for three hours. The solvent was removed by evaporation under reduced pressure. The resulting product was purified by column chromatography on silica gel (hexane:ethyl acetate, 7:3→0:10) to obtain the title compound (6.5 g) having the following physical property values.

TLC: Rf 0.63 (ethyl acetate:methanol=5:1);
$^1$H-NMR (DMSO-$d_6$): δ 3.69, 5.17, 5.95, 6.64, 7.07, 8.09.

Example 4 ethyl 2,5-dioxo-5,6,7,8-tetrahydro-2H-chromene-3-carboxylate

At room temperature, 1,3-cyclohexanedione (CAS registration No.: 504-02-9) (13.25 g) was dissolved in N,N- dimethyl formamide (DMF) (200 mL), and tert-butoxy potassium (13.26 g) and ethyl (E)-2-cyano-3-ethoxy-2-propenoate (CAS registration No.: 94-05-3) (20.00 g) were added thereto. The mixture was stirred for 21 hours. The reaction solution was diluted with ethyl acetate, 2 N hydrochloric acid aqueous solution was added thereto, and the mixture was stirred. Ethyl acetate and water were further added, and the organic layer was extracted. The extract was washed with a saturated saline solution, then dried over anhydrous sodium sulfate, and the solvent was removed by evaporation under reduced pressure to obtain the title compound (23.62 g) having the following physical property values.

TLC: Rf 0.35 (hexane:ethyl acetate=1:1);
$^1$H-NMR (CDCl$_3$): δ 1.37, 2.19, 2.61, 2.92, 4.36, 8.63.

Example 5

2,5-dioxo-1-phenyl-1,2,5,6,7,8-hexahydro-3-quinoline carboxylic acid

The compound (10.00 g) produced in Example 4 was dissolved in ethanol (200 mL) at room temperature, aniline (3.94 g) was added thereto, and the mixture was stirred for six hours. Solids precipitated from the reaction solution were collected by filtration through Kiriyama funnel, and washed with ethanol. The obtained residue was dried under reduced pressure at 60° C. to obtain the title compound (4.01 g) having the following physical property values.

TLC: Rf 0.37 (dichloromethane:methanol=9:1);
$^1$H-NMR (CDCl$_3$): δ 2.11, 2.60, 7.25, 7.63, 9.21.

Example 6

N-[4-(4-amino-7-methyl-7H-pyrrolo[2,3-d]pyrimidin-5-yl)phenyl]-2,5-dioxo-1-phenyl-1,2,5,6,7,8-hexahydro-3-quinolinecarboxamide

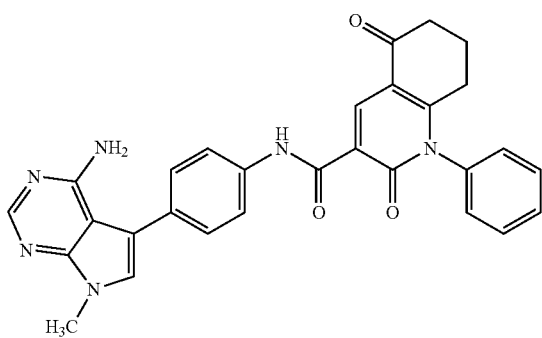 [SMILES: Cn1cc(-c2ccc(NC(=O)c3cc4c(n(-c5ccccc5)c3=O)CCCC4=O)cc2)c2c(N)ncnc21]

Under argon atmosphere, to a DMF solution (3 mL) of the compound (50 g) produced in Example 3 and the compound (75 g) produced in Example 5, HATU (95 mg) and DIPEA (0.10 mL) were added. The resulting mixture was stirred at room temperature for 12 hours. To the reaction solution, sodium bicarbonate aqueous solution was added, followed by extraction with ethyl acetate. The organic layer was washed with a saturated saline solution, then dried over anhydrous sodium sulfate, and concentrated to obtain the title compound (80 mg) having the following physical property values.

(LC-MS/ELSD): (retention time: 0.72 minutes);
$^1$H-NMR (CDCl$_3$): δ 2.09-2.13, 2.54-2.64, 3.83, 5.09, 6.91, 7.26-7.35, 7.43, 7.62-7.69, 7.78, 8.33, 9.34, 11.45.

Example 6(1) to 6(15)

The compound produced in Example 3 and the corresponding carboxylic acid derivatives instead of the compound produced in Example 5 were used and subjected to the procedure having the same object as in Example 6 to obtain the following compounds of Examples.

Example 6(1)

N-[4-(4-amino-7-methyl-7H-pyrrolo[2,3-d]pyrimidin-5-yl)phenyl]-1-(4-fluorophenyl)-2,5-dioxo-1,2,5,6,7,8-hexahydro-3-quinolinecarboxamide (LC-MS/ELSD): (retention time: 0.76 minutes);
$^1$H-NMR (CDCl$_3$): δ 2.09-2.11, 2.54-2.63, 3.80, 5.08, 6.91, 7.27-7.37, 7.42, 7.77, 8.33, 9.32, 11.36.

Example 6(2)

N-[4-(4-amino-7-methyl-7H-pyrrolo[2,3-d]pyrimidin-5-yl)phenyl]-1-(3-fluorobenzyl)-2,5-dioxo-1,2,5,6,7,8-hexahydro-3-quinolinecarboxamide (LC-MS/ELSD): (retention time: 0.76 minutes);
$^1$H-NMR (CDCl$_3$): δ 2.11-2.24, 2.60, 2.96, 3.84, 5.10, 5.50, 6.86-6.97, 7.02-7.11, 7.33-7.42, 7.46, 7.71, 8.35, 9.31, 11.58.

Example 6(3)

N-[4-(4-amino-7-methyl-7H-pyrrolo[2,3-d]pyrimidin-5-yl)phenyl]-1-[(1R)-2-hydroxy-1-phenylethyl]-2,5-dioxo-1,2,5,6,7,8-hexahydro-3-quinolinecarboxamide (LC-MS/ELSD): (retention time: 0.71 minutes);
$^1$H-NMR (DMSO-d$_6$): δ 1.95-2.23, 2.52-2.64, 3.19-3.27, 3.74, 4.37-4.65, 5.13-5.30, 5.92, 7.25-7.45, 7.68-7.82, 8.15, 8.91, 11.41.

Example 6(4)

N-[4-(4-amino-7-methyl-7H-pyrrolo[2,3-d]pyrimidin-5-yl)phenyl]-1-(cyclopropylmethyl)-2,5-dioxo-1,2,5,6,7,8-hexahydro-3-quinolinecarboxamide trifluoroacetate (LC-MS/ELSD): (retention time: 0.73 minutes);
$^1$H-NMR (CDCl$_3$): δ 1.24-1.31, 2.15, 2.57-2.59, 3.25, 3.84, 4.20, 7.47, 7.59, 7.86, 8.41, 8.87, 11.77.

Example 6(5)

N-[4-(4-amino-7-methyl-7H-pyrrolo[2,3-d]pyrimidin-5-yl)-2-(trifluoromethoxy)phenyl]-2,5-dioxo-1-phenyl-1,2,5,6,7,8-hexahydro-3-quinolinecarboxamide (LC-MS/ELSD): (retention time: 0.84 minutes);
$^1$H-NMR (CDCl$_3$): δ 1.26, 2.03-2.15, 2.50-2.64, 4.21, 5.22, 7.02, 7.24-7.26, 7.27-7.29, 7.36-7.46, 7.56-7.67, 8.30, 8.68, 11.84.

Example 6(6)

N-[4-(4-amino-7-methyl-7H-pyrrolo[2,3-d]pyrimidin-5-yl)phenyl]-2',5'-dioxo-1'-phenyl-2',5',6',8'-tetrahydro-1'H-spiro[cyclobutane-1,7'-quinoline]-3'-carboxamide TLC: Rf 0.53 (ethyl acetate:methanol=19:1);
$^1$H-NMR (CDCl$_3$): δ 1.70-2.05, 2.63, 2.73, 3.83, 5.09, 6.91, 7.24-7.30, 7.38-7.45, 7.60-7.80, 8.33, 9.29, 11.42.

Example 6(7)

N-[4-(4-amino-7-methyl-7H-pyrrolo[2,3-d]pyrimidin-5-yl)phenyl]-1-cyclobutyl-2,5-dioxo-1,2,5,6,7,8-hexahydro-3-quinolinecarboxamide TLC: Rf 0.61 (ethyl acetate:methanol:28% ammonia water=9:1:0.5);
$^1$H-NMR (CDCl$_3$): δ 1.78-2.25, 2.47-2.64, 2.87-3.05, 3.84, 4.76-4.90, 5.10, 6.94, 7.46, 7.86, 8.34, 9.16, 11.63.

Example 6(8)

N-[4-(4-amino-7-methyl-7H-pyrrolo[2,3-d]pyrimidin-5-yl)phenyl]-6,6-dimethyl-2,5-dioxo-1-phenyl-1,2,5,6,7,8-hexahydro-3-quinolinecarboxamide TLC: Rf 0.71 (ethyl acetate:methanol:28% ammonia water=9:1:0.5);
$^1$H-NMR (CDCl$_3$): δ 1.22, 1.92, 2.54, 3.83, 5.08, 6.91, 7.19-7.37, 7.42, 7.58-7.70, 7.78, 8.33, 9.34, 11.46.

Example 6(9)

N-[4-(4-amino-7-methyl-7H-pyrrolo[2,3-d]pyrimidin-5-yl)phenyl]-1-(3-hydroxy-3-methyl-2-butanyl)-2,5-dioxo-1,2,5,6,7,8-hexahydro-3-quinolinecarboxamide TLC: Rf 0.55 (ethyl acetate:methanol:28% ammonia water=9:1:0.5);
$^1$H-NMR (CDCl$_3$): δ 1.15, 1.41, 1.66, 2.22-2.33, 2.60-2.67, 2.94-3.15, 3.85, 4.44-4.54, 5.10, 5.57, 6.95, 7.48, 7.84, 8.34, 9.30, 11.39.

Example 6(10)

N-[4-(4-amino-7-methyl-7H-pyrrolo[2,3-d]pyrimidin-5-yl)phenyl]-1-(4,4-difluorocyclohexyl)-2,5-dioxo-1,2,5,6,7,8-hexahydro-3-quinolinecarboxamide TLC: Rf 0.56 (ethyl acetate:methanol:28% ammonia water=9:1:0.5);
$^1$H-NMR (DMSO-d$_6$): δ 1.80-1.93, 2.01-2.22, 2.49-2.60, 2.83-3.03, 3.19-3.28, 3.73, 4.40-4.63, 6.00-6.20, 7.30, 7.43, 7.81, 8.14, 8.82, 11.58.

Example 6(11)

N-[4-(4-amino-7-methyl-7H-pyrrolo[2,3-d]pyrimidin-5-yl)phenyl]-2,5-dioxo-1-(3-pentanyl)-1,2,5,6,7,8-hexahydro-3-quinolinecarboxamide TLC: Rf 0.19 (ethyl acetate:methanol=19:1);
$^1$H-NMR (CDCl$_3$): δ 0.89, 1.95-2.12, 2.17-2.28, 2.36-2.53, 2.60, 3.03, 3.84, 4.10-4.24, 5.10, 6.94, 7.46, 7.85, 8.34, 9.22, 11.70.

Example 6(12)

N-[4-(4-amino-7-methyl-7H-pyrrolo[2,3-d]pyrimidin-5-yl)phenyl]-2',5'-dioxo-1'-phenyl-2',5',6',8'-tetrahydro-1'H-spiro[cyclopropane-1,7'-quinoline]-3'-carboxamide TLC: Rf 0.55 (ethyl acetate:methanol=19:1);
$^1$H-NMR (CDCl$_3$): δ 0.35-0.44, 0.50-0.60, 2.40, 2.47, 3.83, 5.10, 6.91, 7.22-7.28, 7.42, 7.58-7.69, 7.78, 8.33, 9.36, 11.43.

Example 6(13)

N-[4-(4-amino-7-methyl-7H-pyrrolo[2,3-d]pyrimidin-5-yl)phenyl]-2,5-dioxo-1-phenyl-2,5,6,7,8,9-hexahydro-1H-cyclohepta[b]pyridine-3-carboxamide TLC: Rf 0.43 (dichloromethane:methanol=9:1);
$^1$H-NMR (DMSO-d$_6$): δ 1.61-1.83, 2.60-2.77, 3.72, 6.15, 7.30, 7.41, 7.48, 7.52-7.68, 7.79, 8.15, 8.78, 11.61.

Example 6(14)

N-[4-(4-amino-7-methyl-7H-pyrrolo[2,3-d]pyrimidin-5-yl)phenyl]-5-methyl-2-oxo-1-phenyl-1,2-dihydro-3-pyridinecarboxamide (LC-MS/ELSD): (retention time: 0.78 minutes);
$^1$H-NMR (DMSO-d$_6$): δ 2.27, 3.83, 5.09, 6.92, 7.39-7.46, 7.50-7.61, 7.79-7.84, 8.34, 8.64, 12.09.

Example 6(15)

N-[4-(4-amino-7-methyl-7H-pyrrolo[2,3-d]pyrimidin-5-yl)phenyl]-4,6-dimethyl-2-oxo-1-phenyl-1,2-dihydro-3-pyridinecarboxamide (LC-MS/ELSD): (retention time: 0.72 minutes);
$^1$H-NMR (CDCl$_3$): δ 2.03, 2.83, 3.82, 5.07, 6.27, 6.89, 7.24, 7.39, 7.53, 7.60, 7.74, 8.33, 12.06.

Example 7 tert-butyl 4-(4-chloro-5-iodo-7H-pyrrolo[2,3-d]pyrimidin-7-yl)piperidine-1-carboxylate To a solution of diisopropyl azodicarboxylate (CAS registration No.: 2446-83-5) (500 mg) in THF (25 mL), triphenylphosphine (700 mg) was added at 0° C. The resulting mixture was stirred for 10 minutes. Then, 4-chloro-5-iodo-7H-pyrrolo[2,3-d]pyrimidine (500 mg) and tert-butyl 4-hydroxypiperidine-1-carboxylate (CAS registration No.: 109384-19-2) (360 mg) was added thereto, and the resulting solution was stirred at room temperature for 12 hours. The solvent was removed by evaporation under reduced pressure. The obtained residue was purified by column chromatography on silica gel (hexane:ethyl acetate=100:0→30:70) to obtain the title compound (450 mg) having the following physical property values.

$^1$H-NMR (CDCl$_3$): δ 1.49, 1.80-2.10, 2.87-2.99, 4.25-4.40, 4.83-4.97, 7.42, 8.60.

Example 8

4-chloro-5-iodo-7-(4-piperidinyl)-7H-pyrrolo[2,3-d]pyrimidine trifluoroacetate

Trifluoroacetic acid (10.0 mL) was added to a dichloromethane solution (70.0 mL) of the compound (2 g) produced in Example 7. The resulting mixture was stirred at room temperature for three hours. The solvent was distilled off in a vacuum to obtain the title compound. The obtained compound was used for the subsequent reaction without purification.

MS (M+H): 363.

Example 9

4-chloro-5-iodo-7-(1-methyl-4-piperidinyl)-7H-pyrrolo[2,3-d]pyrimidine

The compound (2 g) produced in Example 8 was reacted with sodium triacetoxyborohydride (4.5 g) in a formaldehyde solution (60.0 mL) at room temperature for three hours to obtain the title compound (1.4 g) having the following physical property values. The obtained compound was used for the subsequent reaction without purification.

$^1$H-NMR (CDCl$_3$): δ 1.98-2.13, 2.14-2.27, 2.36, 2.96-3.08, 4.66-4.81, 7.45, 8.60.

Example 10

N-{4-[4-amino-7-(1-methyl-4-piperidinyl)-7H-pyrrolo[2,3-d]pyrimidin-5-yl]phenyl}-2,5-dioxo-1-phenyl-1,2,5,6,7,8-hexahydro-3-quinolinecarboxamide The compound (1.4 g) produced in Example 9, 4-(4,4,5,5-tetramethyl-1,3,2-dioxaborolan-2-yl)aniline, and the compound (30 mg) produced in Example 5 were used and subjected to the procedure having the same object as in Example 2→Example 3→Example 6 to obtain the title compound (25 mg) having the following physical property values.

(LC-MS/ELSD): (retention time: 0.57 minutes);
$^1$H-NMR (CDCl$_3$): δ 2.01-2.14, 2.20-2.29, 2.35, 2.53-2.63, 3.01, 4.67-4.76, 5.08, 7.02, 7.25-7.34, 7.42, 7.60-7.69, 7.60-7.69, 7.79, 8.31, 9.33, 11.42.

Example 10(1) to 10(15)

4-chloro-5-iodo-7H-pyrrolo[2,3-d]pyrimidine, tert-butyl 4-hydroxypiperidine-1-carboxylate or the corresponding alcohol derivative instead thereof, and a carboxylic acid derivative instead of the compound produced in Example 5 were used and subjected to the procedure having the same object as in Example 7→Example 10 or the procedure having the same object as in Example 7→Example 8→Example 9→Example 10 to obtain the following compounds of Examples.

Example 10(1)

N-[4-(4-amino-7-cyclopentyl-7H-pyrrolo[2,3-d]pyrimidin-5-yl)phenyl]-2-oxo-1-phenyl-1,2-dihydro-3-pyridinecarboxamide

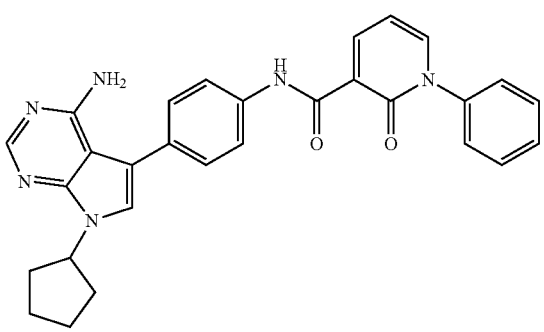 [SMILES: Nc1ncnc2c1c(-c1ccc(NC(=O)c3cccn(-c4ccccc4)c3=O)cc1)cn2C1CCCC1]

(LC-MS/ELSD): (retention time: 4.43 minutes);
$^1$H-NMR (DMSO-d$_6$): δ 1.62-1.75, 1.88-1.92, 2.09-2.11, 5.05-5.09, 6.06, 6.73, 7.40, 7.46, 7.53-7.60, 7.79, 8.11-8.13, 8.60, 12.03.

Example 10(2)

N-[4-(4-amino-7-cyclopentyl-7H-pyrrolo[2,3-d]pyrimidin-5-yl)phenyl]-1-(4-fluorophenyl)-2-oxo-1,2-dihydro-3-pyridinecarboxamide (LC-MS/ELSD): (retention time: 4.43 minutes);
$^1$H-NMR (DMSO-d$_6$): δ 1.62-1.75, 1.88-1.92, 2.09-2.11, 5.05-5.09, 6.06, 6.73, 7.40, 7.46, 7.53-7.60, 7.79, 8.11-8.13, 8.60, 12.03.

Example 10(3)

N-{4-[4-amino-7-(3-oxetanyl)-7H-pyrrolo[2,3-d]pyrimidin-5-yl]phenyl}-2-oxo-1-phenyl-1,2-dihydro-3-pyridinecarboxamide (LC-MS/ELSD): (retention time: 3.91 minutes);
$^1$H-NMR (DMSO-d$_6$): δ 4.96-5.04, 5.84-5.91, 6.11, 6.73, 7.47-7.61, 7.73, 7.81, 8.11-8.14, 8.31, 8.60, 12.04.

Example 10(4)

N-{4-[4-amino-7-(1-methyl-3-pyrrolidinyl)-7H-pyrrolo[2,3-d]pyrimidin-5-yl]phenyl}-2-oxo-1-phenyl-1,2-dihydro-3-pyridinecarboxamide (LC-MS/ELSD): (retention time: 3.60 minutes);
$^1$H-NMR (DMSO-d$_6$): δ 1.95-1.99, 2.31, 2.26-2.39, 2.67-2.76, 2.92-2.95, 5.34-5.36, 6.08, 6.72, 7.42-7.58, 7.78-7.81, 7.92, 8.11, 8.12, 8.59, 12.05.

Example 10(5)

N-(4-{4-amino-7-[(3S)-tetrahydro-3-furanyl]-7H-pyrrolo[2,3-d]pyrimidin-5-yl}phenyl)-2-oxo-1-phenyl-1,2-dihydro-3-pyridinecarboxamide (LC-MS/ELSD): (retention time: 0.71 minutes);
$^1$H-NMR (CDCl$_3$): δ 2.17-2.21, 2.52-2.62, 3.90-3.96, 4.02-4.09, 4.17-4.22, 5.10, 5.55-5.60, 6.61, 7.10, 7.41-7.45, 7.54-7.59, 7.65, 7.82, 8.31, 8.77, 11.97.

Example 10(6)

N-(4-{4-amino-7-[(3R)-tetrahydro-3-furanyl]-7H-pyrrolo[2,3-d]pyrimidin-5-yl}phenyl)-2-oxo-1-phenyl-1,2-dihydro-3-pyridinecarboxamide (LC-MS/ELSD): (retention time: 0.71 minutes);
$^1$H-NMR (CDCl$_3$): δ 2.17-2.21, 2.52-2.62, 3.90-3.96, 4.02-4.09, 4.17-4.22, 5.10, 5.55-5.60, 7.10, 7.41-7.45, 7.54-7.59, 7.65, 7.82, 8.31, 8.77, 11.97.

Example 10(7)

N-[4-(4-amino-7-cyclopentyl-7H-pyrrolo[2,3-d]pyrimidin-5-yl)-3-methyl phenyl]-2-oxo-1-phenyl-1,2-dihydro-3-pyridinecarboxamide (LC-MS/ELSD): (retention time: 0.88 minutes);
$^1$H-NMR (CDCl$_3$): δ 1.44-1.82, 2.20-2.32, 4.78, 4.96-5.21, 6.61, 6.90, 7.55-7.80, 8.30, 8.76, 11.99.

Example 10(8)

N-[4-(4-amino-7-cyclopentyl-7H-pyrrolo[2,3-d]pyrimidin-5-yl)-3-fluorophenyl]-2-oxo-1-phenyl-1,2-dihydro-3-pyridinecarboxamide (LC-MS/ELSD): (retention time: 0.87 minutes);
$^1$H-NMR (CDCl$_3$): δ 1.72-1.96, 2.16-2.31, 4.98, 5.16-5.26, 6.62, 7.10, 7.35-7.44, 7.51-7.62, 7.65, 7.86, 8.32, 8.75, 12.06.

Example 10(9)

N-(4-{4-amino-7-[2-(4-methyl-1-piperazinyl)ethyl]-7H-pyrrolo[2,3-d]pyrimidin-5-yl}phenyl)-2-oxo-1-phenyl-1,2-dihydro-3-pyridinecarboxamide (LC-MS/ELSD): (retention time: 0.61 minutes);
$^1$H-NMR (CDCl$_3$): δ 2.30, 2.47, 2.60, 2.80, 4.33, 5.08, 6.62, 7.03, 7.41-7.43, 7.54-7.64, 7.65, 7.82, 8.31, 8.77, 11.96.

Example 10(10)

N-{4-[4-amino-7-(1,1-dioxide tetrahydro-2H-thiopyran-4-yl)-7H-pyrrolo[2,3-d]pyrimidin-5-yl]phenyl}-2-oxo-1-phenyl-1,2-dihydro-3-pyridinecarboxamide (LC-MS/ELSD): (retention time: 0.72 minutes);
$^1$H-NMR (DMSO-d$_6$): δ 2.23-2.26, 2.57-2.67, 3.16-3.19, 3.51-3.60, 5.00-5.06, 6.12, 6.73, 7.46-7.61, 7.79, 8.11, 8.16, 8.60, 12.03.

Example 10(11)

N-{4-[4-amino-7-(1-methyl-4-piperidinyl)-7H-pyrrolo[2,3-d]pyrimidin-5-yl]phenyl}-2-oxo-1-phenyl-1,2-dihydro-3-pyridinecarboxamide (LC-MS/ELSD): (retention time: 0.53 minutes);
$^1$H-NMR (CDCl$_3$): δ 2.01-2.17, 2.17-2.32, 2.36, 2.97-3.08, 4.68-4.81, 5.08, 6.61, 7.03, 7.42-7.45, 7.52-7.66, 7.82, 8.32, 8.77, 11.96.

Example 10(12)

N-{4-[4-amino-7-(1-methyl-4-piperidinyl)-7H-pyrrolo[2,3-d]pyrimidin-5-yl]phenyl}-1-(4-fluorophenyl)-2,5-dioxo-1,2,5,6,7,8-hexahydro-3-quinolinecarboxamide (LC-MS/ELSD): (retention time: 0.59 minutes);
$^1$H-NMR (CDCl$_3$): δ 2.09-2.19, 2.20-2.35, 2.37, 2.54-2.63, 3.03, 4.69-4.79, 5.11, 7.03, 7.27-7.37, 7.43, 7.78, 8.30, 9.33, 11.37.

Example 10(13)

N-{4-[4-amino-7-(2-oxaspiro[3.3]hept-6-yl)-7H-pyrrolo[2,3-d]pyrimidin-5-yl]phenyl}-2-oxo-1-phenyl-1,2-dihydro-3-pyridinecarboxamide (LC-MS/ELSD): (retention time: 0.72 minutes);
$^1$H-NMR (CDCl$_3$): δ 2.63-2.71, 2.89-2.96, 4.73, 4.86, 5.05-5.16, 6.17, 7.01, 7.41-7.44, 7.54-7.66, 7.81-7.83, 8.29, 8.77, 11.97.

Example 10(14)

N-{4-[4-amino-7-(2-methyl-2-azaspiro[3.3]hept-6-yl)-7H-pyrrolo[2,3-d]pyrimidin-5-yl]phenyl}-2-oxo-1-phenyl-1,2-dihydro-3-pyridinecarboxamide (LC-MS/ELSD): (retention time: 0.56 minutes);
$^1$H-NMR (CDCl$_3$): δ 2.37, 2.56-2.64, 2.77-2.82, 3.35, 3.46, 5.14-5.19, 6.61, 7.05, 7.41-7.44, 7.53-7.82, 7.82, 8.29, 8.75, 11.97.

Example 10(15)

N-{4-[4-amino-7-(1-methyl-4-piperidinyl)-7H-pyrrolo[2,3-d]pyrimidin-5-yl]phenyl}-4,6-dimethyl-2-oxo-1-phenyl-1,2-dihydro-3-pyridinecarboxamide (LC-MS/ELSD): (retention time: 0.55 minutes);
$^1$H-NMR (CDCl$_3$): δ 2.04, 2.07-2.20, 2.29-2.40, 2.43, 2.82, 3.01-3.18, 4.68-4.83, 5.11, 6.28, 7.01, 7.21-7.25, 7.38, 7.51-7.57, 7.57-7.64, 7.75, 8.29, 11.98.

Example 11

1-(4-chloro-5-iodo-7H-pyrrolo[2,3-d]pyrimidine-7-yl)-2-methyl-2-propanol

To a DMF solution (10.0 mL) of 4-chloro-5-iodo-7H-pyrrolo[2,3-d]pyrimidine (500 mg), cesium carbonate (1.7 g) and dimethyldioxirane (CAS registration No.: 74087-85-7) (0.2 mL) were added, and the mixture was stirred at 70° C. for three hours. The reaction solution was ice-cooled, and filtrated. The precipitate obtained by filtration was dried to obtain the title compound (460 mg) having the following physical property values.

$^1$H-NMR (CDCl$_3$): δ 1.23, 2.35, 4.25, 7.55, 8.60.

Example 12

N-{4-[4-amino-7-(2-hydroxy-2-methylpropyl)-7H-pyrrolo[2,3-d]pyrimidin-5-yl]phenyl}-2,5-dioxo-1-phenyl-1,2,5,6,7,8-hexahydro-3-quinolinecarboxamide

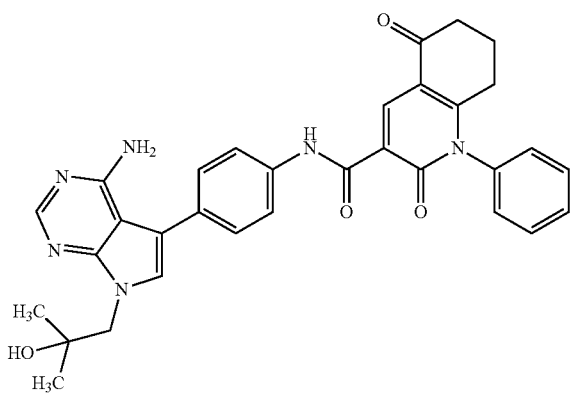 [SMILES: CC(C)(O)Cn1cc(-c2ccc(NC(=O)c3cc4c(n(-c5ccccc5)c3=O)CCCC4=O)cc2)c2c(N)ncnc21]

The compound produced in Example 11, 4-(4,4,5,5-tetramethyl-1,3,2-dioxaborolan-2-yl)aniline, and the compound produced in Example 5 were used and subjected to the procedure having the same object as in Example 2→Example 3→Example 6 to obtain the title compound (25 mg) having the following physical property values.

(LC-MS/ELSD): (retention time: 0.72 minutes);
$^1$H-NMR (CDCl$_3$): δ 1.24, 2.03-2.17, 2.49-2.64, 4.20, 5.16, 6.95, 7.28, 7.43, 7.55-7.68, 7.79, 8.28, 9.34, 11.44.

Example 12(1) to 12(22)

The compound produced in Example 11, 4-(4,4,5,5-tetramethyl-1,3,2-dioxaborolan-2-yl)aniline or the corresponding aniline derivative instead thereof, and the compound produced in Example 5 or the corresponding carboxylic acid derivative instead thereof were used and subjected to the procedure having the same object as in Example 12 to obtain the following compounds of Examples.

Example 12(1)

N-{4-[4-amino-7-(2-hydroxy-2-methylpropyl)-7H-pyrrolo[2,3-d]pyrimidin-5-yl]phenyl}-5-cyclopropyl-2-oxo-1-phenyl-1,2-dihydro-3-pyridinecarboxamide (LC-MS/ELSD): (retention time: 0.79 minutes);
$^1$H-NMR (CDCl$_3$): δ 0.69-0.75, 0.95-1.02, 1.19, 1.87-1.96, 4.20, 7.25, 7.45-7.63, 7.76-7.81, 8.13, 8.45.

Example 12(2)

N-{4-[4-amino-7-(2-hydroxy-2-methylpropyl)-7H-pyrrolo[2,3-d]pyrimidin-5-yl]-3-fluorophenyl}-2,5-dioxo-1-phenyl-1,2,5,6,7,8-hexahydro-3-quinolinecarboxamide (LC-MS/ELSD): (retention time: 0.77 minutes);
$^1$H-NMR (CDCl$_3$): δ 1.25, 2.06-2.17, 2.51-2.66, 4.21, 4.56, 5.05, 7.04, 7.27-7.30, 7.32-7.38, 7.42, 7.59-7.70, 7.83, 8.29, 9.33, 11.54.

Example 12(3)

N-{4-[4-amino-7-(2-hydroxy-2-methylpropyl)-7H-pyrrolo[2,3-d]pyrimidin-5-yl]-2-fluorophenyl}-2,5-dioxo-1-phenyl-1,2,5,6,7,8-hexahydro-3-quinolinecarboxamide (LC-MS/ELSD): (retention time: 0.77 minutes);
$^1$H-NMR (DMSO-d$_6$): δ 1.11, 1.95-2.40, 2.47-2.57, 4.40, 4.81, 6.17, 7.29-7.38, 7.45-7.49, 7.55-7.66, 8.13, 8.55, 8.97, 11.81.

Example 12(4)

N-{4-[4-amino-7-(2-hydroxy-2-methylpropyl)-7H-pyrrolo[2,3-d]pyrimidin-5-yl]-3-chlorophenyl}-2,5-dioxo-1-phenyl-1,2,5,6,7,8-hexahydro-3-quinolinecarboxamide (LC-MS/ELSD): (retention time: 0.74 minutes);
$^1$H-NMR (DMSO-d$_6$): δ 1.24, 2.05-2.14, 2.52-2.63, 4.21, 4.52, 4.92, 7.00, 7.25-7.28, 7.35, 7.59-7.69, 7.98, 8.28, 9.33, 11.41.

Example 12(5)

N-{4-[4-amino-7-(2-hydroxy-2-methylpropyl)-7H-pyrrolo[2,3-d]pyrimidin-5-yl]-3-methylphenyl}-2,5-dioxo-1-phenyl-1,2,5,6,7,8-hexahydro-3-quinolinecarboxamide (LC-MS/ELSD): (retention time: 0.72 minutes);
$^1$H-NMR (DMSO-d$_6$): δ 1.24, 2.04-2.17, 2.22, 2.49-2.68, 4.21, 4.61, 4.90, 6.84, 7.24-7.30, 7.56-7.72, 8.26, 9.34, 11.41.

Example 12(6)

N-{4-[4-amino-7-(2-hydroxy-2-methylpropyl)-7H-pyrrolo[2,3-d]pyrimidin-5-yl]-2-chlorophenyl}-2,5-dioxo-1-phenyl-1,2,5,6,7,8-hexahydro-3-quinolinecarboxamide (LC-MS/ELSD): (retention time: 0.75 minutes);
$^1$H-NMR (DMSO-d$_6$): δ 1.25, 2.04-2.15, 2.51-2.56, 2.57-2.65, 4.21, 5.17, 7.01, 7.27-7.30, 7.41, 7.50-7.52, 7.59-7.67, 8.29, 8.70, 9.34, 11.76.

Example 12(7)

N-{4-[4-amino-7-(2-hydroxy-2-methylpropyl)-7H-pyrrolo[2,3-d]pyrimidin-5-yl]phenyl}-2-oxo-1-phenyl-1,2-dihydro-3-pyridinecarboxamide trifluoroacetate (LC-MS/ELSD): (retention time: 0.63 minutes);
$^1$H-NMR (DMSO-d$_6$): δ 1.10, 4.18, 6.74, 7.45-7.49, 7.51-7.62, 7.84, 8.13, 8.39, 8.60, 12.08.

Example 12(8)

N-{4-[4-amino-7-(2-hydroxy-2-methylpropyl)-7H-pyrrolo[2,3-d]pyrimidin-5-yl]phenyl}-1-(3-fluorobenzyl)-2,5-dioxo-1,2,5,6,7,8-hexahydro-3-quinolinecarboxamide (LC-MS/ELSD): (retention time: 0.76 minutes);
$^1$H-NMR (CDCl$_3$): δ 1.26, 2.21-2.23, 2.60, 2.97, 4.21, 4.59, 5.15, 5.50, 6.86-6.97, 6.98, 7.01-7.10, 7.33-7.42, 7.47, 7.85, 8.29, 9.31, 11.59.

Example 12(9)

N-{4-[4-amino-7-(2-hydroxy-2-methylpropyl)-7H-pyrrolo[2,3-d]pyrimidin-5-yl]phenyl}-1-ethyl-2,5-dioxo-1,2,5,6,7,8-hexahydro-3-quinolinecarboxamide trifluoroacetate (LC-MS/ELSD): (retention time: 0.66 minutes);
$^1$H-NMR (DMSO-d$_6$): δ 1.10, 1.32, 2.14, 2.55, 3.19, 4.18, 4.21-4.30, 7.48, 7.52, 7.87, 8.40, 8.85, 11.81.

Example 12(10)

N-{4-[4-amino-7-(2-hydroxy-2-methylpropyl)-7H-pyrrolo[2,3-d]pyrimidin-5-yl]phenyl}-1-(4-fluorophenyl)-2,5-dioxo-1,2,5,6,7,8-hexahydro-3-quinolinecarboxamide (LC-MS/ELSD): (retention time: 0.68 minutes);
$^1$H-NMR (DMSO-d$_6$): δ 1.11, 1.96-2.12, 2.45-2.62, 4.14, 4.88, 6.13, 7.31, 7.46-7.62, 7.85, 8.17, 8.99, 11.54.

Example 12(11)

N-{4-[4-amino-7-(2-hydroxy-2-methylpropyl)-7H-pyrrolo[2,3-d]pyrimidin-5-yl]phenyl}-1-cyclobutyl-2,5-dioxo-1,2,5,6,7,8-hexahydro-3-quinolinecarboxamide (LC-MS/ELSD): (retention time: 0.68 minutes);
$^1$H-NMR (DMSO-d$_6$): δ 1.12, 1.71-1.98, 2.01-2.10, 2.39-2.58, 2.79-2.95, 3.08-3.20, 4.15, 4.89, 5.01, 6.14, 7.33, 7.50, 7.86, 8.17, 8.83, 11.68.

Example 12(12)

N-{4-[4-amino-7-(2-hydroxy-2-methylpropyl)-7H-pyrrolo[2,3-d]pyrimidin-5-yl]phenyl}-1-(cyclopropylmethyl)-2,5-dioxo-1,2,5,6,7,8-hexahydro-3-quinolinecarboxamide (LC-MS/ELSD): (retention time: 0.67 minutes);
$^1$H-NMR (DMSO-d$_6$): δ 0.46-0.63, 1.12, 2.11-2.25, 2.51-2.64, 3.29, 4.15, 4.24, 4.89, 6.15, 7.33, 7.50, 7.87, 8.17, 8.90, 11.79.

Example 12(13)

N-{4-[4-amino-7-(2-hydroxy-2-methylpropyl)-7H-pyrrolo[2,3-d]pyrimidin-5-yl]phenyl}-1-(3-hydroxy-3-methyl-2-butanyl)-2,5-dioxo-1,2,5,6,7,8-hexahydro-3-quinolinecarboxamide (LC-MS/ELSD): (retention time: 0.62 minutes);
$^1$H-NMR (DMSO-d$_6$): δ 1.12, 1.17, 1.63, 2.08-2.22, 2.45-2.64, 3.21-3.37, 4.15, 4.65, 4.89, 5.28, 6.15, 7.33, 7.50, 7.89, 8.17, 8.91, 11.53.

Example 12(14)

N-{4-[4-amino-7-(2-hydroxy-2-methylpropyl)-7H-pyrrolo[2,3-d]pyrimidin-5-yl]phenyl}-2',5'-dioxo-1'-phenyl-2',5',6',8'-tetrahydro-1'H-spiro[cyclobutane-1,7'-quinoline]-3'-carboxamide (LC-MS/ELSD): (retention time: 0.76 minutes);
$^1$H-NMR (DMSO-d$_6$): δ 1.11, 1.70-1.95, 2.71, 2.75, 4.14, 4.88, 6.13, 7.31, 7.48, 7.54-7.74, 7.84, 8.17, 8.95, 11.54.

Example 12(15)

N-{4-[4-amino-7-(2-hydroxy-2-methylpropyl)-7H-pyrrolo[2,3-d]pyrimidin-5-yl]phenyl}-1-(4,4-difluorocyclohexyl)-2,5-dioxo-1,2,5,6,7,8-hexahydro-3-quinolinecarboxamide (LC-MS/ELSD): (retention time: 0.72 minutes);
$^1$H-NMR (DMSO-d$_6$): δ 1.12, 1.83-1.99, 2.08-2.25, 2.44-2.62, 2.88-3.07, 3.11-3.25, 4.15, 4.58, 4.89, 6.14, 7.33, 7.49, 7.87, 8.17, 8.88, 11.65.

Example 12(16)

N-{4-[4-amino-7-(2-hydroxy-2-methylpropyl)-7H-pyrrolo[2,3-d]pyrimidin-5-yl]phenyl}-2,5-dioxo-1-(3-pentanyl)-1,2,5,6,7,8-hexahydro-3-quinolinecarboxamide (LC-MS/ELSD): (retention time: 0.73 minutes);
$^1$H-NMR (DMSO-d$_6$): δ 0.87, 1.12, 1.92-2.08, 2.09-2.22, 2.28-2.45, 2.50-2.61, 4.15, 4.44, 4.89, 6.14, 7.33, 7.50, 7.86, 8.17, 8.92, 11.75.

Example 12(17)

N-{4-[4-amino-7-(2-hydroxy-2-methylpropyl)-7H-pyrrolo[2,3-d]pyrimidin-5-yl]phenyl}-2,5-dioxo-1-(tetrahydro-2H-pyran-4-yl)-1,2,5,6,7,8-hexahydro-3-quinolinecarboxamide (LC-MS/ELSD): (retention time: 0.62 minutes);
$^1$H-NMR (DMSO-d$_6$): δ 1.12, 1.70-1.82, 2.08-2.22, 2.46-2.60, 2.86-3.09, 3.23-3.33, 3.47-3.60, 3.95-4.08, 4.15, 4.59-4.78, 4.89, 6.14, 7.33, 7.50, 7.88, 8.17, 8.88, 11.73.

Example 12(18)

N-{4-[4-amino-7-(2-hydroxy-2-methylpropyl)-7H-pyrrolo[2,3-d]pyrimidin-5-yl]phenyl}-6,6-dimethyl-2,5-dioxo-1-phenyl-1,2,5,6,7,8-hexahydro-3-quinolinecarboxamide (LC-MS/ELSD): (retention time: 0.77 minutes);
$^1$H-NMR (DMSO-d$_6$): δ 1.11, 1.18, 1.84-1.98, 2.45-2.60, 4.14, 4.88, 6.13, 7.31, 7.48, 7.56-7.70, 7.85, 8.17, 9.00, 11.60.

Example 12(19)

N-{4-[4-amino-7-(2-hydroxy-2-methylpropyl)-7H-pyrrolo[2,3-d]pyrimidin-5-yl]phenyl}-2,5-dioxo-1-phenyl-2,5,6,7,8,9-hexahydro-1H-cyclohepta[b]pyridine-3-carboxamide (LC-MS/ELSD): (retention time: 0.71 minutes);
$^1$H-NMR (DMSO-$d_6$): δ 1.11, 1.66-1.90, 2.62-2.81, 4.14, 4.87, 6.13, 7.31, 7.47, 7.52-7.71, 7.84, 8.16, 8.83, 11.66.

Example 12(20)

N-{4-[4-amino-7-(2-hydroxy-2-methylpropyl)-7H-pyrrolo[2,3-d]pyrimidin-5-yl]phenyl}-2',5'-dioxo-1'-phenyl-2',5',6',8'-tetrahydro-1'H-spiro[cyclopropane-1,7'-quinoline]-3'-carboxamide (LC-MS/ELSD): (retention time: 0.74 minutes);
$^1$H-NMR (DMSO-$d_6$): δ 0.39-0.49, 1.11, 2.47, 2.51, 4.14, 4.88, 6.12, 7.31, 7.47-7.69, 7.85, 8.17, 9.03, 11.56.

Example 12(21)

N-{4-[4-amino-7-(2-hydroxy-2-methylpropyl)-7H-pyrrolo[2,3-d]pyrimidin-5-yl]phenyl}-1-cyclopropyl-2,5-dioxo-1,2,5,6,7,8-hexahydro-3-quinolinecarboxamide trifluoroacetate (LC-MS/ELSD): (retention time: 0.66 minutes);
$^1$H-NMR (DMSO-$d_6$): δ 0.92-1.00, 1.10, 1.22-1.31, 2.09, 2.42-2.60, 3.10-3.21, 3.29, 4.17, 7.45-7.54, 7.86, 8.36, 8.79, 11.75.

Example 12(22)

N-{4-[4-amino-7-(2-hydroxy-2-methylpropyl)-7H-pyrrolo[2,3-d]pyrimidin-5-yl]phenyl}-1-(2-hydroxy-1-phenylethyl)-2,5-dioxo-1,2,5,6,7,8-hexahydro-3-quinolinecarboxamide (LC-MS/ELSD): (retention time: 0.67 minutes);
$^1$H-NMR (DMSO-$d_6$): δ 1.11, 2.10-2.28, 2.53-2.65, 3.17-3.58, 4.14, 4.42-4.53, 4.55-4.70, 4.88, 5.26-5.36, 5.74-5.90, 6.00-6.20, 7.28-7.52, 7.73-7.83, 8.16, 8.94, 11.45.

Example 13

3-(4-chloro-5-iodo-7H-pyrrolo[2,3-d]pyrimidine-7-yl)cyclopentanol

Cyclopentane 1,3-diol (CAS registration No.: 59719-74-3) and 4-chloro-5-iodo-7H-pyrrolo[2,3-d]pyrimidine instead of tert-butyl 4-hydroxypiperidine-1-carboxylate were used and subjected to the procedure having the same object as in Example 7 to obtain the title compound (530 mg) having the following physical property values.
$^1$H-NMR (CDCl$_3$): δ 1.75-1.82, 1.94-2.01, 2.16-2.21, 2.36-2.43, 4.25-4.29, 4.98, 5.26-5.30, 8.14, 8.63.

Example 14

4-chloro-7-(3-fluorocyclopentyl)-5-iodo-7H-pyrrolo[2,3-d]pyrimidine

Bis(2-methoxyethyl)aminosulfur trifluoride (0.3 mL) was added to a dichloromethane solution (25 mL) of the compound produced in Example 13 (470 mg) at −5° C. The resulting mixture was stirred at room temperature for two hours. To the reaction solution, a saturated aqueous solution of sodium hydrogen carbonate was added. The organic layer was extracted with dichloromethane. The resulting organic layer was dried over sodium sulfate, and filtrated. Thereafter, the solvent was removed by evaporation by concentration under reduced pressure. The obtained residue was purified by column chromatography on silica gel (hexane:ethyl acetate=100:0→100:40) to obtain the title compound (368 mg) having the following physical property values.
$^1$H-NMR (CDCl$_3$): δ 1.98-2.06, 2.09-2.43, 2.45-2.53, 2.53-2.64, 5.28-5.32, 5.35-5.44, 7.38, 8.61.

Example 15

N-{5-[4-amino-7-(3-fluorocyclopentyl)-7H-pyrrolo[2,3-d]pyrimidin-5-yl]-2-pyridinyl}-2,5-dioxo-1-phenyl-1,2,5,6,7,8-hexahydro-3-quinolinecarboxamide The compound produced in Example 14, 5-(4,4,5,5-tetramethyl-1,3,2-dioxaborolan-2-yl)pyridine-2-amine, and the compound produced in Example 5 were used and subjected to the procedure having the same object as in Example 2→Example 6→Example 3 to obtain the title compound (7.3 mg) having the following physical property values.
TLC: Rf 0.39 (ethyl acetate);
$^1$H-NMR (CDCl$_3$): δ 2.08, 2.22-2.51, 2.63, 5.21, 5.43, 6.96, 7.24, 7.60, 7.80, 8.29, 8.38, 8.44, 9.31, 11.90.

Example 15(1)

N-{4-[4-amino-7-(3-fluorocyclopentyl)-7H-pyrrolo[2,3-d]pyrimidin-5-yl]phenyl}-2-oxo-1-phenyl-1,2-dihydro-3-pyridinecarboxamide The compound produced in Example 14, 4-(4,4,5,5-tetramethyl-1,3,2-dioxaborolan-2-yl)aniline, and the corresponding carboxylic acid derivative instead of the compound produced in Example 5 were used and subjected to the procedure having the same object as in Example 15 to obtain the title compound having the following physical property values.
(LC-MS/ELSD): (retention time: 4.15 minutes);
$^1$H-NMR (DMSO-$d_6$): δ 1.88-2.01, 2.24-2.43, 5.23-5.43, 6.28, 6.72, 7.44-7.60, 7.79, 8.11, 8.13, 8.59, 12.03.

Example 16

N-[4-(4-amino-7-((2-(trimethylsilyl)ethoxy)methyl)7H-pyrrolo[2,3-d]pyrimidin-5-yl)phenyl]-2,5-dioxo-1-phenyl-1,2,5,6,7,8-hexahydro-3-quinolinecarboxamide 5-(4-aminophenyl)-7-((2-(trimethylsilyl)ethoxy)methyl)-7H-pyrrolo[2,3-d]pyrimidine-4-amine instead of the compound produced in Example 3 and the compound produced in Example 5 were used and subjected to the procedure having the same object as in Example 6 to obtain the title compound (178 mg) having the following physical property values.
TLC: Rf 0.63 (ethyl acetate:methanol=5:1);
$^1$H-NMR (CDCl$_3$): δ −0.03, 0.93, 2.11, 2.59, 3.57, 5.10, 5.59, 7.07, 7.27, 7.44, 7.64, 7.78, 8.32, 9.33, 11.43.

Example 17

N-[4-(4-amino-7H-pyrrolo[2,3-d]pyrimidin-5-yl)phenyl]-2,5-dioxo-1-phenyl-1,2,5,6,7,8-hexahydro-3-quinolinecarboxamide Under argon atmosphere, trifluoroacetic acid (0.5 mL) was added to a dichloromethane solution (2 mL) of the compound (150 mg) produced in Example 16. The resulting mixture was stirred at room temperature for three hours. Thereafter, the solvent was removed by evaporation under reduced pressure. 28% ammonia water (2 mL) was added thereto, and the resulting mixture was stirred at room temperature for three hours. The solvent was removed by evaporation under reduced pressure. The obtained residue was purified by column chromatography on silica gel (ethyl acetate→ethyl acetate:methanol=7:3) to obtain the title compound (81.9 mg) having the following physical property values.

TLC: Rf 0.63 (ethyl acetate:methanol=5:1);
$^1$H-NMR (DMSO-$d_6$): δ 1.98, 2.45, 6.00, 7.21, 7.44, 7.64, 7.78, 8.08, 8.94, 11.50, 11.75.

Example 18 ethyl 3-amino-3-oxopropanoate

Aniline (3.1 g), 4-dimethylaminopyridine (0.61 g), triethylamine (5.1 mL), and dichloromethane (25 mL) were added into a 300-mL 3-diameter eggplant flask, and, then, a dichloromethane solution (25 mL) of ethyl malonyl chloride (5.0 g) was dropped over 20 minutes. The resulting solution was stirred as it is for 30 minutes, and then water was added thereto, and dichloromethane removed by evaporation under reduced pressure. The residue was extracted with ethyl acetate, and then washed with 1N hydrochloric acid and saturated saline solution sequentially in this order, and dried over anhydrous sodium sulfate. Thereafter, the solvent was removed by evaporation under reduced pressure. The obtained residue was purified by column chromatography on silica gel (hexane:ethyl acetate=7:3→1:1) to obtain the title compound (5.8 g) having the following physical property values.

TLC: Rf 0.50 (hexane:ethyl acetate=1:1);
$^1$H-NMR (CDCl$_3$): δ 1.32, 3.47, 4.26, 7.13, 7.35, 7.55, 9.22.

Example 19

6-methyl-2-oxo-1-phenyl-1,2-dihydro-3-pyridinecarboxylic acid

The compound (5.8 g) produced in Example 18, (E)-4-methoxy-3-buten-2-one (3.1 g), 20% sodium ethoxide ethanol solution (11.4 g), and methanol (30 mL) were added into a 200-mL eggplant flask. The mixture was heated and refluxed for 16 hours, and then allowed to cool to room temperature. The solvent was removed by evaporation under reduced pressure. Then, 2N sodium hydroxide aqueous solution (30 mL) and methanol (30 mL) were added to the obtained residue. The resulting solution was stirred at room temperature for 23 hours. Water was added to the reaction solution, washed with ethyl acetate, and made the water layer to pH=3 to 4 with 5N hydrochloric acid. The precipitated powder was collected by filtration, and dried to obtain the title compound (3.0 g) having the following physical property values.

TLC: Rf 0.60 (ethyl acetate:methanol=9:1);
$^1$H-NMR (DMSO-$d_6$): δ 2.15, 6.54, 7.24, 7.63, 8.51, 14.0.

Example 20 methyl 6-methyl-2-oxo-1-phenyl-1,2-dihydro-3-pyridinecarboxylate

The compound (2.9 g) produced in Example 19, methanol (29 mL), ethyl acetate (29 mL), and trimethylsilyl diazomethane were added into a 200-mL eggplant flask. The solvent was removed by evaporation under reduced pressure to obtain the title compound (2.9 g) having the following physical property values.

TLC: Rf 0.34 (ethyl acetate);
$^1$H-NMR (CDCl$_3$): δ 2.04, 3.88, 6.22, 7.18, 7.50, 8.20.

Example 21 methyl 5-bromo-6-(bromomethyl)-2-oxo-1-phenyl-1,2-dihydro-3-pyridine carboxylate The compound (2 g) produced in Example 20, N-bromosuccinimide (3.1 g), benzoyl peroxide (40 mg), and carbon tetrachloride (36 mL) were added into a 100-mL eggplant flask. The resulting mixture was heated at 80° C. for six hours. The temperature was returned to room temperature. Then, precipitate was removed from the reaction solution, the solvent was removed by evaporation under reduced pressure. The resultant residue was washed with a small amount of ethyl acetate and hexane to obtain the title compound (2.9 g) having the following physical property values.

TLC: Rf 0.29 (hexane:ethyl acetate=1:1);
$^1$H-NMR (CDCl$_3$): δ 3.89, 4.14, 7.29, 7.54, 8.33.

Example 22 methyl 6-[(bis{[(2-methyl-2-propanyl)oxy]carbonyl}amino)methyl]-5-bromo-2-oxo-1-phenyl-1,2-dihydro-3-pyridine carboxylate The compound (2.5 g) produced in Example 21, di-tert-butyl imidodicarbonate (Boc$_2$NH) (1.6 g), potassium carbonate (1.7 g), and DMF (30 mL) were added into a 100-mL eggplant flask. The mixture was stirred at room temperature for four hours, and a saturated aqueous solution of ammonium chloride was added, extracted with ethyl acetate, washed with water and then a saturated saline solution, and dried over anhydrous sodium sulfate. Thus, the solvent was removed by evaporation under reduced pressure. The resulting product was purified by column chromatography on silica gel (hexane:ethyl acetate=7:3→1:1) to obtain the title compound (2.9 g) having the following physical property values.

TLC: Rf 0.40 (hexane:ethyl acetate=1:1);
$^1$H-NMR (CDCl$_3$): δ 1.40, 3.88, 4.67, 7.20, 7.47, 8.34.

Example 23

6-[(bis{[(2-methyl-2-propanyl)oxy]carbonyl}amino)methyl]-5-bromo-2-oxo-1-phenyl-1,2-dihydro-3-pyridinecarboxylic acid The compound (2.9 g) produced in Example 22, 2N sodium hydroxide aqueous solution (14 mL), and methanol (14 mL) were added into a 100-mL eggplant flask. The mixture was stirred for 30 minutes. To the reaction solution, 1N hydrochloric acid was added. The precipitated powder was collected by filtration and dried to obtain the title compound (2.3 g) having the following physical property values.

TLC: Rf 0.57 (ethyl acetate);
$^1$H-NMR (CDCl$_3$): δ 1.42, 4.69, 7.26, 7.59, 8.67, 13.77.

Example 24 bis(2-methyl-2-propanyl) [(5-{[4-(4-amino-7-methyl-7H-pyrrolo[2,3-d]pyrimidin-5-yl)phenyl]carbamoyl}-3-bromo-6-oxo-1-phenyl-1,6-dihydro-2-pyridinyl)methyl]imidodicarbonate Under argon atmosphere, to the compound (656 mg) produced in Example 3 using 4-chloro-5-iodo-7-methyl-7H-pyrrolo[2,3-d]pyrimidine and 4-(4,4,5,5-tetramethyl-1,3,2-dioxaborolan-2-yl)aniline and a DMF solution (3 mL) of the compound (300 mg) produced in Example 23, HATU (620 mg) and DIPEA (0.54 mL) were added. The mixture was stirred at room temperature for one hour. A sodium bicarbonate aqueous solution was added to the reaction solution, followed by extraction with ethyl acetate. The organic layer was washed with a saturated saline solution, then dried over anhydrous sodium sulfate, and concentrated to obtain the title compound (850 mg) having the following physical property values.
TLC: Rf 0.25 (hexane:ethyl acetate=3:7);
$^1$H-NMR (CDCl$_3$): δ 1.43, 3.83, 5.07, 6.91, 7.23-7.34, 7.41, 7.51-7.64, 7.77, 8.33, 8.80.

Example 25

6-(aminomethyl)-N-[4-(4-amino-7-methyl-7H-pyrrolo[2,3-d]pyrimidin-5-yl)phenyl]-2-oxo-1-phenyl-1,2-dihydro-3-pyridinecarboxamide Under argon atmosphere, a THF:ethanol:DMF (100 mL, 1:1:1) solution of the compound (850 mg) produced in Example 24, 5M hydrochloric acid (20 mL), and palladium hydroxide (1.4 g) were added. The mixture was stirred at 50° C. for six hours under hydrogen atmosphere. The reaction solution was filtered through celite, and the solvent was removed by evaporation under reduced pressure. The residue was washed with ethyl acetate to obtain title compound (340 mg) having the following physical property values.
TLC: Rf 0.15 (ethyl acetate:methanol=8:2);
$^1$H-NMR (DMSO-d$_6$): δ 3.62, 3.82, 6.95, 7.40, 7.45, 7.60-7.86, 8.62, 8.88, 11.87.

Example 26

N-[4-(4-amino-7-methyl-7H-pyrrolo[2,3-d]pyrimidine-5-yl)phenyl]-6-[(2-butynoylamino)methyl]-2-oxo-1-phenyl-1,2-dihydro-3-pyridinecarboxamide

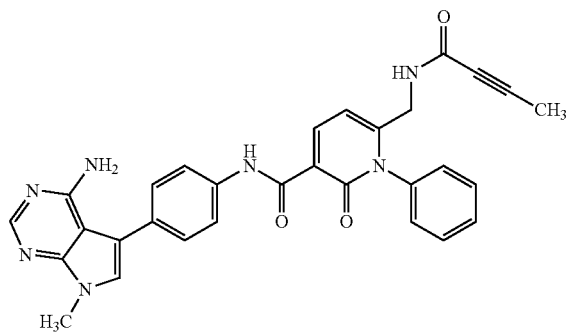 [SMILES: CC#CC(=O)NCc1ccc(C(=O)Nc2ccc(-c3cn(C)c4ncnc(N)c34)cc2)c(=O)n1-c1ccccc1]

Under argon atmosphere, 2-butynoate (0.034 mL), HATU (159 mg), DIPEA (0.14 mL) were added to a DMF solution (1.5 mL) of the compound (150 mg) produced in Example 25, and the mixture was stirred at room temperature for two hours. A sodium dicarbonate aqueous solution was added to the reaction solution, followed by extraction with ethyl acetate. The organic layer was washed with a saturated saline solution, then dried over anhydrous sodium sulfate, and concentrated. The resulting product was purified by column chromatography on silica gel (ethyl acetate:methanol=100:0→80:20, NH silica) to obtain the title compound (23 mg) having the following physical property values.
TLC: Rf 0.25 (ethyl acetate:methanol=9:1);
$^1$H-NMR (DMSO-d$_6$): δ 1.98, 3.71, 3.82, 6.05, 6.57, 7.27, 7.40, 7.60, 7.75, 8.12, 8.57, 9.10, 11.88.

Example 27

3-bromo-1-phenyl-5-(trifluoromethyl)-2(1H)-pyridinone 3-bromo-5-(trifluoromethyl)pyridin-2(1H)-one (1.0 g), phenylboric acid (1.1 g), diacetoxy copper (II) (1.5 g), pyridine (5.0 mL) and 4 Å molecular sieves (1.0 g) were added to dichloromethane (30 mL). The mixture was stirred at room temperature for 16 hours under oxygen atmosphere. The reaction solution was filtered through celite to remove insoluble solid, followed by dilution by adding dichloromethane (30 mL). The organic layer was rinsed with water (3×10 mL). The obtained organic layer was dried over sodium sulfate, and filtered. Thereafter, the solvent was distilled off by concentration under reduced pressure. The obtained residue was purified by column chromatography on silica gel (hexane:ethyl acetate=100:0→25:75) to obtain the title compound (1.1 g) having the following physical property values.
$^1$H-NMR (CDCl$_3$): δ 7.36-7.39, 7.48-7.53, 7.75-7.77, 7.94.

Example 28 methyl 2-oxo-1-phenyl-5-(trifluoromethyl)-1,2-dihydro-3-pyridinecarboxylate

The compound (250 mg) produced in Example 27 was dissolved in a mixed solvent of DMF (8.0 mL) and methanol (8.0 mL), the inside of the reaction container was subjected to deaeration under nitrogen atmosphere for ten minutes. Palladium acetate (II) (36 mg), 1,1'-bis(diphenylphosphino)ferrocene (88 mg) and triethylamine (0.33 mL) were added thereto. The mixture was stirred under carbon monoxide atmosphere (100 psi) at 90° C. for 16 hours. The reaction solution was filtered through celite to remove insoluble solid, followed by dilution with dichloromethane. The resulting solution was washed with 10% citric acid aqueous solution. The resulting organic layer was dried over sodium sulfate, and subjected to filtration. Then, the solvent was distilled off by concentration under reduced pressure to obtain the title compound (140 mg) having the following physical property values. The obtained compound was used for the subsequent reaction without purification.
$^1$H-NMR (CDCl$_3$): δ 3.39, 7.33-7.41, 7.45-7.58, 7.93-7.97, 8.35.

Example 29

2-oxo-1-phenyl-5-(trifluoromethyl)-1,2-dihydro-3-pyridine carboxylic acid

The compound (100 mg) produced in Example 28 was dissolved in THF (2 mL), and sodium trimethylsilanolate (38 mg) was added thereto. The mixture was stirred at room temperature for three hours. The reaction solution was filtrated and the obtained precipitate was washed with THF to obtain the title compound (45 mg) having the following physical property value. The obtained compound was used for the subsequent reaction without purification.

MS (M+H): 284.

Example 30

N-[4-(4-amino-7-methyl-7H-pyrrolo[2,3-d]pyrimidin-5-yl)phenyl]-2-oxo-1-phenyl-5-(trifluoromethyl)-1,2-dihydro-3-pyridinecarboxamide trifluoroacetate

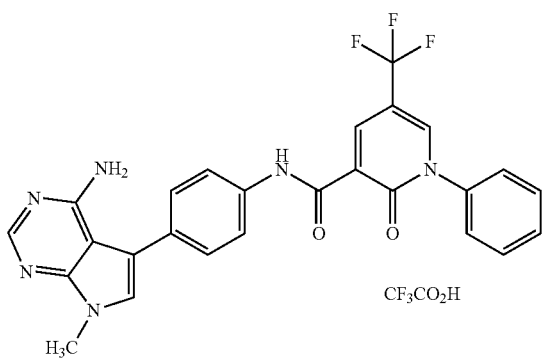 [SMILES: Cn1cc(-c2ccc(NC(=O)c3cc(C(F)(F)F)cn(-c4ccccc4)c3=O)cc2)c2c(N)ncnc21 ; "CF3CO2H"]

The compound (21 mg) produced in Example 3 and the compound (25 mg) produced in Example 29 were used and subjected to the procedure having the same object as in Example 6, and purified by reverse-phase chromatography (a mixed solvent of trifluoroacetic acid and acetonitrile) to obtain the title compound (40 mg) having the following physical property values.

(LC-MS/ELSD): (retention time: 0.83 minutes);
$^1$H-NMR (DMSO-$d_6$): δ 3.83, 7.44-7.49, 7.57-7.62, 7.85, 8.41, 8.63, 8.76-8.79, 11.67.

Example 30(1) to 30(6)

4-chloro-5-iodo-7-methyl-7H-pyrrolo[2,3-d]pyrimidine, 4-(4,4,5,5-tetramethyl-1,3,2-dioxaborolan-2-yl)aniline or the corresponding boronic acid derivative instead thereof, and the corresponding carboxylic acid derivative instead of the compound produced in Example 29 were used and subjected to the procedure having the same object as in Example 2→Example 6→Example 3 to obtain the following compounds of Examples.

Example 30(1)

N-[4-(4-amino-7-methyl-7H-pyrrolo[2,3-d]pyrimidin-5-yl)phenyl]-2-oxo-1-[(1S)-1-phenylethyl]-1,2-dihydro-3-pyridinecarboxamide (LC-MS/ELSD): (retention time: 0.79 minutes);
$^1$H-NMR (CDCl$_3$): δ 1.18, 3.84, 5.10, 6.45, 6.55, 6.94, 7.31-7.38, 7.39-7.44, 7.46, 7.86, 8.35, 8.61, 12.20.

Example 30(2)

N-[5-(4-amino-7-methyl-7H-pyrrolo[2,3-d]pyrimidin-5-yl)-2-pyridinyl]-2-oxo-1-[(1S)-1-phenylethyl]-1,2-dihydro-3-pyridinecarboxamide (LC-MS/ELSD): (retention time: 0.75 minutes);
$^1$H-NMR (CDCl$_3$): δ 1.80, 3.86, 5.01, 6.43, 6.58, 6.98, 7.32-7.46, 7.83, 8.36, 8.45, 8.51, 8.58, 12.72.

Example 30(3)

N-{5-[4-amino-7-(2-hydroxy-2-methylpropyl)-7H-pyrrolo[2,3-d]pyrimidin-5-yl]-2-pyridinyl}-5-cyclopropyl-2-oxo-1-phenyl-1,2-dihydro-3-pyridinecarboxamide (LC-MS/ELSD): (retention time: 0.76 minutes);
$^1$H-NMR (CDCl$_3$): δ 0.66-0.71, 0.94-1.00, 1.25, 1.77-1.86, 4.21, 4.38, 5.06, 7.01, 7.39-7.57, 7.82, 8.30, 8.41-8.45, 8.51, 12.54.

Example 30(4)

N-[4-(4-amino-7-methyl-7H-pyrrolo[2,3-d]pyrimidin-5-yl)phenyl]-5-cyclopropyl-2-oxo-1-[(1S)-1-phenylethyl]-1,2-dihydro-3-pyridinecarboxamide (LC-MS/ELSD): (retention time: 0.89 minutes);
$^1$H-NMR (CDCl$_3$): δ 0.53-0.59, 0.84-0.92, 1.65-1.70, 1.80, 3.84, 5.09, 6.55, 6.94, 7.23, 7.32-7.43, 7.46, 7.86, 8.34, 8.35, 12.33.

Example 30(5)

N-[5-(4-amino-7-methyl-7H-pyrrolo[2,3-d]pyrimidin-5-yl)-2-pyridinyl]-5-cyclopropyl-2-oxo-1-[(1S)-1-phenylethyl]-1,2-dihydro-3-pyridinecarboxamide (LC-MS/ELSD): (retention time: 0.89 minutes);
$^1$H-NMR (CDCl$_3$): δ 0.52-0.59, 0.85-0.91, 1.64-1.72, 1.79, 3.86, 5.00, 6.58, 6.99, 7.25, 7.34-7.44, 7.83, 8.31, 8.37, 8.45, 8.51, 12.86.

Example 30(6)

N-[4-(4-amino-7-methyl-7H-pyrrolo[2,3-d]pyrimidin-5-yl)phenyl]-1-(3-fluorobenzyl)-2-oxo-1,2-dihydro-3-pyridinecarboxamide (LC-MS/ELSD): (retention time: 0.75 minutes);
$^1$H-NMR (CDCl$_3$): δ 3.84, 5.09, 5.27, 6.53, 6.93, 7.07, 7.36, 7.46, 7.59, 7.84, 8.34, 8.67, 12.02.

Example 31

N-[4-(4-amino-7-methyl-7H-pyrrolo[2,3-d]pyrimidin-5-yl)phenyl]-5-hydroxy-2-oxo-1-phenyl-1,2,5,6,7,8-hexahydro-3-quinolinecarboxamide The compound (100 mg) produced in Example 6 was dissolved in THF (10 mL), and 1 mol/L THF solution (0.45 mL) of lithium aluminum hydride was added thereto while the mixture was stirred at 0° C. for three hours. Thereafter, the reaction solution stirred at room temperature for 16 hours. An aqueous solution of sodium tartrate was added to the reaction solution, and the water layer was extracted with 10% methanol containing dichloromethane solution three times. The resulting organic layer was dried over sodium sulfate, and filtrated. Thereafter, the solvent was distilled off by concentration under reduced pressure. The obtained residue was washed with acetonitrile and methanol to obtain the title compound (11 mg) having the following physical property values.

(LC-MS/ELSD): (retention time: 0.70 minutes);
$^1$H-NMR (CDCl$_3$): δ 1.69-1.79, 1.85-1.92, 2.17-2.27, 3.83, 4.85, 5.08, 6.90, 7.19-7.40, 7.41, 7.57-7.62, 7.79, 8.33, 8.81, 11.85.

Example 32

N-[4-(4-amino-7-methyl-7H-pyrrolo[2,3-d]pyrimidin-5-yl)phenyl]-2-oxo-1-phenyl-1,2-dihydro-3-quinolinecarboxamide

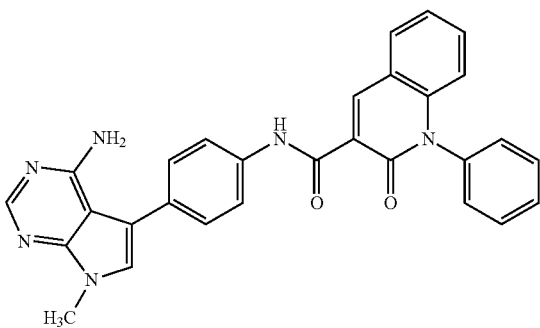 [SMILES: Cn1cc(-c2ccc(NC(=O)c3cc4ccccc4n(-c4ccccc4)c3=O)cc2)c2c(N)ncnc21]

The compound produced in Example 3, phenylboric acid, and ethyl 2-oxo-1,2-dihydroquinoline-3-carboxylate (CAS registration No.: 85870-47-9) instead of 3-bromo-5-(trifluoromethyl)pyridin-2(1H)-one were used and subjected to the procedure having the same object as in Example 27→Example 23→Example 6 to obtain the title compound (39 mg) having the following physical property values.

(LC-MS/ELSD): (retention time: 0.84 minutes);
$^1$H-NMR (CDCl$_3$): δ 3.73, 6.07, 6.63, 7.30, 7.39-7.48, 7.60-7.71, 7.84, 8.15, 8.17, 9.15, 11.98.

Example 33 methyl 2-oxo-1,2,5,6,7,8-hexahydro-3-quinolinecarboxylate

To a methanol solution (10 mL) of 2-oxo-1,2,5,6,7,8-hexahydroquinoline-3-carboxylic acid (CAS registration No.: 64500-54-5) (1.0 g), thionyl chloride (0.8 mL) was added. The mixture was stirred at 0° C. for 10 minutes. The temperature was returned to room temperature and the mixture was stirred overnight. The solvent was removed by evaporation under reduced pressure. The resultant product was diluted with a saturated mixed solution of sodium hydrogen carbonate and ethyl acetate (1:1), and the resulting organic layer was dried over sodium sulfate. After filtration and concentration thereof, the title compound (0.75 g) having the having the following physical property values was obtained.

$^1$H-NMR (DMSO-d$_6$): δ 1.65-1.67, 2.42-2.54, 3.27-3.29, 3.71, 7.82, 11.79.

Example 34

N-[4-(4-amino-7-methyl-7H-pyrrolo[2,3-d]pyrimidin-5-yl)phenyl]-2-oxo-1-phenyl-1,2,5,6,7,8-hexahydro-3-quinolinecarboxamide The compound produced in Example 33 was subjected to the same procedure as in Example 32 to obtain the title compound (30 mg) having the following physical property values.

(LC-MS/ELSD): (retention time: 0.84 minutes);
$^1$H-NMR (CDCl$_3$): δ 1.77-1.81, 2.23, 2.72, 3.83, 5.08, 6.90, 7.39-7.42, 7.59, 7.58-7.61, 7.79, 8.33, 8.51, 12.00.

Example 35 ethyl 2-oxo-1,2-dihydro-1,8-naphthyridine-3-carboxylate 2-amino-3-formylpyridine (CAS registration No.: 7521-41-7) (1.0 g) was dissolved in ethanol (20 mL), and diethyl malonate (3.4 mL), piperidine (2.4 mL), and acetic acid (0.052 mL) were added thereto. The resulting mixture was refluxed for 18 hours. The reaction solution was left to cool to room temperature, and then the solvent was distilled off by concentration under reduced pressure. The obtained residue was washed with water to obtain the title compound (1.5 g) having the following physical property value.
$^1$H-NMR (CDCl$_3$): δ 1.43, 4.45, 7.26-7.29, 8.04, 8.47, 8.87, 12.24.

Example 36 ethyl 2-oxo-1-phenyl-1,2-dihydro-1,8-naphthyridine-3-carboxylate

The compound produced in Example 35 was subjected to the procedure having the same object as in Example 27 to obtain the title compound (540 mg) having the following physical property values.
$^1$H-NMR (CDCl$_3$): δ 1.40, 4.42, 7.20, 7.27-7.28, 7.47-7.51, 7.54-7.59, 8.02, 8.47, 8.53.

Example 37

2-oxo-1-phenyl-1,2-dihydro-1,8-naphthyridine-3-carboxylic acid

The compound produced in Example 36 was subjected to the procedure having the same object as in Example 23 to obtain the title compound (400 mg) having the following physical property value.
MS (M+H): 267

Example 38

N-[4-(4-amino-7-methyl-7H-pyrrolo[2,3-d]pyrimidin-5-yl)phenyl]-2-oxo-1-phenyl-1,2-dihydro-1,8-naphthyridine-3-carboxamide The compound produced in Example 3 and the compound produced in Example 37 were used and subjected to the same procedure as in Example 6 to obtain the title compound (100 mg) having the following physical property values.

(LC-MS/ELSD): (retention time: 0.73 minutes);

$^1$H-NMR (CDCl$_3$): δ 3.83, 5.09, 6.93, 7.31-7.35, 7.46, 7.68-7.57, 7.83, 8.21, 8.34, 8.62, 9.14, 11.85.

Example 38(1)

N-{4-[4-amino-7-(2-hydroxy-2-methylpropyl)-7H-pyrrolo[2,3-d]pyrimidin-5-yl]phenyl}-2-oxo-1-phenyl-1,2-dihydro-1,8-naphthyridine-3-carboxamide The compound produced in Example 37, the compound produced in Example 11, and 4-(4,4,5,5-tetramethyl-1,3,2-dioxaborolan-2-yl)aniline were used and subjected to the same procedure as in Example 2→Example 3→Example 6 to obtain the title compound having the following physical property values.
(LC-MS/ELSD): (retention time: 0.73 minutes);
$^1$H-NMR (CDCl$_3$): δ 1.25, 4.21, 4.55, 5.15, 6.97, 7.32-7.35, 7.47, 7.57-7.68, 7.84, 8.20, 8.29, 8.61, 9.14, 11.86.

Example 39

N-[4-(4-amino-7-methyl-7H-pyrrolo[2,3-d]pyrimidin-5-yl)phenyl]-2-oxo-1-phenyl-1,2-dihydro-1,6-naphthyridine-3-carboxamide The compound produced in Example 3 and 4-amino-3-formylpyridine instead of 2-amino-3-formylpyridine were used and subjected to the procedure having the same object as in Example 35→Example 27→Example 23→Example 6 to obtain the title compound (45 mg) having the following physical property values.
(LC-MS/ELSD): (retention time: 0.69 minutes);
$^1$H-NMR (CDCl$_3$): δ 3.84, 5.08, 6.63, 6.93, 7.34, 7.46, 7.64-7.73, 7.82, 8.34, 8.55, 9.10, 9.24, 11.65.

Example 39(1)

N-{4-[4-amino-7-(2-hydroxy-2-methylpropyl)-7H-pyrrolo[2,3-d]pyrimidin-5-yl]phenyl}-2-oxo-1-phenyl-1,2-dihydro-1,6-naphthyridine-3-carboxamide The compound produced in Example 39, the compound produced in Example 11, and 4-(4,4,5,5-tetramethyl-1,3,2-dioxaborolan-2-yl)aniline were used and subjected to the same procedure as in Example 2→Example 3→Example 6 to obtain the title compound having the following physical property values.
(LC-MS/ELSD): (retention time: 0.68 minutes);
$^1$H-NMR (DMSO-d$_6$): δ 1.08, 4.12, 4.85, 6.12, 6.54, 7.29, 7.46-7.53, 7.62-7.73, 7.86, 8.14, 8.55, 9.24, 9.31, 11.69.

Example 40

4-chloro-7-{cis-3-[(benzyloxy)methyl]cyclobutyl}-5-iodo-7H-pyrrolo[2,3-d]pyrimidine Trans-3-benzyloxymethylcyclobutanol instead of tert-butyl 4-hydroxypiperidine-1-carboxylate was used and subjected to the same procedure as in Example 7 to obtain the title compound (65 mg) having the following physical property values.

$^1$H-NMR (CDCl$_3$): δ 2.33-2.54, 2.62-2.70, 3.54, 4.58, 5.15-5.43, 7.29-7.41, 7.61, 8.58.

Example 41

N-[4-(4-amino-7-{cis-3-[(benzyloxy)methyl]cyclobutyl}-7H-pyrrolo[2,3-d]pyrimidin-5-yl)phenyl]-2,5-dioxo-1-phenyl-1,2,5,6,7,8-hexahydro-3-quinolinecarboxamide The compound produced in Example 40, 4-(4,4,5,5-tetramethyl-1,3,2-dioxaborolan-2-yl)aniline, and the compound produced in Example 5 were used and subjected to the same procedure as in Example 2→Example 3→Example 6 to obtain the title compound (110 mg) having the following physical property values.
$^1$H-NMR (CDCl$_3$): δ 2.04-2.12, 2.28-2.68, 3.54, 4.55, 5.06, 5.16-5.29, 7.14, 7.29-7.36, 7.40, 7.61-7.69, 7.78, 8.29, 9.34, 11.43.

Example 42

N-[4-{4-amino-7-[cis-3-(hydroxymethyl)cyclobutyl]-7H-pyrrolo[2,3-d]pyrimidin-5-yl}phenyl)-2,5-dioxo-1-phenyl-1,2,5,6,7,8-hexahydro-3-quinolinecarboxamide

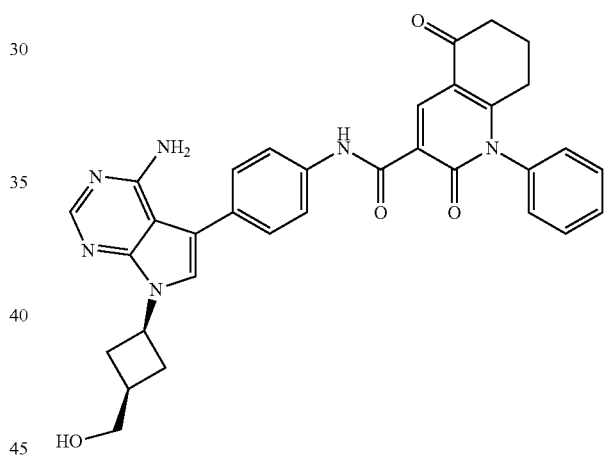

The compound produced in Example 41 (110 mg) was suspended in water (0.1 mL), and hydrobromic acid (5.0 mL) was added thereto. The resulting mixture was stirred at room temperature for four hours. Ethyl acetate was added to the reaction solution, and then an aqueous solution of sodium carbonate was added to the reaction solution, and the reaction solution was neutralized. The water layer was extracted with ethyl acetate, and then the resulting organic layer was dried over sodium sulfate. After filtration, the solvent was distilled off by concentration under reduced pressure to obtain the title compound (60 mg) having the following physical property values.
(LC-MS/ELSD): (retention time: 0.71 minutes);
$^1$H-NMR (CDCl$_3$): δ 2.07-2.15, 2.46-2.66, 3.74, 4.13, 5.04-5.15, 5.09, 7.06, 7.27-7.31, 7.42, 7.60-7.69, 7.79, 8.30, 9.34, 11.45.

Example 42(1) to 42(4)

The compound produced in Example 40, 4-(4,4,5,5-tetramethyl-1,3,2-dioxaborolan-2-yl)aniline, and the corresponding carboxylic acid derivative instead of the compound produced in Example 5 were used and subjected to the procedure having the same object as in Example 41→Example 42 to obtain the following compounds of Examples.

Example 42(1)

N-[4-{4-amino-7-[cis-3-(hydroxymethyl)cyclobutyl]-7H-pyrrolo[2,3-d]pyrimidin-5-yl}phenyl)-1-(4-fluorophenyl)-2,5-dioxo-1,2,5,6,7,8-hexahydro-3-quinolinecarboxamide (LC-MS/ELSD): (retention time: 0.73 minutes);
$^1$H-NMR (CDCl$_3$): δ 1.95-2.05, 2.22-2.31, 2.26-2.55, 3.48, 4.56, 5.06-5.14, 6.04, 7.45-7.58, 7.80, 8.12, 8.95, 11.49.

Example 42(2)

N-(4-{4-amino-7-[cis-3-(hydroxymethyl)cyclobutyl]-7H-pyrrolo[2,3-d]pyrimidin-5-yl}phenyl)-1-cyclopropyl-2,5-dioxo-1,2,5,6,7,8-hexahydro-3-quinolinecarboxamide (LC-MS/ELSD): (retention time: 0.65 minutes);
$^1$H-NMR (CDCl$_3$): δ 0.92-1.01, 1.40-1.49, 2.17-2.27, 2.43-2.71, 2.98-3.07, 3.24, 3.75, 5.07-5.15, 5.47, 7.13, 7.55, 7.85, 9.17, 11.61.

Example 42(3)

N-(4-{4-amino-7-[cis-3-(hydroxymethyl)cyclobutyl]-7H-pyrrolo[2,3-d]pyrimidin-5-yl}phenyl)-1-methyl-2,5-dioxo-1,2,5,6,7,8-hexahydro-3-quinolinecarboxamide (LC-MS/ELSD): (retention time: 0.61 minutes);
$^1$H-NMR (CD$_3$OD): δ 2.21-2.38, 2.58-2.62, 3.16, 3.64, 3.72, 5.11-5.16, 7.43, 7.52, 7.80, 8.13, 9.04.

Example 42(4)

N-(4-[4-amino-7-[cis-3-(hydroxymethyl)cyclobutyl]-7H-pyrrolo[2,3-d]pyrimidin-5-yl}phenyl)-1-ethyl-2,5-dioxo-1,2,5,6,7,8-hexahydro-3-quinolinecarboxamide (LC-MS/ELSD): (retention time: 0.65 minutes);
$^1$H-NMR (CDCl$_3$): δ 1.44, 2.23-2.31, 2.43-2.53, 2.55-2.70, 3.08, 3.75, 4.25-4.30, 5.07-5.11, 7.08, 7.47, 7.85, 8.31, 9.22, 11.70.

Example 43

5-(4-chloro-7-methyl-7H-pyrrolo[2,3-d]pyrimidin-5-yl)-pyridine-2-amine

Under argon atmosphere, to a 1,4-dioxane solution (20 mL) of the compound (2 g) produced in Example 1, 5-(4,4,5,5-tetramethyl-1,3,2-dioxaborolan-2-yl)pyridine-2-amine (1.8 g), 2 mol/L potassium phosphate aqueous solution (10 mL), and tetrakis(triphenylphosphine)palladium (394 mg) were added. The resulting mixture was stirred at a bath temperature (90° C.) for 14 hours. The mixture was left to cool to room temperature. Thereafter, water was added thereto, followed by extraction with ethyl acetate. The extracted solution was washed with water and a saturated saline solution, and dried over anhydrous sodium sulfate. Thereafter, the solvent was removed by evaporation under reduced pressure. The resulting product was purified by column chromatography on silica gel (ethyl acetate→ethyl acetate:methanol=9:1) to obtain the title compound (873 mg) having the following physical property values.

TLC: Rf 0.11 (ethyl acetate);
$^1$H-NMR (DMSO-d$_6$): δ 3.86, 6.00, 6.49, 7.49, 7.71, 7.99, 8.62.

Example 44

N-[5-(4-chloro-7-methyl-7H-pyrrolo[2,3-d]pyrimidin-5-yl)-2-pyridinyl]-2,5-dioxo-1-phenyl-1,2,5,6,7,8-hexahydro-3-quinolinecarboxamide Under argon atmosphere, to a dichloromethane solution (2 mL) of the compound (240 mg) produced in Example 5, oxalyl chloride (0.100 mL) and DMF (0.100 mL) were added. The resulting mixture was stirred at room temperature for 30 minutes. The reaction solution was removed by evaporation under reduced pressure, and dichloromethane (2 mL), triethylamine (0.161 mL), and the compound (200 mg) produced in Example 43 were added thereto. The resulting mixture was stirred at room temperature for two hours. Water was added thereto, followed by extraction with chloroform. The extracted solution was washed with water and a saturated saline solution, and then dried over anhydrous sodium sulfate. Thereafter, the solvent was removed by evaporation under reduced pressure. The resulting product was purified by silica gel column chromatograph (hexane:ethyl acetate=1:9) to obtain the title compound (279 mg) having the following physical property values.

TLC: Rf 0.52 (ethyl acetate);
$^1$H-NMR (CDCl$_3$): δ 2.11, 2.59, 3.94, 7.09, 7.26, 7.46-7.65, 7.86, 8.41, 8.43, 8.68, 9.32, 11.90.

Example 45

N-[5-(4-amino-7-methyl-7H-pyrrolo[2,3-d]pyrimidin-5-yl)-2-pyridinyl]-2,5-dioxo-1-phenyl-1,2,5,6,7,8-hexahydro-3-quinolinecarboxamide

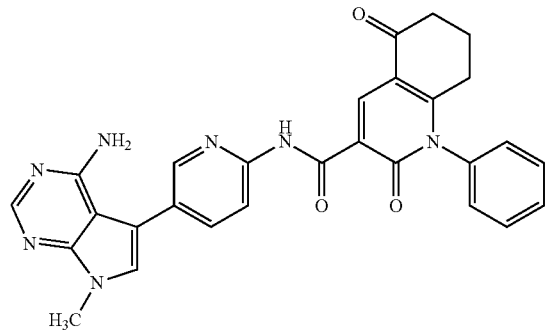 [SMILES: Cn1cc(-c2ccc(NC(=O)c3cc4c(n(-c5ccccc5)c3=O)CCCC4=O)nc2)c2c(N)ncnc21]

The compound produced in Example 44 was used and subjected to the same procedure as in Example 3 to obtain the title compound having the following physical property values.

TLC: Rf 0.54 (ethyl acetate:methanol=5:1);
$^1$H-NMR (CDCl$_3$): δ 2.11, 2.59, 3.85, 4.99, 6.96, 7.24, 7.62, 7.82, 8.36, 8.41, 8.44, 9.32, 11.91

Example 45(1) to 45(31)

4-chloro-5-iodo-7-methyl-7H-pyrrolo[2,3-d]pyrimidine or the corresponding pyrrolo pyrimidine derivative, 5-(4,4,5,5-tetramethyl-1,3,2-dioxaborolan-2-yl)pyridine-2-amine, and the compound produced in Example 5 or the corresponding carboxylic acid derivative instead thereof were used and subjected to the procedure having the same object as in Example 43→Example 44→Example 45 to obtain the following compounds of Examples.

Example 45(1)

N-[5-(4-amino-7-methyl-7H-pyrrolo[2,3-d]pyrimidin-5-yl)-2-pyridinyl]-2-oxo-1-phenyl-1,2-dihydro-3-quinolinecarboxamide trifluoro hydrochloride (LC-MS/ELSD): (retention time: 0.80 minutes);
$^1$H-NMR (DMSO-d$_6$): δ 3.83, 6.63, 7.39-7.49, 7.60-7.73, 7.91-7.96, 8.18, 8.37-8.46, 9.21, 12.38.

Example 45(2)

N-{5-[4-amino-7-(2-hydroxy-2-methylpropyl)-7H-pyrrolo[2,3-d]pyrimidin-5-yl]-2-pyridinyl}-2-oxo-1-phenyl-1,2-dihydro-3-quinolinecarboxamidetrifluoroacetate (LC-MS/ELSD): (retention time: 0.78 minutes);
$^1$H-NMR (DMSO-d$_6$): δ 1.10, 4.17, 6.64, 7.40-7.49, 7.57, 7.61-7.71, 7.94-7.98, 8.17-8.19, 8.36, 8.41-8.46, 9.21, 12.82.

Example 45(3)

N-[5-(4-amino-7-methyl-7H-pyrrolo[2,3-d]pyrimidin-5-yl)-2-pyridinyl]-5-cyclopropyl-2-oxo-1-phenyl-1,2-dihydro-3-pyridinecarboxamide trifluoroacetate (LC-MS/ELSD): (retention time: 0.76 minutes);
$^1$H-NMR (DMSO-d$_6$): δ 0.66-0.79, 0.88-0.96, 1.92-2.02, 3.83, 7.50-7.61, 7.65, 7.90, 7.97, 8.34, 8.39-8.43, 12.52.

Example 45(4)

N-{5-[4-amino-7-(2-hydroxy-2-methylpropyl)-7H-pyrrolo[2,3-d]pyrimidin-5-yl]-2-pyridinyl}-2,5-dioxo-1-phenyl-1,2,5,6,7,8-hexahydro-3-quinolinecarboxamide (LC-MS/ELSD): (retention time: 0.71 minutes);
$^1$H-NMR (DMSO-d$_6$): δ 1.08, 1.95-2.05, 2.52-2.56, 4.11, 4.82, 6.18, 7.37, 7.45-7.50, 7.56-7.68, 7.92, 8.14, 8.35-8.41, 8.99, 11.89.

Example 45(5)

5-acetyl-N-{5-[4-amino-7-(2-hydroxy-2-methylpropyl)-7H-pyrrolo[2,3-d]pyrimidin-5-yl]-2-pyridinyl}-6-methyl-2-oxo-1-phenyl-1,2-dihydro-3-pyridinecarboxamide trifluoroacetate (LC-MS/ELSD): (retention time: 0.68 minutes);
$^1$H-NMR (DMSO-d$_6$): δ 1.08, 2.31, 2.63, 4.14, 7.41-7.65, 7.92, 8.26, 8.37-8.40, 8.98, 12.02.

Example 45(6)

N-[5-(4-amino-7-methyl-7H-pyrrolo[2,3-d]pyrimidin-5-yl)-2-pyridinyl]-1-cyclopropyl-2,5-dioxo-1,2,5,6,7,8-hexahydro-3-quinolinecarboxamide (LC-MS/ELSD): (retention time: 0.59 minutes);
$^1$H-NMR (DMSO-d$_6$): δ 0.96-1.04, 1.22-1.38, 2.08-2.22, 2.48-2.63, 3.18-3.22, 3.30-3.38, 3.79, 6.25, 7.44, 7.94, 8.21, 8.38, 8.47, 8.86, 12.14.

Example 45(7)

N-[5-(4-amino-7-methyl-7H-pyrrolo[2,3-d]pyrimidin-5-yl)-2-pyridinyl]-1-(cyclopropyl methyl)-2,5-dioxo-1,2,5,6,7,8-hexahydro-3-quinolinecarboxamide (LC-MS/ELSD): (retention time: 0.68 minutes);
$^1$H-NMR (DMSO-d$_6$): δ 0.47-0.60, 1.19-1.36, 2.08-2.21, 2.53-2.63, 3.20-3.29, 3.75, 4.20, 6.21, 7.40, 7.87-7.93, 8.16, 8.35, 8.40-8.43, 8.90, 12.14.

Example 45(8)

N-[5-(4-amino-7-methyl-7H-pyrrolo[2,3-d]pyrimidin-5-yl)-2-pyridinyl]-1-(4,4-difluorocyclohexyl)-2,5-dioxo-1,2,5,6,7,8-hexahydro-3-quinolinecarboxamide (LC-MS/ELSD): (retention time: 0.71 minutes);
$^1$H-NMR (DMSO-d$_6$): δ 1.80-1.94, 1.98-2.22, 2.50-2.56, 2.80-3.05, 3.19-3.28, 3.75, 4.41-4.68, 6.21, 7.41, 7.83-7.96, 8.16, 8.34, 8.40-8.43, 8.87, 12.08.

Example 45(9)

N-[5-(4-amino-7-methyl-7H-pyrrolo[2,3-d]pyrimidin-5-yl)-2-pyridinyl]-2,5-dioxo-1-(3-pentanyl)-1,2,5,6,7,8-hexahydro-3-quinolinecarboxamide (LC-MS/ELSD): (retention time: 0.73 minutes);
$^1$H-NMR (DMSO-d$_6$): δ 0.76-0.90, 1.83-2.05, 2.06-2.21, 2.22-2.40, 2.52-2.60, 3.08-3.23, 3.75, 4.35-4.46, 6.20, 7.41, 7.87-7.93, 8.17, 8.35, 8.40-8.43, 8.91, 12.12.

Example 45(10)

N-[5-(4-amino-7-methyl-7H-pyrrolo[2,3-d]pyrimidin-5-yl)-2-pyridinyl]-1-(3-fluorobenzyl)-2,5-dioxo-1,2,5,6,7,8-hexahydro-3-quinolinecarboxamide (LC-MS/ELSD): (retention time: 0.71 minutes);
$^1$H-NMR (DMSO-d$_6$): δ 2.00-2.14, 2.51-2.59, 2.99-3.12, 3.75, 5.55, 6.21, 7.05-7.21, 7.35-7.48, 7.86-7.93, 8.16, 8.36, 8.40-8.43, 8.95, 12.04.

Example 45(11)

N-{5-[4-amino-7-(2-hydroxy-2-methylpropyl)-7H-pyrrolo[2,3-d]pyrimidin-5-yl]-2-pyridinyl}-1-(4-fluorophenyl)-2,5-dioxo-1,2,5,6,7,8-hexahydro-3-quinolinecarboxamide (LC-MS/ELSD): (retention time: 0.66 minutes);
$^1$H-NMR (DMSO-$d_6$): δ 1.07, 1.92-2.10, 2.52-2.57, 4.11, 4.84, 6.21, 7.36, 7.43-7.61, 7.88-7.94, 8.14, 8.35, 8.39-8.41, 8.98, 11.87.

Example 45(12)

N-{5-[4-amino-7-(2-hydroxy-2-methylpropyl)-7H-pyrrolo[2,3-d]pyrimidin-5-yl]-2-pyridinyl}-1-cyclobutyl-2,5-dioxo-1,2,5,6,7,8-hexahydro-3-quinolinecarboxamide (LC-MS/ELSD): (retention time: 0.66 minutes);
$^1$H-NMR (DMSO-$d_6$): δ 1.08, 1.67-1.92, 1.96-2.12, 2.44-2.61, 2.69-2.94, 3.03-3.16, 4.12, 4.86, 4.90-5.08, 6.22, 7.37, 7.87-7.96, 8.15, 8.36, 8.42-8.45, 8.84, 12.08.

Example 45(13)

N-{5-[4-amino-7-(2-hydroxy-2-methylpropyl)-7H-pyrrolo[2,3-d]pyrimidin-5-yl]-2-pyridinyl}-1-(2,2-dimethylpropyl)-2,5-dioxo-1,2,5,6,7,8-hexahydro-3-quinolinecarboxamide (LC-MS/ELSD): (retention time: 0.71 minutes);
$^1$H-NMR (DMSO-$d_6$): δ 1.00, 1.08, 2.01-2.18, 2.53-2.64, 3.14-3.24, 4.12, 4.16-4.44, 4.86, 6.21, 7.36, 7.87-7.95, 8.15, 8.36, 8.42-8.45, 8.90, 12.12.

Example 45(14)

N-{5-[4-amino-7-(2-hydroxy-2-methylpropyl)-7H-pyrrolo[2,3-d]pyrimidin-5-yl]-2-pyridinyl}-1-(3-hydroxy-3-methyl-2-butanyl)-2,5-dioxo-1,2,5,6,7,8-hexahydro-3-quinolinecarboxamide (LC-MS/ELSD): (retention time: 0.61 minutes);
$^1$H-NMR (DMSO-$d_6$): δ 1.07, 1.15, 1.27, 1.59, 2.03-2.09, 2.50-2.60, 3.10-3.18, 4.11, 4.62, 4.85, 5.19, 6.21, 7.36, 7.90-7.93, 8.14, 8.34, 8.41-8.43, 8.92, 11.92.

Example 45(15)

N-{5-[4-amino-7-(2-hydroxy-2-methylpropyl)-7H-pyrrolo[2,3-d]pyrimidin-5-yl]-2-pyridinyl}-2',5'-dioxo-1'-phenyl-2',5',6',8'-tetrahydro-1'H-spiro[cyclopropane-1,7'-quinoline]-3'-carboxamide (LC-MS/ELSD): (retention time: 0.70 minutes);
$^1$H-NMR (DMSO-$d_6$): δ 0.35-0.39, 0.40-0.44, 1.06, 2.43, 2.46, 4.10, 4.83, 6.20, 7.35, 7.43-7.47, 7.56-7.64, 7.88-7.92, 8.13, 8.34-8.39, 9.01, 11.87.

Example 45(16)

N-{5-[4-amino-7-(2-hydroxy-2-methylpropyl)-7H-pyrrolo[2,3-d]pyrimidin-5-yl]-2-pyridinyl}-2',5'-dioxo-1'-phenyl-2',5',6',8'-tetrahydro-1'H-spiro[cyclobutane-1,7'-quinoline]-3'-carboxamide (LC-MS/ELSD): (retention time: 0.74 minutes);
$^1$H-NMR (DMSO-$d_6$): δ 1.06, 1.62-1.95, 2.67, 2.71, 4.10, 4.83, 6.20, 7.35, 7.48-7.51, 7.58-7.63, 7.88-7.92, 8.13, 8.35, 8.36-8.39, 8.93, 11.86.

Example 45(17)

N-{5-[4-amino-7-(2-hydroxy-2-methylpropyl)-7H-pyrrolo[2,3-d]pyrimidin-5-yl]-2-pyridinyl}-6,6-dimethyl-2,5-dioxo-1-phenyl-1,2,5,6,7,8-hexahydro-3-quinolinecarboxamide (LC-MS/ELSD): (retention time: 0.74 minutes);
$^1$H-NMR (DMSO-$d_6$): δ 1.06, 1.13, 1.81-1.90, 2.43-2.52, 4.10, 4.83, 6.20, 7.35, 7.50-7.67, 7.88-7.92, 8.13, 8.35, 8.37-8.39, 8.99, 11.91.

Example 45(18)

N-{5-[4-amino-7-(2-hydroxy-2-methylpropyl)-7H-pyrrolo[2,3-d]pyrimidin-5-yl]-2-pyridinyl}-2,5-dioxo-1-phenyl-2,5,6,7,8,9-hexahydro-1H-cyclohepta[b]pyridine-3-carboxamide (LC-MS/ELSD): (retention time: 0.67 minutes);
$^1$H-NMR (DMSO-$d_6$): δ 1.06, 1.63-1.75, 1.75-1.83, 2.62-2.67, 2.71-2.75, 4.10, 4.83, 6.20, 7.35, 7.46-7.50, 7.56-7.67, 7.87-7.91, 8.13, 8.35, 8.36-38, 8.80, 11.96.

Example 45(19)

N-{5-[4-amino-7-(2-hydroxy-2-methylpropyl)-7H-pyrrolo[2,3-d]pyrimidin-5-yl]-2-pyridinyl}-1-(3-fluorobenzyl)-2,5-dioxo-1,2,5,6,7,8-hexahydro-3-quinolinecarboxamide (LC-MS/ELSD): (retention time: 0.70 minutes);
$^1$H-NMR (DMSO-$d_6$): δ 1.07, 2.01-2.11, 2.49-2.58, 3.00-3.07, 4.11, 4.84, 5.54, 6.20, 7.08-7.19, 7.36, 7.37-7.46, 7.90-7.93, 8.14, 8.36, 8.41-8.42, 8.94, 12.03.

Example 45(20)

N-[5-(4-amino-7-methyl-7H-pyrrolo[2,3-d]pyrimidin-5-yl)-2-pyridinyl]-1-(2-hydroxy-1-phenylethyl)-2,5-dioxo-1,2,5,6,7,8-hexahydro-3-quinolinecarboxamide (LC-MS/ELSD): (retention time: 0.67 minutes);
$^1$H-NMR (DMSO-$d_6$): δ 2.00-2.27, 2.53-2.65, 3.20-3.51, 3.73, 4.38-4.49, 4.50-4.66, 5.22-5.32, 5.74-5.85, 6.17, 7.21-7.39, 7.84-88, 8.14, 8.26-8.35, 8.92, 11.82.

Example 45(21)

N-[5-(4-amino-7-cyclopentyl-7H-pyrrolo[2,3-d]pyrimidin-5-yl)-2-pyridinyl]-2-oxo-1-phenyl-1,2-dihydro-3-pyridinecarboxamide (LC-MS/ELSD): (retention time: 0.81 minutes);
$^1$H-NMR (CDCl$_3$): δ 1.77-1.79, 1.90-1.93, 2.23-2.27, 4.99, 5.19-5.24, 6.60, 7.05, 7.41-7.49, 7.53-7.58, 7.67, 7.82, 8.33, 8.42-8.45, 8.74.

Example 45(22)

N-[5-(4-amino-7-methyl-7H-pyrrolo[2,3-d]pyrimidin-5-yl)-2-pyridinyl]-7,7-dimethyl-2,5-dioxo-1-phenyl-1,2,5,6,7,8-hexahydro-3-quinolinecarboxamide TLC: Rf 0.74 (ethyl acetate:methanol=5:1);
$^1$H-NMR (CDCl$_3$): δ 0.96, 2.45, 3.73, 6.19, 7.38, 7.44, 7.62, 7.88, 8.14, 8.31, 8.36, 8.95, 11.86.

Example 45(23)

N-[5-(4-amino-7-methyl-7H-pyrrolo[2,3-d]pyrimidin-5-yl)-2-pyridinyl]-1-(4-fluorophenyl)-2,5-dioxo-1,2,5,6,7,8-hexahydro-3-quinolinecarboxamide TLC: Rf 0.73 (ethyl acetate:methanol=5:1);
$^1$H-NMR (CDCl$_3$): δ 2.12, 2.59, 3.85, 5.06, 6.96, 7.30, 7.82, 8.35, 8.40, 8.43, 9.29, 11.83.

Example 45(24)

N-[5-(4-amino-7-methyl-7H-pyrrolo[2,3-d]pyrimidin-5-yl)-2-pyridinyl]-2',5'-dioxo-1'-phenyl-2',5',6',8'-tetrahydro-1'H-spiro[cyclopropane-1,7'-quinoline]-3'-carboxamide

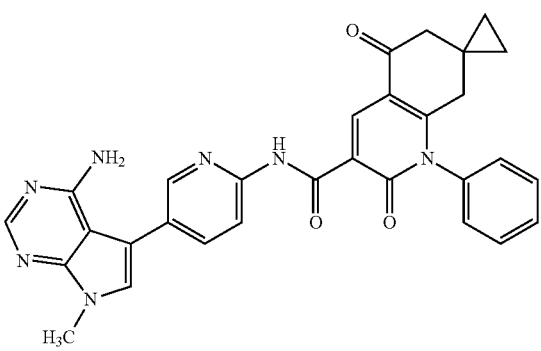 [SMILES: Cn1cc(-c2ccc(NC(=O)c3cc4c(n(-c5ccccc5)c3=O)CC3(CC3)CC4=O)nc2)c2c(N)ncnc21]

TLC: Rf 0.52 (ethyl acetate:methanol=5:1);
$^1$H-NMR (CDCl$_3$): δ 2.11-2.24, 2.60, 2.96, 3.84, 5.10, 5.50, 6.86-6.97, 7.02-7.11, 7.33-7.42, 7.46, 7.71, 8.35, 9.31, 11.58.

Example 45(25)

N-[5-(4-amino-7-methyl-7H-pyrrolo[2,3-d]pyrimidin-5-yl)-2-pyridinyl]-2',5'-dioxo-1'-phenyl-2',5',6',8'-tetrahydro-1'H-spiro[cyclobutane-1,7'-quinoline]-3'-carboxamide TLC: Rf 0.53 (ethyl acetate:methanol=5:1);
$^1$H-NMR (CDCl$_3$): δ 1.75-1.92, 2.64, 2.72, 3.84, 4.97, 6.95, 7.25, 7.63, 7.81, 8.35, 8.39, 8.43, 9.27, 11.88.

Example 45(26)

N-[5-(4-amino-7-methyl-7H-pyrrolo[2,3-d]pyrimidin-5-yl)-2-pyridinyl]-1-(2,2-dimethylpropyl)-2,5-dioxo-1,2,5,6,7,8-hexahydro-3-quinolinecarboxamide TLC: Rf 0.35 (ethyl acetate, NH silica);
$^1$H-NMR (CDCl$_3$): δ 12.12, 8.91, 8.42, 8.36, 8.17, 7.86-7.94, 7.40, 6.11-6.30, 4.07-4.48, 3.75, 3.11-3.25, 2.54-2.64, 1.98-2.19, 1.00.

Example 45(27)

N-[5-(4-amino-7-methyl-7H-pyrrolo[2,3-d]pyrimidin-5-yl)-2-pyridinyl]-2,5-dioxo-1-phenyl-2,5,6,7,8,9-hexahydro-1H-cyclohepta[b]pyridine-3-carboxamide TLC: Rf 0.29 (ethyl acetate, NH silica);
$^1$H-NMR (CDCl$_3$): δ 11.97, 8.82, 8.31-8.40, 8.16, 7.84-7.93, 7.53-7.71, 7.45-7.52, 7.39, 6.04-6.32, 3.74, 2.70-2.81, 2.60-2.69, 1.59-1.87.

Example 45(28)

N-[5-(4-amino-7-methyl-7H-pyrrolo[2,3-d]pyrimidin-5-yl)-2-pyridinyl]-4,6-dimethyl-2-oxo-1-phenyl-1,2-dihydro-3-pyridinecarboxamide (LC-MS/ELSD): (retention time: 0.68 minutes);
$^1$H-NMR (CDCl$_3$): δ 2.04, 2.80, 3.83, 4.98, 6.25, 6.94, 7.21, 7.48-7.58, 7.77, 8.34-8.40, 12.44.

Example 45(29)

N-[5-(4-amino-7-methyl-7H-pyrrolo[2,3-d]pyrimidin-5-yl)-2-pyridinyl]-1-cyclobutyl-2,5-dioxo-1,2,5,6,7,8-hexahydro-3-quinolinecarboxamide (LC-MS/ELSD): (retention time: 0.67 minutes);
$^1$H-NMR (DMSO-d$_6$): δ 1.65-1.94, 1.97-2.14, 2.53-2.60, 2.74-2.93, 3.02-3.14, 3.75, 4.83-5.09, 6.21, 7.41, 7.86-7.94, 8.17, 8.34, 8.40-8.45, 8.84, 12.08.

Example 45(30)

N-{5-[4-amino-7-(2-hydroxy-2-methylpropyl)-7H-pyrrolo[2,3-d]pyrimidin-5-yl]-2-pyridinyl}-1-(2-hydroxy-1-phenylethyl)-2,5-dioxo-1,2,5,6,7,8-hexahydro-3-quinolinecarboxamide (LC-MS/ELSD): (retention time: 0.66 minutes);
$^1$H-NMR (DMSO-d$_6$): δ 1.06, 2.01-2.27, 2.49-2.64, 3.20-3.50, 4.10, 4.38-4.46, 4.51-4.64, 4.84, 5.21-5.33, 5.74-5.84, 6.17, 7.21-7.39, 7.86-7.90, 8.13, 8.29, 8.36, 8.92, 11.82.

Example 45(31)

N-[5-(4-amino-7-methyl-7H-pyrrolo[2,3-d]pyrimidin-5-yl)-2-pyridinyl]-2-oxo-1-phenyl-1,2-dihydro-3-pyridinecarboxamide (LC-MS/ELSD): (retention time: 0.67 minutes);
$^1$H-NMR (CD$_3$OD): δ 3.93, 6.74, 7.42-7.52, 7.52-7.65, 7.92-7.97, 7.99, 8.34, 8.39-8.55, 8.72.

Example 46 diethyl[(2E)-3-ethoxy propo-2-ene-1-ylidene]propanediate 1,1,3,3-tetraethoxypropane (CAS registration No.: 102-52-3) (1000 mg), diethylmalonate (680 mg), and zinc bromide (300 mg) were dissolved in acetic anhydride (20 mL), and the resulting mixture was stirred at 60° C. for two hours. The reaction solution was placed in ice water, followed by extraction with ethyl acetate. The organic layer was dried over sodium sulfate, and filtered. Then, the solvent was removed by evaporation by concentration under reduced pressure. The obtained residue was partially purified by column chromatography on silica gel (hexane:ethyl acetate=10:0→70:30) to obtain title compound (600 mg) having the following physical property values. The obtained compound was used as it is for the subsequent reaction.

Example 47 diethyl{(2E)-3-[(phenylcyclopropyl)amino]propo-2-ene-1-ylidene}propanedioate

The compound (600 mg) produced in Example 46 and 1-phenyl cyclopropane amine (150 mg) were dissolved in n-butanol (10 mL). The resulting solution was stirred at 90° C. for one hour. The reaction solution was concentrated under reduced pressure to obtain a crude product including the title compound (300 mg) having the following physical property value. The obtained compound was used for the subsequent reaction without purification.
MS (M+H): 330.

Example 48 ethyl 2-oxo-1-(1-phenylcyclopropyl)-1,2-dihydro-pyridine-3-carboxylate

The compound (200 mg) produced in Example 47 was dissolved in n-butanol (5 mL), and sodium ethoxide (82 mg) was added thereto. The mixture was stirred at room temperature for one hour. The reaction solution was placed in ice water, followed by extraction with ethyl acetate. The organic layer was dried over sodium sulfate, filtered, and then the solvent was removed by evaporation by concentration under reduced pressure to obtain a crude product (150 mg) including the title compound having the following physical property value. The obtained compound was used for the subsequent reaction without purification.
MS (M+H): 284.

Example 49

N-[4-(4-amino-7-methyl-7H-pyrrolo[2,3-d]pyrimidin-5-yl)phenyl]-2-oxo-1-(1-phenyl cyclopropyl)-1,2-dihydro-3-pyridinecarboxamide The compound (150 mg) produced in Example 48 and the compound (50 mg) produced in Example 3 were used and subjected to the procedure having the same object as in Example 23→Example 6 to obtain the title compound (40 mg) having the following physical property values.

(LC-MS/ELSD): (retention time: 0.65 minutes);
$^1$H-NMR (CDCl$_3$): δ 2.41-2.72, 3.74, 5.03, 5.04-5.16, 6.59, 7.12, 7.39-7.46, 7.48-7.60, 7.67, 7.81, 8.32, 8.40-8.49, 8.73, 12.42.

Example 50 methyl 1-(2,2-dimethylpropyl)-2-oxo-1,2-dihydro-pyridine-3-carboxylate

Methyl 2-oxo-2H-pyran-3-carboxylate (CAS registration No.: 25991-27-9) (500 mg) was dissolved in THF (100 mL), and 2,2-dimethylpropane-1-amine (340 mg) was added thereto. The resulting mixture was stirred at room temperature for three hours. Then, 1-ethyl-3-(3-dimethylaminopropyl)carbodiimide hydrochloride (860 mg) and N,N-dimethyl-4-aminopyridine (400 mg) were added, and the resulting mixture was stirred at room temperature for 48 hours. To the reaction solution, 1 mol/L hydrochloric acid was added, followed by extraction with ethyl acetate. The organic layer was washed with water, dried over sodium sulfate, and filtered. Thereafter, the solvent was distilled off by concentration under reduced pressure. The obtained residue was washed with water to obtain the title compound (0.60 g) having the following physical property values.

$^1$H-NMR (CDCl$_3$): δ 0.99, 3.88, 3.98, 6.18, 7.74, 8.13.

Example 51

N-[4-(4-amino-7-cyclopentyl-7H-pyrrolo[2,3-d]pyrimidin-5-yl)phenyl]-1-(2,2-dimethyl propyl)-2-oxo-1,2-dihydro-3-pyridinecarboxamide 4-(4-chloro-7-cyclopentyl-7H-pyrrolo[2,3-d]pyrimidin-5-yl)aniline (200 mg) produced in accordance with Example 7→Example 2 using 4-chloro-5-iodo-7H-pyrrolo[2,3-d]pyrimidine and cyclopentanol, as well as the compound (140 mg) produced in Example 50 were used and subjected to the same procedure as in Example 49→Example 3 to obtain the title compound (290 mg) having the following physical property values.

(LC-MS/ELSD): (retention time: 4.43 minutes);
$^1$H-NMR (CDCl$_3$): δ 1.04, 1.77-1.81, 1.89-1.93, 2.22-2.29, 3.99, 5.08, 5.18-5.25, 6.46, 7.02, 7.47, 7.51, 7.85, 8.32, 8.64, 12.17.

Example 51(1) to 51(20)

4-(4-chloro-7-cyclopentyl-7H-pyrrolo[2,3-d]pyrimidin-5-yl)aniline or the corresponding pyrrolo pyrimidine derivative instead thereof, and the corresponding ester derivative instead of the compound produced in Example 50 were used and subjected to the procedure having the same object as in Example 51 to obtain the following compounds of Examples.

Example 51(1)

N-[4-(4-amino-7-cyclopentyl-7H-pyrrolo[2,3-d]pyrimidin-5-yl)phenyl]-1-isobutyl-2-oxo-1,2-dihydro-3-pyridinecarboxamide (LC-MS/ELSD): (retention time: 4.36 minutes);
$^1$H-NMR (CDCl$_3$): δ 1.00, 1.74-1.80, 1.85-1.93, 2.22-2.31, 3.90, 5.07, 5.18-5.26, 6.49, 7.03, 7.44-7.48, 7.51, 7.84-7.86, 8.32, 8.65, 12.14.

Example 51(2)

N-[4-(4-amino-7-cyclopentyl-7H-pyrrolo[2,3-d]pyrimidin-5-yl)phenyl]-1-isopropyl-2-oxo-1,2-dihydro-3-pyridinecarboxamide (LC-MS/ELSD): (retention time: 4.29 minutes);
$^1$H-NMR (CDCl$_3$): δ 1.46, 1.76-1.82, 1.84-1.93, 2.22-2.29, 5.09, 5.16-5.26, 5.36-5.44, 6.56, 7.03, 7.45-7.48, 7.64, 7.83-7.87, 8.33, 8.63, 12.23.

Example 51(3)

N-[4-(4-amino-7-cyclopentyl-7H-pyrrolo[2,3-d]pyrimidin-5-yl)phenyl]-1-(3-methyl-2-butanyl)-2-oxo-1,2-dihydro-3-pyridinecarboxamide (LC-MS/ELSD): (retention time: 4.40 minutes);
$^1$H-NMR (CDCl$_3$): δ 0.84, 1.08, 1.42, 1.75-2.01, 2.22-2.29, 4.98-5.08, 5.10, 5.18-5.26, 6.54, 7.03, 7.46, 7.54, 7.85, 8.32, 8.62, 12.20.

Example 51(4)

N-[4-(4-amino-7-cyclopentyl-7H-pyrrolo[2,3-d]pyrimidin-5-yl)phenyl]-2-oxo-2H-1,4'-bipyridine-3-carboxamide (LC-MS/ELSD): (retention time: 0.73 minutes);
$^1$H-NMR (DMSO-d$_6$): δ 1.72-1.89, 1.95-2.05, 2.08-2.25, 5.04-5.12, 6.05, 6.78, 7.40, 7.46, 7.67, 7.79, 8.13-8.16, 8.61, 8.81, 11.84.

Example 51(5)

N-[4-(4-amino-7-cyclopentyl-7H-pyrrolo[2,3-d]pyrimidin-5-yl)phenyl]-2-oxo-2H-1,3'-bipyridine-3-carboxamide trifluoroacetate (LC-MS/ELSD): (retention time: 0.75 minutes);
$^1$H-NMR (DMSO-d$_6$): δ 1.69-1.71, 1.87-1.99, 2.13-2.18, 5.10-5.58, 6.80, 7.49, 7.65-7.67, 7.74, 7.83, 8.05, 8.08, 8.17, 8.62, 8.77, 11.93.

Example 51(6)

N-{4-[4-amino-7-(1-methyl-4-piperidinyl)-7H-pyrrolo[2,3-d]pyrimidin-5-yl]phenyl}-1-(4-methylphenyl)-2-oxo-1,2-dihydro-3-pyridinecarboxamide (LC-MS/ELSD): (retention time: 0.66 minutes);
$^1$H-NMR (CDCl$_3$): δ 2.17-2.20, 2.46, 2.53-2.63, 3.35, 4.82-4.89, 5.20, 6.59, 7.09, 7.28-7.39, 7.42, 7.63, 7.82, 8.30, 8.75, 12.02.

Example 51(7)

N-{4-[4-amino-7-(1-methyl-4-piperidinyl)-7H-pyrrolo[2,3-d]pyrimidin-5-yl]phenyl}-1-(4-fluorophenyl)-2-oxo-1,2-dihydro-3-pyridinecarboxamide (LC-MS/ELSD): (retention time: 0.57 minutes);
$^1$H-NMR (CDCl$_3$): δ 2.09, 2.23-2.29, 2.37, 3.01-3.04, 4.70-4.79, 5.10, 6.61, 7.04, 7.25-7.30, 7.40-7.45, 7.62, 7.81, 8.32, 8.77, 11.89.

Example 51(8)

N-{4-[4-amino-7-(1-methyl-4-piperidinyl)-7H-pyrrolo[2,3-d]pyrimidin-5-yl]phenyl}-2-oxo-1-[3-(trifluoromethyl)phenyl]-1,2-dihydro-3-pyridinecarboxamide (LC-MS/ELSD): (retention time: 0.63 minutes);
$^1$H-NMR (CDCl$_3$): δ 2.09, 2.23-2.29, 2.36, 3.01-3.04, 4.72-4.76, 5.10, 6.65, 7.03, 7.45, 7.61-7.82, 8.31, 8.79, 11.80.

Example 51(9)

N-{4-[4-amino-7-(1-methyl-4-piperidinyl)-7H-pyrrolo[2,3-d]pyrimidin-5-yl]phenyl}-1-(3-methylphenyl)-2-oxo-1,2-dihydro-3-pyridinecarboxamide (LC-MS/ELSD): (retention time: 0.63 minutes);
$^1$H-NMR (CDCl$_3$): δ 2.12-2.22, 2.22-2.39, 2.46, 2.49-2.69, 3.22-3.41, 4.77-4.89, 6.60, 7.07, 7.20-7.23, 7.33-7.35, 7.41-7.49, 7.63, 7.84, 8.27, 8.76, 12.01.

Example 51(10)

N-{4-[4-amino-7-(1-methyl-4-piperidinyl)-7H-pyrrolo[2,3-d]pyrimidin-5-yl]phenyl}-1-(2-fluorophenyl)-2-oxo-1,2-dihydro-3-pyridinecarboxamide (LC-MS/ELSD): (retention time: 0.57 minutes);
$^1$H-NMR (CDCl$_3$): δ 2.03-2.16, 2.19-2.33, 2.37, 2.96-3.11, 4.69-4.82, 5.08, 6.63, 7.04, 7.33-7.45, 7.52-7.58, 7.82, 8.32, 8.78, 11.82.

Example 51(11)

N-{4-[4-amino-7-(1-methyl-4-piperidinyl)-7H-pyrrolo[2,3-d]pyrimidin-5-yl]phenyl}-1-(3-chlorophenyl)-2-oxo-1,2-dihydro-3-pyridinecarboxamide (LC-MS/ELSD): (retention time: 0.63 minutes);
$^1$H-NMR (CDCl$_3$): δ 2.03-2.14, 2.19-2.32, 2.36, 2.97-3.07, 4.67-4.81, 5.08, 6.62, 7.04, 7.31-7.36, 7.42-7.48, 7.53, 7.60, 7.82, 8.32, 8.77, 11.84.

Example 51(12)

N-{4-[4-amino-7-(1-methyl-4-piperidinyl)-7H-pyrrolo[2,3-d]pyrimidin-5-yl]phenyl}-1-benzyl-2-oxo-1,2-dihydro-3-pyridinecarboxamide (LC-MS/ELSD): (retention time: 0.61 minutes);
$^1$H-NMR (CDCl$_3$): δ 2.02-2.15, 2.19-2.30, 2.36, 2.97-3.07, 4.69-4.80, 5.10, 5.29, 6.50, 7.05, 7.30-7.49, 7.59, 7.85, 8.32, 8.65, 12.10.

Example 51(13)

N-{4-[4-amino-7-(1-methyl-4-piperidinyl)-7H-pyrrolo[2,3-d]pyrimidin-5-yl]phenyl}-1-(4-chlorophenyl)-2-oxo-1,2-dihydro-3-pyridinecarboxamide (LC-MS/ELSD): (retention time: 0.64 minutes);
$^1$H-NMR (CDCl$_3$): δ 2.03-2.09, 2.19-2.29, 2.35, 3.01-3.04, 4.67-4.78, 5.08, 6.61, 7.03, 7.35-7.40, 7.44, 7.53-7.61, 7.81, 8.31, 8.76, 11.86.

Example 51(14)

N-(4-{4-amino-7-[cis-3-(hydroxymethyl)cyclobutyl]-7H-pyrrolo[2,3-d]pyrimidin-5-yl}phenyl)-1-(4-chlorophenyl)-2-oxo-1,2-dihydro-3-pyridinecarboxamide (LC-MS/ELSD): (retention time: 0.76 minutes);
$^1$H-NMR (CDCl$_3$): δ 2.45-2.65, 3.74, 5.04-5.13, 6.62, 7.07, 7.36-7.39, 7.44, 7.54-7.61, 7.81, 8.30, 8.76, 11.85.

Example 51(15)

N-{4-[4-amino-7-(1-methyl-4-piperidinyl)-7H-pyrrolo[2,3-d]pyrimidin-5-yl]phenyl}-1-(3-fluorophenyl)-2-oxo-1,2-dihydro-3-pyridinecarboxamide (LC-MS/ELSD): (retention time: 0.58 minutes);
$^1$H-NMR (CDCl$_3$): δ 2.04-2.09, 2.21-2.28, 2.31, 3.00-3.02, 4.69-4.77, 5.09, 6.63, 7.04, 7.19-7.29, 7.44, 7.52-7.63, 7.82, 8.32, 8.77, 11.86.

Example 51(16)

N-{4-[4-amino-7-(1-methyl-4-piperidinyl)-7H-pyrrolo[2,3-d]pyrimidin-5-yl]phenyl}-1-(3-fluorobenzyl)-2-oxo-1,2-dihydro-3-pyridinecarboxamide (LC-MS/ELSD): (retention time: 0.58 minutes);
$^1$H-NMR (CDCl$_3$): δ 2.04-2.15, 2.19-2.28, 2.35, 3.00, 4.68-4.79, 5.07, 5.20, 6.52, 7.02-7.11, 7.33-7.38, 7.46, 7.58, 7.85, 8.30, 8.67, 12.01.

Example 51(17)

N-{4-[4-amino-7-(1-methyl-4-piperidinyl)-7H-pyrrolo[2,3-d]pyrimidin-5-yl]phenyl}-2-oxo-1-[(1 S)-1-phenylethyl]-1,2-dihydro-3-pyridinecarboxamide (LC-MS/ELSD): (retention time: 0.61 minutes);
$^1$H-NMR (CDCl$_3$): δ 1.81, 2.04-2.28, 2.35, 3.01, 4.68-4.79, 5.09, 6.44, 6.56, 7.05, 7.31-7.50, 7.87, 8.32, 8.61, 12.20.

Example 51(18)

N-{4-[4-amino-7-(1-methyl-4-piperidinyl)-7H-pyrrolo[2,3-d]pyrimidin-5-yl]phenyl}-1-(4-fluorobenzyl)-2-oxo-1,2-dihydro-3-pyridinecarboxamide (LC-MS/ELSD): (retention time: 0.60 minutes);
$^1$H-NMR (DMSO-d$_6$): δ 1.87-1.88, 2.07-2.11, 2.23, 2.91, 4.51-4.57, 5.31, 6.06, 6.69, 7.19-7.23, 7.43-7.46, 7.79, 8.13, 8.32, 8.50, 12.12.

Example 51(19)

N-{4-[4-amino-7-(1-methyl-4-piperidinyl)-7H-pyrrolo[2,3-d]pyrimidin-5-yl]phenyl}-1-(2-fluorobenzyl)-2-oxo-1,2-dihydro-3-pyridinecarboxamide (LC-MS/ELSD): (retention time: 0.57 minutes);
$^1$H-NMR (CDCl$_3$): δ 2.02-2.15, 2.18-2.30, 2.36, 2.95-3.07, 4.68-4.81, 5.08, 5.31, 6.50, 7.05, 7.09-7.21, 7.31-7.41, 7.42-7.54, 7.68-7.73, 7.85, 8.33, 8.64, 12.05.

Example 51(20)

N-{4-[4-amino-7-(1-methyl-4-piperidinyl)-7H-pyrrolo[2,3-d]pyrimidin-5-yl]phenyl}-2-oxo-1-(2-phenylethyl)-1,2-dihydro-3-pyridinecarboxamide (LC-MS/ELSD): (retention time: 0.58 minutes);
$^1$H-NMR (CDCl$_3$): δ 2.02-2.14, 2.18-2.30, 2.36, 2.97-3.07, 3.15, 4.31, 4.66-4.82, 5.09, 6.31, 7.06, 7.10-7.17, 7.27-7.34, 7.48, 7.88, 8.33, 8.61, 12.17.

Example 52 methyl 1-[(1R)-2-hydroxy-1-phenylethyl]-2-oxo-1,2-dihydropyridine-3-carboxylate

Methyl 2-oxo-2H-pyran-3-carboxylate (200 mg) and (R)-2-amino-2-phenyl ethanol (CAS registration No.: 56613-80-0) (190 mg) were used and subjected to the same procedure as in Example 50 to obtain the title compound (280 mg) having the following physical property value.
MS (M+H): 274.

Example 53 methyl 1-[(1R)-2-{[tert-butyl(dimethyl)silyl]oxy}-1-phenylethyl]-2-oxo-1,2-dihydropyridine-3-carboxylate The compound (280 mg) produced in Example 52 and imidazole (230 mg) were dissolved in dichloromethane (10 mL), and tert-butylchlorodimethylsilane (140 mg) was added thereto. The resulting mixture was stirred at room temperature for 16 hours. The reaction solution was placed in ice water, followed by extraction with ethyl acetate. The organic layer was washed with a saturated saline solution, dried over sodium sulfate, and filtered. Thereafter, the solvent was removed by evaporation by concentration under reduced pressure. The obtained residue was purified by column chromatography on silica gel (hexane:ethyl acetate=10:0→80:20) to obtain the title compound (250 mg) having the following physical property values.
MS (M+H): 388.
$^1$H-NMR (CDCl$_3$): δ −0.08, 0.01, 0.83, 3.92, 4.15-4.21, 4.32-4.38, 6.13, 6.35, 7.29-7.39, 7.40-7.45, 7.51, 8.15.

Example 54

N-[4-(4-amino-7-methyl-7H-pyrrolo[2,3-d]pyrimidin-5-yl)phenyl]-1-[(1R)-2-{[tert-butyl(dimethyl)silyl]oxy}-1-phenylethyl]-2-oxo-1,2-dihydropyridine-3-carboxamide The compound (250 mg) produced in Example 53 and the compound (100 mg) produced in Example 2 were used and subjected to the same procedure as in Example 49→Example 3 to obtain the title compound (180 mg) having the following physical property value.
MS (M+H): 595.

Example 55

N-[4-(4-amino-7-methyl-7H-pyrrolo[2,3-d]pyrimidin-5-yl)phenyl]-1-[(1R)-2-hydroxy-1-phenylethyl]-2-oxo-1,2-dihydro-3-pyridinecarboxamide

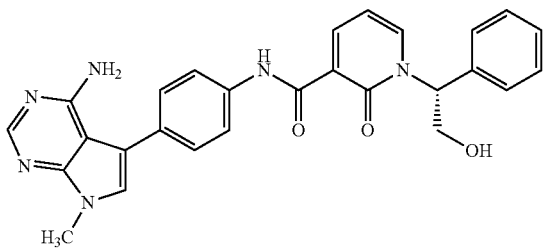 [SMILES: Cn1cc(-c2ccc(NC(=O)c3cccn([C@@H](CO)c4ccccc4)c3=O)cc2)c2c(N)ncnc21]

The compound (180 mg) produced in Example 54 was dissolved in methanol (10 mL), and 2 mol/L hydrochloric acid (3 mL) was added thereto at 0° C. The resulting solution was stirred for four hours. The reaction solution was concentrated under reduced pressure. Water was added to the obtained residue, followed by extraction with ethyl acetate. The organic layer was dried over sodium sulfate, filtered, and concentrated under reduced pressure. The obtained residue was purified by column chromatography on silica gel (dichloromethane:methanol=100:0→95:5) to obtain the title compound (20 mg) having the following physical property values.
(LC-MS/ELSD): (retention time: 0.70 minutes);
$^1$H-NMR (DMSO-$d_6$): δ 3.73, 4.04-4.13, 4.20-4.29, 5.33, 6.00-6.17, 6.20-6.27, 6.69, 7.30, 7.32-7.41, 7.43, 7.79, 8.15, 8.23, 8.50, 12.16.

Example 56

N-[4-(4-chloro-7-methyl-7H-pyrrolo[2,3-d]pyrimidin-5-yl)phenyl]-1-[(1R)-2-hydroxy-1-phenylethyl]-2-oxo-1,2-dihydropyridine-3-carboxamide The compound (110 mg) produced by subjecting the compound produced in Example 52 to the same procedure as in Example 23 and compound (100 mg) produced in Example 2 were used and subjected to the procedure having the same object as in Example 6 to obtain the title compound (140 mg) having the following physical property value.
MS (M+H): 500.

Example 57

(2R)-2-[3-{[4-(4-chloro-7-methyl-7H-pyrrolo[2,3-d]pyrimidin-5-yl)phenyl]carbamoyl}-2-oxopyridine-1(2H)-yl]-2-phenylethyl methanesulfonate The compound (140 mg) produced in Example 56 and triethylamine (0.2 mL) were dissolved in dichloromethane (10 mL), and methane sulfonyl chloride (0.06 mL) was added thereto. The resulting mixture was stirred at room temperature for 16 hours. The reaction solution was placed into ice water, followed by extraction with ethyl acetate. The organic layer was washed with a saturated saline solution, dried over sodium sulfate, and filtered. The solvent was distilled off by concentration under reduced pressure to obtain the title compound (150 mg) having the following physical property value.
MS (M+H): 579.

Example 58

N-[4-(4-amino-7-methyl-7H-pyrrolo[2,3-d]pyrimidin-5-yl)phenyl]-1-[(1R)-2-amino-1-phenylethyl]-2-oxo-1,2-dihydro-3-pyridinecarboxamide The compound (150 mg) produced in Example 57 was used and subjected to the procedure having the same object as in Example 3 to obtain the title compound (25 mg) having the following physical property values.
(LC-MS/ELSD): (retention time: 0.58 minutes);
$^1$H-NMR (DMSO-$d_6$): δ 3.41-3.59, 3.74, 5.95-6.17, 6.10-6.27, 6.69, 7.29, 7.31-7.42, 7.44, 7.79, 8.15, 8.22, 8.48, 12.17.

Example 59

N-(4-{4-amino-7-[2-(1-piperazinyl)ethyl]-7H-pyrrolo[2,3-d]pyrimidin-5-yl}phenyl)-2-oxo-1-phenyl-1,2-dihydro-3-pyridinecarboxamide The compound (175 mg) produced by subjecting 4-chloro-5-iodo-7H-pyrrolo[2,3-d]pyrimidine and tert-butyl 4-(2-hydroxyethyl)piperazine-1-carboxylate instead of tert-butyl 4-hydroxypiperidine-1-carboxylate to the same procedure as in Example 7, and the corresponding carboxylic acid derivative (99 mg) instead of the compound produced in Example 5 were used and subjected to the procedure having the same object as in Example 2→Example 3→Example 6→Example 8 to obtain the title compound having the following physical property values.
(LC-MS/ELSD): (retention time: 0.61 minutes);
$^1$H-NMR (CDCl$_3$): δ 2.51, 2.77, 2.88, 4.34, 5.09, 6.62, 7.04, 7.41-7.45, 7.54-7.64, 7.65, 7.82, 8.31, 8.77, 11.96.

Example 59(1) to 59(13)

4-chloro-5-iodo-7H-pyrrolo[2,3-d]pyrimidine, and the corresponding alcohol derivatives instead of tert-butyl 4-(2-hydroxyethyl)piperazine-1-carboxylate, and the corresponding carboxylic acid derivatives instead of the compound produced in Example 5 were used and subjected to the procedure having the same object as in Example 59 to obtain the following compounds of Examples.

Example 59(1)

N-{4-[4-amino-7-(4-piperidinyl)-7H-pyrrolo[2,3-d]pyrimidin-5-yl]phenyl}-2-oxo-1-phenyl-1,2-dihydro-3-pyridinecarboxamide dihydrochloride (LC-MS/ELSD): (retention time: 0.58 minutes);
$^1$H-NMR (CDCl$_3$): δ 2.10-2.44, 3.07-3.25, 3.41-3.45, 4.92-5.06, 6.73, 7.47-7.62, 7.84, 8.12, 8.51, 8.60, 9.04-9.32, 12.08.

Example 59(2)

N-{4-[4-amino-7-(3-pyrrolidinyl)-7H-pyrrolo[2,3-d]pyrimidin-5-yl]-3-fluorophenyl}-2-oxo-1-phenyl-1,2-dihydro-3-pyridinecarboxamide (LC-MS/ELSD): (retention time: 0.62 minutes);
$^1$H-NMR (DMSO-$d_6$): δ 1.24-1.31, 1.90-1.96, 2.23-2.33, 2.83-2.94, 3.16-3.19, 5.21-5.27, 6.01, 6.74, 7.36-7.46, 7.53-7.61, 7.90, 8.13-8.15, 8.60, 12.15.

Example 59(3)

N-{4-[4-amino-7-(4-piperidinyl)-7H-pyrrolo[2,3-d]pyrimidin-5-yl]phenyl}-1-(4-methyl phenyl)-2-oxo-1,2-dihydro-3-pyridinecarboxamide bis(trifluoroacetate)

(LC-MS/ELSD): (retention time: 0.65 minutes);
$^1$H-NMR (DMSO-$d_6$): δ 2.14-2.33, 2.40, 3.13-3.22, 3.44-3.47, 4.89-4.95, 6.72, 7.36-7.41, 7.46-7.48, 7.82, 8.09, 8.29, 8.43-8.45, 8.58, 8.74-8.77, 12.09.

Example 59(4)

N-{4-[4-amino-7-(3-pyrrolidinyl)-7H-pyrrolo[2,3-d]pyrimidin-5-yl]phenyl}-1-(4-methylphenyl)-2-oxo-1,2-dihydro-3-pyridinecarboxamide bis(trifluoroacetate)

(LC-MS/ELSD): (retention time: 0.66 minutes);
$^1$H-NMR (DMSO-$d_6$): δ 2.30-2.40, 3.55-3.75, 5.47-5.54, 6.72, 7.36-7.41, 7.47, 7.73, 7.83, 8.08, 8.35, 8.58, 9.31-9.39, 12.10.

Example 59(5)

N-{4-[4-amino-7-(4-piperidinyl)-7H-pyrrolo[2,3-d]pyrimidin-5-yl]phenyl}-2-oxo-1-[3-(trifluoromethyl)phenyl]-1,2-dihydro-3-pyridinecarboxamide (LC-MS/ELSD): (retention time: 0.67 minutes);
$^1$H-NMR (CDCl$_3$): δ 1.92-1.94, 2.08-2.11, 2.85-2.91, 3.23-3.27, 4.79-4.85, 5.08, 6.65, 7.05, 7.45, 7.61-7.75, 7.81, 8.32, 7.79, 11.80.

Example 59(6)

N-{4-[4-amino-7-(4-piperidinyl)-7H-pyrrolo[2,3-d]pyrimidin-5-yl]phenyl}-1-(4-fluorophenyl)-2-oxo-1,2-dihydro-3-pyridinecarboxamide bis(trifluoroacetate)

(LC-MS/ELSD): (retention time: 0.58 minutes);
$^1$H-NMR (DMSO-$d_6$): δ 2.18-2.28, 2.30-2.34, 3.45-3.47, 4.89-4.96, 6.73, 7.41-7.48, 7.60-7.63, 7.83, 8.12, 8.29, 8.40-8.43, 8.59, 8.70-8.73, 12.03.

Example 59(7)

N-{4-[4-amino-7-(4-piperidinyl)-7H-pyrrolo[2,3-d]pyrimidin-5-yl]phenyl}-1-(4-chlorophenyl)-2-oxo-1,2-dihydro-3-pyridinecarboxamide (LC-MS/ELSD): (retention time: 0.65 minutes);
$^1$H-NMR (CDCl$_3$): δ 1.85-1.97, 2.04-2.14, 2.82-2.93, 3.20-3.28, 4.76-4.85, 5.10, 6.73, 7.05, 7.36-7.40, 7.45, 7.54-7.62, 7.81, 8.32, 8.77, 11.89.

Example 59(8)

N-{4-[4-amino-7-(4-piperidinyl)-7H-pyrrolo[2,3-d]pyrimidin-5-yl]phenyl}-1-(3-methyl phenyl)-2-oxo-1,2-dihydro-3-pyridinecarboxamide (LC-MS/ELSD): (retention time: 0.58 minutes);
$^1$H-NMR (CDCl$_3$): δ 2.26-2.36, 2.46, 2.49-2.63, 3.09-3.22, 3.67-3.79, 4.95-5.07, 5.57, 6.59, 7.10, 7.19-7.24, 7.32-7.37 7.39-7.49, 7.63, 7.83, 8.28, 12.01.

Example 59(9)

N-{4-[4-amino-7-(4-piperidinyl)-7H-pyrrolo[2,3-d]pyrimidin-5-yl]phenyl}-1-(2-fluorophenyl)-2-oxo-1,2-dihydro-3-pyridinecarboxamide (LC-MS/ELSD): (retention time: 0.54 minutes);
$^1$H-NMR (CDCl$_3$): δ 1.94-2.08, 2.08-2.18, 2.87-2.99, 3.27-3.37, 4.80-4.91, 5.11, 6.63, 7.05, 7.31-7.41, 7.44, 7.52-7.61, 7.82, 8.32, 8.79, 11.83.

Example 59(10)

N-{4-[4-amino-7-(4-piperidinyl)-7H-pyrrolo[2,3-d]pyrimidin-5-yl]phenyl}-1-(3-fluorophenyl)-2-oxo-1,2-dihydro-3-pyridinecarboxamide bis(trifluoroacetate)

(LC-MS/ELSD): (retention time: 0.58 minutes);
$^1$H-NMR (DMSO-$d_6$): δ 2.14-2.29, 3.16-3.20, 4.87-4.95, 6.74, 7.39-7.68, 7.82, 8.14, 8.27, 8.36-8.39, 8.60, 8.69-8.72, 11.97.

Example 59(11)

N-{4-[4-amino-7-(4-piperidinyl)-7H-pyrrolo[2,3-d]pyrimidin-5-yl]phenyl}-1-(3-chlorophenyl)-2-oxo-1,2-dihydro-3-pyridinecarboxamide (LC-MS/ELSD): (retention time: 0.63 minutes);
$^1$H-NMR (CDCl$_3$): δ 1.86-2.06, 2.03-2.16, 2.84-2.96, 3.23-3.32, 4.77-4.89, 5.09, 6.62, 7.05, 7.31-7.36, 7.43-7.48, 7.53, 7.60, 7.82, 8.32, 11.85.

Example 59(12)

N-{4-[4-amino-7-(4-piperidinyl)-7H-pyrrolo[2,3-d]pyrimidin-5-yl]phenyl}-1-benzyl-2-oxo-1,2-dihydro-3-pyridinecarboxamide (LC-MS/ELSD): (retention time: 0.61 minutes);
$^1$H-NMR (CDCl$_3$): δ 1.84-2.00, 2.06-2.16, 2.82-2.95, 3.21-3.31, 4.76-4.90, 5.10, 5.29, 6.50, 7.06, 7.30-7.50, 7.58, 7.86, 8.32, 8.65, 12.10.

Example 59(13)

N-{4-[4-amino-7-(2-azaspiro[3.3]hept-6-yl)-7H-pyrrolo[2,3-d]pyrimidin-5-yl]phenyl}-2-oxo-1-phenyl-1,2-dihydro-3-pyridinecarboxamide (LC-MS/ELSD): (retention time: 0.54 minutes);
$^1$H-NMR (DMSO-$d_6$): δ 2.60-2.70, 3.31-3.73, 5.03-5.05, 6.07, 6.72, 7.46, 7.52-7.60, 7.79, 8.10-8.12, 8.60, 12.03.

Example 60

N-(4-{4-amino-7-[cis-3-(hydroxymethyl)cyclobutyl]-7H-pyrrolo[2,3-d]pyrimidin-5-yl}phenyl)-1-[3-(aminomethyl)phenyl]-2-oxo-1,2-dihydro-3-pyridinecarboxamide bis(trifluoroacetate)

The compound (50 mg) obtained by subjecting the compound produced in Example 41 to the procedure having the same objective as in Example 2 and the corresponding carboxylic acid derivatives (29 mg) instead of the compound produced in Example 5 were used and subjected to the procedure having the same object as in Example 6→Example 57→Example 3→Example 42 to obtain the title compound (50 mg) having the following physical property values.
(LC-MS/ELSD): (retention time: 0.50 minutes);
$^1$H-NMR (CDCl$_3$): δ 2.38-2.66, 3.64, 4.24, 5.21-5.31, 6.74, 7.51-7.72, 7.80, 7.97, 8.29, 8.72, 12.05.

Example 60(1)

N-(4-{4-amino-7-[cis-3-(hydroxymethyl)cyclobutyl]-7H-pyrrolo[2,3-d]pyrimidin-5-yl}phenyl)-1-[2-(aminomethyl)phenyl]-2-oxo-1,2-dihydro-3-pyridinecarboxamide A compound (50 mg) obtained by subjecting the compound produced in Example 41 to the procedure having the same objective as in Example 2 and the corresponding carboxylic acid derivative (29 mg) instead of the compound produced in Example 5 were used and subjected to the procedure having the same object as in Example 60 to obtain the title compound having the following physical property values.
(LC-MS/ELSD): (retention time: 0.49 minutes);
$^1$H-NMR (CDCl$_3$): δ 2.43-2.53, 2.53-2.69, 3.64-3.78, 5.04-5.17, 6.63, 7.07, 7.41-7.61, 7.63-7.67, 7.78-7.83, 8.30, 8.80, 11.93.

Example 61

N-(4-{4-amino-7-[cis-3-(hydroxymethyl)cyclobutyl]-7H-pyrrolo[2,3-d]pyrimidin-5-yl}phenyl)-2-oxo-1-phenyl-1,2-dihydro-3-pyridinecarboxamide 4-chloro-5-iodo-7H-pyrrolo-[2,3-d]pyrimidine (720 mg), trans-3-[(benzyloxy)methyl]cyclobutanol (500 mg), and the corresponding carboxylic acid derivative (160 mg) instead of the compound produced in Example 5 were used and subjected to the procedure having the same object as in Example 7→Example 2→Example 6→Example 42→Example 3 to obtain the title compound (25 mg) having the following physical property values.
(LC-MS/ELSD): (retention time: 0.69 minutes);
$^1$H-NMR (CDCl$_3$): δ 2.43-2.68, 3.73, 5.04-5.13, 6.61, 7.07, 7.41-7.61, 7.64, 7.82, 8.30, 8.77, 11.97.

Examples 61(1) to 61(8)

4-chloro-5-iodo-7H-pyrrolo-[2,3-d]pyrimidine and trans-3-[(benzyloxy)methyl]cyclobutanol, or cis-3-[(benzyloxy)methyl]cyclobutanol were used and subjected to the procedure having the same object as in Example 61 to obtain the following compounds of Examples.

Example 61(1)

N-(4-{4-amino-7-[trans-3-(hydroxymethyl)cyclobutyl]-7H-pyrrolo[2,3-d]pyrimidin-5-yl}phenyl)-2-oxo-1-phenyl-1,2-dihydro-3-pyridinecarboxamide (LC-MS/ELSD): (retention time: 0.70 minutes);
$^1$H-NMR (CD$_3$OD): δ 2.43-2.56, 2.63-2.76, 3.65, 3.74, 5.42-5.55, 6.75, 7.48-7.61, 7.71, 7.83, 7.96-7.99, 8.25, 8.72.

Example 61(2)

N-(4-{4-amino-7-[cis-3-(hydroxymethyl)cyclobutyl]-7H-pyrrolo[2,3-d]pyrimidin-5-yl}phenyl)-1-(4-methylphenyl)-2-oxo-1,2-dihydro-3-pyridinecarboxamide (LC-MS/ELSD): (retention time: 0.71 minutes);
$^1$H-NMR (CDCl$_3$): δ 2.45, 2.47-2.48, 2.56-2.66, 3.74, 5.07-5.11, 5.27, 6.60, 7.09, 7.26-7.44, 7.63, 7.82, 8.30, 8.75, 12.01.

Example 61(3)

N-(4-{4-amino-7-[cis-3-(hydroxymethyl)cyclobutyl]-7H-pyrrolo[2,3-d]pyrimidin-5-yl}phenyl)-1-(4-fluorophenyl)-2-oxo-1,2-dihydro-3-pyridinecarboxamide (LC-MS/ELSD): (retention time: 0.70 minutes);
$^1$H-NMR (CDCl$_3$): δ 2.47-2.67, 3.74, 5.07-5.13, 5.16, 6.62, 7.09, 7.26-7.46, 7.62, 7.82, 8.30, 8.76, 11.90.

Example 61(4)

N-(4-{4-amino-7-[cis-3-(hydroxymethyl)cyclobutyl]-7H-pyrrolo[2,3-d]pyrimidin-5-yl}phenyl)-4,6-dimethyl-2-oxo-1-phenyl-1,2-dihydro-3-pyridinecarboxamide (LC-MS/ELSD): (retention time: 0.70 minutes);
$^1$H-NMR (CDCl$_3$): δ 2.03, 2.45-2.65, 2.03, 3.73, 5.04-5.10, 6.27, 7.04, 7.20-7.24, 7.39, 7.53-7.62, 7.75, 8.29, 12.06.

Example 61(5)

N-(4-{4-amino-7-[cis-3-(hydroxymethyl)cyclobutyl]-7H-pyrrolo[2,3-d]pyrimidin-5-yl}phenyl)-1-benzyl-2-oxo-1,2-dihydro-3-pyridinecarboxamide (LC-MS/ELSD): (retention time: 0.72 minutes);
$^1$H-NMR (CDCl$_3$): δ 2.45-2.69, 3.74, 5.04-5.13, 5.29, 6.50, 7.09, 7.30-7.48, 7.59, 7.85, 8.31, 8.65, 12.10.

Example 61(6)

N-(4-{4-amino-7-[cis-3-(hydroxymethyl)cyclobutyl]-7H-pyrrolo[2,3-d]pyrimidin-5-yl}phenyl)-1-(3-fluorobenzyl)-2-oxo-1,2-dihydro-3-pyridinecarboxamide (LC-MS/ELSD): (retention time: 0.68 minutes);
$^1$H-NMR (CDCl$_3$): δ 2.42-2.55, 2.58-2.69, 3.75, 5.00-5.21, 5.28, 6.53, 6.98-7.15, 7.32-7.41, 7.46, 7.59, 7.85, 8.32, 8.67, 12.03.

Example 61(7)

N-(4-{4-amino-7-[cis-3-(hydroxymethyl)cyclobutyl]-7H-pyrrolo[2,3-d]pyrimidin-5-yl}phenyl)-2-oxo-1-[(1 S)-1-phenylethyl]-1,2-dihydro-3-pyridinecarboxamide (LC-MS/ELSD): (retention time: 0.76 minutes);
$^1$H-NMR (CDCl$_3$): δ 1.81, 2.46-2.68, 3.75, 5.07-5.13, 6.45, 6.55-7.09, 7.09, 7.33-7.49, 7.86, 8.32, 8.61, 12.21.

Example 61(8)

N-(5-{4-amino-7-[cis-3-(hydroxymethyl)cyclobutyl]-7H-pyrrolo[2,3-d]pyrimidin-5-yl}-2-pyridinyl)-2-oxo-1-phenyl-1,2-dihydro-3-pyridinecarboxamide (LC-MS/ELSD): (retention time: 0.65 minutes);
$^1$H-NMR (CDCl$_3$): δ 2.41-2.72, 3.74, 5.03, 5.04-5.16, 6.59, 7.12, 7.39-7.46, 7.48-7.60, 7.67, 7.81, 8.32, 8.40-8.49, 8.73, 12.42.

Example 62

N-(4-{4-amino-7-[cis-3-(aminomethyl)cyclobutyl]-7H-pyrrolo[2,3-d]pyrimidin-5-yl}phenyl)-2-oxo-1-phenyl-1,2-dihydro-3-pyridinecarboxamide 4-chloro-5-iodo-7H-pyrrolo[2,3-d]pyrimidine, trans-3-[(benzyloxy)methyl]cyclobutanol and the corresponding carboxylic acid derivative instead of the compound produced in Example 5 were used and subjected to the procedure having the same object as in Example 7→Example 2→Example 6→Example 42→Example 57→Example 3 to obtain the title compound having the following physical property values.

(LC-MS/ELSD): (retention time: 0.62 minutes);
$^1$H-NMR (CDCl$_3$): δ 2.08-2.24, 2.66-2.88, 5.10, 5.16-5.22, 6.62, 7.12, 7.41-7.46, 7.54-7.67, 7.82, 8.36, 8.77, 11.99.

Example 63

N-[4-(4-amino-7-{cis-3-[(dimethylamino)methyl]cyclobutyl}-7H-pyrrolo[2,3-d]pyrimidin-5-yl)phenyl]-2-oxo-1-phenyl-1,2-dihydro-3-pyridinecarboxamide bis(trifluoroacetate)

The compound (20 mg) produced in Example 62 was used and subjected to the procedure having the same object as in Example 9 to obtain the title compound (10 mg) having the following physical property values.
(LC-MS/ELSD): (retention time: 0.59 minutes);
$^1$H-NMR (CDCl$_3$): δ 2.27-2.47, 2.67-2.72, 2.76, 2.77, 3.27-3.33, 4.92, 5.13-5.25, 6.74, 7.45-7.88, 8.14, 8.27-8.35, 8.60, 9.36, 12.10.

Example 64

N-[4-(4-amino-7-phenyl-7H-pyrrolo-[2,3-d]pyrimidin-5-yl)phenyl]-2-oxo-1-phenyl-1,2-dihydro-3-pyridinecarboxamide 4-chloro-5-iodo-7H-pyrrolo-[2,3-d]pyrimidine, 4-(4,4,5,5-tetramethyl-1,3,2-dioxaborolan-2-yl)aniline and the corresponding carboxylic acid derivative instead of the compound produced in Example 5 were used and subjected to the procedure having the same object as in Example 27→Example 2→Example 6→Example 3 to obtain the title compound (23 mg) having the following physical property values.

(LC-MS/ELSD): (retention time: 4.27 minutes);
$^1$H-NMR (DMSO-d$_6$): δ 6.62-6.78, 7.38-7.42, 7.53-7.60, 7.80-7.88, 8.13, 8.28, 8.62, 12.08.

Example 65

4-chloro-7-(cyclopent-3-ene-1-yl)-5-iodo-7H-pyrrolo-[2,3-d]pyrimidine 4-chloro-5-iodo-7H-pyrrolo-[2,3-d]pyrimidine (900 mg) and cyclopenta-3-enol (CAS registration No.: 14320-38-8) (300 mg) were used and subjected to the procedure having the same object as in Example 7 to obtain the title compound having the following physical property values.
$^1$H-NMR (DMSO-d$_6$): δ 2.60-2.64, 2.89-2.95, 5.49-5.53, 5.88, 7.87, 8.65.

Example 66

(1R,2S)-4-(4-chloro-5-iodo-7H-pyrrolo-[2,3-d]pyrimidine-7-yl)cyclopentane-1,2-diol The compound (400 mg) produced in Example 65 was dissolved in acetone (10 mL), and water (2.5 mL) and N-methyl morpholine N-oxide (370 mg) were added thereto. The resulting mixture was stirred for five minutes. Then, a tert-butanol solution (1 mL) dissolving osmium tetroxide (30 mg) was dripped and stirred at room temperature for 2.5 hours. The reaction solution was concentrated under reduced pressure. The solvent was distilled off under reduced pressure. The obtained residue was dissolved in ethyl acetate, 1 mol/L sodium thiosulfate aqueous solution, and washed with a saturated saline solution. The organic layer was dried over sodium sulfate, filtered, and then concentrated under reduced pressure to obtain the title compound (360 mg) having the following physical property values.
$^1$H-NMR (DMSO-d$_6$): δ 1.99-2.15, 4.24, 4.66, 5.41-5.45, 8.14, 8.62.

Example 67

4-chloro-7-[(3aR,6aS)-2,2-dimethyltetrahydro-3aH-cyclopenta[d][1,3]dioxole-5-yl]-5-iodo-7H-pyrrolo-[2,3-d]pyrimidine The compound (350 mg) produced in Example 66 was dissolved in acetone (10 mL), and p-toluenesulfonic acid (small amount) and 2,2-dimethoxypropane (0.2 mL) were added thereto, and the resulting mixture was stirred at room temperature for whole day and night. The reaction solution was concentrated under reduced pressure, and the solvent was distilled off under reduced pressure. The obtained residue was placed into water, followed by extraction with ethyl acetate. The organic layer was dried over sodium sulfate, filtered, and then concentrated under reduced pressure to obtain the title compound (310 mg) having the following physical property values.

$^1$H-NMR (DMSO-$d_6$): δ 1.27, 1.43, 2.17, 4.75, 5.21-5.28, 8.19, 8.65.

Example 68 rel-N-(4-{4-amino-7-[(3R,4S)-3,4-dihydroxycyclopentyl]-7H-pyrrolo[2,3-d]pyrimidin-5-yl}phenyl)-2-oxo-1-phenyl-1,2-dihydro-3-pyridinecarboxamide hydrochloride The compound (300 mg) produced in Example 67, 4-(4,4,5,5-tetramethyl-1,3,2-dioxaborolan-2-yl)aniline (230 mg), and the corresponding carboxylic acid derivative (56 mg) instead of the compound produced in Example 5 were used and subjected to the procedure having the same object as in Example 2 Example 6→Example 3→Example 55 to obtain the title compound (36 mg) having the following physical property values.

(LC-MS/ELSD): (retention time: 3.86 minutes);
$^1$H-NMR (DMSO-$d_6$): δ 2.12-2.19, 4.25, 4.68-4.70, 5.39-5.45, 6.74, 7.15, 7.46-7.66, 7.82, 8.13, 8.30, 8.61, 12.03.

Example 69 methyl cis-4-hydroxycyclohexane carboxylate cis-4-hydroxycyclohexane carboxylic acid (CAS registration No.: 3685-22-1) (1.5 mg) was dissolved in methanol (25 mL), and sulfuric acid (0.1 mL) was added thereto at 0° C. The resulting mixture was stirred for 10 minutes. The reaction solution was stirred at room temperature for whole day and night. The reaction solution was concentrated under reduced pressure and methanol was distilled off. The obtained residue was diluted with a mixed solution of a saturated sodium hydrogen carbonate aqueous solution/ethyl acetate (1:1). The organic layer was dried over sodium sulfate, filtrated, and then concentrated under reduced pressure. The obtained residue was purified by column chromatography on silica gel (hexane:ethyl acetate=100:0→30:70) to obtain the title compound (1.3 g) having the following physical property values.

$^1$H-NMR (CDCl$_3$): δ 1.35, 1.64-1.70, 1.91-2.02, 2.36-2.44, 3.68, 3.89-3.90.

Example 70

N-(4-{7-[(cis-4-{[tert-butyl(dimethyl)silyl]oxy}cyclohexyl)methyl]-4-chloro-7H-pyrrolo[2,3-d]pyrimidin-5-yl}phenyl)-2-oxo-1-phenyl-1,2-dihydro-3-pyridinecarboxamide The compound (1.3 g) produced in Example 69, 4-chloro-5-iodo-7H-pyrrolo-[2,3-d]pyrimidine (1.0 mg), 4-(4,4,5,5-tetramethyl-1,3,2-dioxaborolan-2-yl)aniline (260 mg), and the compound (140 mg) produced in Example 5 were used and subjected to the procedure having the same object as in Example 53→Example 31→Example 7→Example 2→Example 6 to obtain the title compound (260 mg) having the following physical property values.

$^1$H-NMR (CDCl$_3$): δ 0.00, 0.86, 1.35-1.41, 1.46-1.60, 3.93, 4.13, 6.58, 7.20, 7.39-7.63, 7.76, 8.62, 8.74, 11.93.

Example 71

N-(4-{4-amino-7-[(cis-4-hydroxycyclohexyl)methyl]-7H-pyrrolo[2,3-d]pyrimidin-5-yl}phenyl)-2-oxo-1-phenyl-1,2-dihydro-3-pyridinecarboxamide The compound (200 mg) produced in Example 70 was subjected to the procedure having the same object as in Example 3→Example 55 to obtain the title compound (60 mg) having the following physical property values.

(LC-MS/ELSD): (retention time: 0.69 minutes);
$^1$H-NMR (CDCl$_3$): δ 1.19-1.26, 1.45-1.57, 1.77-1.79, 1.98-2.04, 3.97-4.03, 4.10, 5.08, 6.11, 6.92, 7.41-7.46, 7.54-7.66, 7.81, 8.32, 8.76, 11.96.

Example 71(1)

N-(4-{4-amino-7-[(trans-4-hydroxycyclohexyl)methyl]-7H-pyrrolo[2,3-d]pyrimidin-5-yl}phenyl)-2-oxo-1-phenyl-1,2-dihydro-3-pyridinecarboxamide The corresponding ester derivative instead of the compound produced in Example 69 and the corresponding carboxylic acid derivative instead of the compound produced in Example 5 were used and subjected to the procedure having the same object as in Example 70→Example 71 to obtain the title compound having the following physical property values.

(LC-MS/ELSD): (retention time: 0.67 minutes);
$^1$H-NMR (CDCl$_3$): δ 1.07-1.40, 1.70-1.88, 1.97-2.00, 3.53-3.63, 4.05, 5.09, 6.14, 6.90, 7.41-7.46, 7.54-7.66, 7.82, 8.32, 8.76, 11.97.

Example 72

N-(4-{4-amino-7-[(cis-4-aminocyclohexyl)methyl]-7H-pyrrolo[2,3-d]pyrimidin-5-yl}phenyl)-2-oxo-1-phenyl-1,2-dihydro-3-pyridinecarboxamide bis(trifluoroacetate)

The corresponding ester derivative instead of the compound produced in Example 69, 4-chloro-5-iodo-7H-pyrrolo-[2,3-d]pyrimidine (200 mg), 4-(4,4,5,5-tetramethyl-1,3,2-dioxaborolan-2-yl)aniline (200 mg), and the compound (130 mg) produced in Example 5 were used and subjected to the procedure having the same object as in Example 53→Example 31→Example 7→Example 2→Example 6→Example 55→Example 57→Example 3 to obtain the title compound (110 mg) having the following physical property values.

(LC-MS/ELSD): (retention time: 0.60 minutes);
$^1$H-NMR (CD$_3$OD): δ 1.47-1.66, 1.78-1.85, 2.25, 4.29, 6.75, 7.39, 7.49-7.51, 7.56-7.62, 7.81, 7.98, 8.25, 8.71, 12.17.

Example 72(1)

N-(4-{4-amino-7-[(trans-4-aminocyclohexyl)methyl]-7H-pyrrolo[2,3-d]pyrimidin-5-yl}phenyl)-2-oxo-1-phenyl-1,2-dihydro-3-pyridinecarboxamide bis(trifluoroacetate)

The compound (300 mg) produced in Example 70 was used and subjected to the procedure having the same object as in Example 55→Example 57→Example 3 to obtain the title compound (70 mg) having the following physical property values.

(LC-MS/ELSD): (retention time: 0.61 minutes);
$^1$H-NMR (DMSO-$d_6$): δ 1.23-1.38, 1.77-1.80, 1.99-2.06, 3.12-3.13, 4.21, 6.76, 7.46, 7.48-7.59, 7.61, 7.98, 8.29, 8.71, 12.18.

Example 73 benzyl (3-methylidene cyclobutyl)carbamate 3-methylidene cyclobutane carboxylic acid (CAS registration No.: 15760-36-8) (1.0 g) and triethylamine (1.6 mL) were dissolved in a mixed solution of 1,4-dioxane (2 mL) and acetonitrile (4 mL), and diphenylphosphoryl azide (1.9 mL) was added thereto. The resulting mixture was stirred at room temperature for 15 minutes. Then, the temperature of the reaction solution was gradually increased to 75° C. while stirring the reaction solution. After generation of gas (nitrogen) was checked, and the temperature of the reaction solution was increased to 100° C. Benzyl alcohol (2.0 mL) was added to the reaction mixture, and the mixture was stirred for 19 hours. The temperature of the reaction solution was returned to room temperature by cooling. Then, the solvent was distilled off by concentration under reduced pressure. Ethyl acetate was added to the obtained residue. The residue was washed with a saturated aqueous solution of ammonium chloride, a saturated aqueous solution of sodium hydrogen carbonate, and a saturated saline solution, sequentially in this order, dried over sodium sulfate, and filtered, followed by concentration under reduced pressure. The obtained residue was purified by column chromatography on silica gel (hexane:ethyl acetate=100:0→30:70) to obtain the title compound (1.2 g) having the following physical property values.
$^1$H-NMR (CDCl$_3$): δ 2.57-2.63, 2.99-3.04, 4.19-4.22, 4.83-4.85, 5.09, 7.26-7.36.

Example 74 benzyl[3-hydroxy-3-(hydroxymethyl)cyclobutyl]carbamate

The compound (1.0 g) produced in Example 73 was dissolved in a mixed solution of tert-butanol (15 mL) and water (15 mL), and AD-mixα (7.0 g) was added thereto at 0° C. The mixture was stirred at room temperature for 16 hours. The reaction solution was cooled to 0° C., and sodium carbonate was added to the reaction solution. The reaction solution was stirred at room temperature for one hour. The reaction solution was diluted with water, and extracted with ethyl acetate. The organic layer was dried over sodium sulfate, filtered, and then concentrated under reduced pressure to obtain the title compound (0.76 g) having the following physical property values.
$^1$H-NMR (DMSO-$d_6$): (peak strength cis/trans=1:2), δ 1.96, 2.30, 3.20, 3.52, 4.62, 4.71, 4.99, 7.30-7.39 (trans configuration), 1.80, 2.30, 3.25, 4.12, 4.65, 4.78, 4.99, 7.30-7.39 (cis configuration).

Example 75

3-amino-1-(hydroxymethyl)cyclobutanol

The compound (750 mg) produced in Example 74 was dissolved in a mixed solution of THF (7.5 mL) and methanol (7.5 mL), and palladium/carbon (120 mg) was added thereto. The resultant solution was stirred at room temperature for one hour under hydrogen atmosphere. The reaction solution was filtered through celite and concentrated under reduced pressure to obtain the title compound (0.76 g) having the following physical property values.
$^1$H-NMR (DMSO-$d_6$): δ 1.53-1.58, 1.71-1.75, 1.99-2.04, 2.27-2.32, 2.76-2.84, 3.39-3.46.

Example 76

3-(4-chloro-7H-pyrrolo[2,3-d]pyrimidine-7-yl)-1-(hydroxymethyl)cyclobutanol

The compound (490 mg) produced in Example 75 was dissolved in ethanol (10 mL), and 2-(4,6-dichloropyrimidine-5-yl)acetaldehyde (300 mg) and diisopropylethylamine (0.93 mL) were added thereto at room temperature. The resulting mixture was refluxed for 4.5 hours. The reaction solution was allowed to cool and the temperature of the reaction solution was returned to room temperature. Then, trifluoroacetic acid (1.4 mL) was added to the reaction solution and refluxed for one hour. The temperature of the reaction solution was returned to room temperature, and a saturated aqueous solution of sodium hydrogen carbonate was added thereto, and then ethanol was distilled off by concentration under reduced pressure. The residue was extracted with ethyl acetate, and the organic layer was washed with a saturated saline solution, dried over sodium sulfate, filtered, and concentrated under reduced pressure. The obtained residue was purified by column chromatography on silica gel (dichloromethane:methanol containing 10% ammonium=99:1→90:10) to obtain the title compound (340 mg) having the following physical property values.
$^1$H-NMR (DMSO-$d_6$): (peak strength cis/trans=1:2), δ 2.42, 2.70, 3.16, 2.78, 4.89-4.95, 5.17, 5.49, 6.69, 7.91, 8.63 (trans configuration), 2.45, 2.78, 3.33, 3.41, 4.89-4.95, 5.31, 4.91, 6.73, 8.02, 8.62 (cis configuration).

Example 77

3-(4-chloro-5-iodo-7H-pyrrolo[2,3-d]pyrimidine-7-yl)-1-(hydroxymethyl)cyclobutanol The compound (330 mg) produced in Example 76 was dissolved in DMF (5.0 mL), and N-iodosuccinimide (580 mg) was added thereto. The resulting mixture was stirred at 60° C. for 2.5 hours. The reaction solution was diluted with ethyl acetate, and washed with an aqueous solution of sodium carbonate and a saturated saline solution. The organic layer was dried over sodium sulfate, filtered, and then concentrated under reduced pressure. The obtained residue was washed with tert-butyl methyl ether and hexane to obtain the title compound (310 mg) having the following physical property values.
$^1$H-NMR (DMSO-$d_6$): (peak strength cis/trans=1:2), δ 2.25, 2.60, 3.39-3.40, 4.88-4.92, 5.29, 5.40, 8.23, 8.63 (trans configuration), 2.34, 2.76, 3.39-3.40, 4.88-4.92, 4.89, 5.16, 8.13, 8.62 (cis configuration).

Example 78

N-(4-{4-amino-7-[3-hydroxy-3-(hydroxymethyl)cyclobutyl]-7H-pyrrolo[2,3-d]pyrimidin-5-yl}phenyl)-2-oxo-1-phenyl-1,2-dihydro-3-pyridinecarboxamide The compound (50 mg) produced in Example 77, 4-(4,4,5,5-tetramethyl-1,3,2-dioxaborolan-2-yl)aniline, and the corresponding carboxylic acid derivative instead of the compound produced in Example 5 were used and subjected to the procedure having the same object as in Example 2→Example 6→Example 3 to obtain the title compound (50 mg) having the following physical property values.

(LC-MS/ELSD): (retention time: 0.60 minutes);

$^1$H-NMR (DMSO-d$_6$): (peak strength cis/trans=1:2), δ 2.25, 2.60, 3.39-3.40, 4.88-4.92, 5.16, 5.40, 6.01, 6.73, 7.44-7.61, 7.79-7.82, 8.10-8.13, 8.59, 12.40 (trans configuration), 2.34, 2.76, 3.39-3.40, 4.88-4.92, 4.89, 5.29, 6.01, 6.73, 7.44-7.61, 7.79-7.82, 8.10-8.13, 8.59, 12.40 (cis configuration).

Example 79

N-{4-[4-amino-7-(3-oxocyclobutyl)-7H-pyrrolo[2,3-d]pyrimidin-5-yl]phenyl}-2-oxo-1-phenyl-1,2-dihydro-3-pyridinecarboxamide The compound (30 mg) produced in Example 78 was dissolved in a mixed solution of THF (2.5 mL) and water (0.5 mL), and sodium periodate (24 mg) was added thereto at 0° C. The resulting mixture was stirred at room temperature for four hours. The reaction solution was concentrated under reduced pressure. The obtained residue was diluted with ethyl acetate, and washed with water and a saturated saline solution. The organic layer was dried over sodium sulfate, filtered, and concentrated under reduced pressure to obtain title compound (20 mg) having the following physical property values.

(LC-MS/ELSD): (retention time: 0.72 minutes);

$^1$H-NMR (CDCl$_3$): δ 3.65-3.83, 5.13, 5.40-5.44, 6.62, 7.05, 7.42-7.45, 7.52-7.66, 7.83, 8.32, 8.77, 11.99.

Example 80

3-(4-chloro-5-iodo-7H-pyrrolo[2,3-d]pyrimidine-7-yl)cyclobutanol

The compound (140 mg) obtained by subjecting the compound produced in Example 77 to the procedure having the same object as in Example 79 was dissolved in a mixed solution of methanol (3.0 mL) and dichloromethane (3.0 mL). Sodium borohydride (15 mg) was added at −20° C. to the resulting mixture. The resulting mixture was stirred at room temperature for two hours. The reaction solution was concentrated under reduced pressure. A saturated aqueous solution of ammonium chloride was added to the obtained residue, followed by extraction with ethyl acetate. The organic layer was washed with water and a saturated saline solution, dried over sodium sulfate, filtered, and concentrated under reduced pressure. The obtained residue was partially purified by column chromatography on silica gel (dichloromethane:methanol=70:30) to obtain a crude product (110 mg) including the title compound having the following physical property value.

MS (M+H): 350.

Example 81

N-{4-[4-amino-7-(3-hydroxycyclobutyl)-7H-pyrrolo[2,3-d]pyrimidin-5-yl]phenyl}-2-oxo-1-phenyl-1,2-dihydro-3-pyridinecarboxamide The crude product (100 mg) produced in Example 80, 4-(4,4,5,5-tetramethyl-1,3,2-dioxaborolan-2-yl)aniline and the corresponding carboxylic acid derivative instead of the compound produced in Example 5 were used and subjected to the procedure having the same object as in Example 78 to obtain the title compound (25 mg) having the following physical property values.

(LC-MS/ELSD): (retention time: 0.67 minutes);

$^1$H-NMR (CDCl$_3$): (mixture of cis configuration and trans configuration), δ 2.63-2.57, 3.06-3.13, 3.73-3.76, 3.89 (cis configuration)/4.29 (trans configuration), 4.72-4.76, 5.12, 6.62, 7.04, 7.41-7.45, 7.54-7.61, 7.65, 7.82, 8.31, 8.77, 11.98.

Example 82

4-iodo-2-methoxypyridine-3-carbaldehyde

Under the stream of nitrogen, a THF (500 mL) solution of diisopropylamine (25 g) was added into a 2 L-four-necked flask. The solution was cooled to −25° C., and n-butyl lithium-hexane solution (1.57 mol/L) (157 mL) was dropped to the solution for 20 minutes (−25° C.→−15° C.), and the solution was stirred at −10° C. for 30 minutes. The resulting solution was cooled to −66° C., and a THF (200 mL) solution of 2-fluoro-3-iodopyridine (CAS registration No.: 113975-22-7) (50 g) was dropped thereto for 25 minutes, and stirred at −60° C. for two hours. The resulting solution was cooled to −66° C., and ethyl formate (18.3 g) was dropped thereto for 10 minutes. Then, 28% solution of sodium methoxide methanol solution (53.2 g) in methanol (100 mL) was dropped, and lifted up from dry ice bath. The resulting product was naturally cooled to room temperature, and ice water (100 mL) was dropped thereto. A saturated saline solution (1 L) was added thereto. The resulting solution was extracted with ethyl acetate (1 L), and washed with water (700 mL) and a saturated saline solution (700 mL). The water layer was combined and extracted with ethyl acetate (500 mL×2), and washed with water (500 mL) and a saturated saline solution (500 mL). The organic layer was combined and dried over anhydrous sodium sulfate, and the solvent was removed by evaporation under reduced pressure. The obtained residue was purified by column chromatography on silica gel (hexane:ethyl acetate=9:1→6:1→5:1→4:1→3:1) to obtain the title compound (44 g) having the following physical property values.

Example 83

4-iodo-2-oxo-1,2-dihydropyridine-3-carbaldehyde

Under the stream of nitrogen, an acetonitrile (600 mL) solution of the compound (44 g) produced in Example 82 was added into a 1 L-four-necked flask. Then, sodium iodide (75 g) was added thereto for two minutes. The mixture was stirred at room temperature for 15 minutes. Then, trimethylchlorosilane (54 g) was dropped for 25 minutes, and the mixture was stirred at room temperature for four hours. Under reduced pressure, the solvent was distilled off under reduced pressure, and ethyl acetate (100 mL), a saturated aqueous solution of sodium hydrogen carbonate (200 mL), and water (100 mL) were added thereto. Then resulting product was subjected to ultrasonic treatment, and then filtered to obtain a title compound (14 g). The filtrate was extracted with ethyl acetate (500 mL×2) and THF (500 mL×2), and washed with saturated saline solution (500 mL). The resulting solution was dried over anhydrous sodium sulfate, and then the solvent was removed by evaporation under reduced pressure and washed with ethyl acetate (100 mL) to obtain the title compound (12 g). The title compound (27 g) was obtained together.

Example 84

1-(4-fluorophenyl)-4-iodo-2-oxo-1,2-dihydropyridine-3-carbaldehyde

A toluene (1.2 L) suspension of the compound (25 g) produced in Example 83, 4-fluorophenyl boronic acid (41 g), copper acetate (II) (36 g), myristic acid (90 g), and 2,6-dimethyl pyridine (85 g) were sequentially added into a 3 L-four-necked flask, and stirred at room temperature for 16 hours. Furthermore, 4-fluorophenyl boronic acid (7.0 g) was added thereto, and the resulting mixture was stirred at room temperature for two days. The resulting mixture was filtered through celite, and the solvent was removed by evaporation under reduced pressure. Ethyl acetate (1 L) and water (500 mL) were added thereto, filtered through celite, and then washed with 1 mol/L hydrochloric acid (600 mL), water (500 mL), and a saturated saline solution (500 mL). The resulting product was dried over anhydrous sodium sulfate, and the solvent was removed by evaporation under reduced pressure. The obtained residue was purified by column chromatography on silica gel (dichloromethane:ethyl acetate=9:1→2:1). The resulting product was washed with diisopropyl ether (400 mL) to obtain the title compound (19 g).

Example 85

1-(4-fluorophenyl)-4-iodo-2-oxo-1,2-dihydropyridine-3-carboxylic acid

Under the stream of nitrogen, the compound (20 g) produced in Example 84, a THF (100 mL), tert-butanol (100 mL), and water (100 mL) were added into a 1 L-four-necked flask. The resulting mixture was ice-cooled, and, sodium dihydrogen phosphate (17 g), and a 2-methyl-2-buten-THF solution (2 mol/L) (88 mL) were sequentially added, and then 2 g each of sodium chlorite (12 g) was placed separately. The resulting mixture was stirred at room temperature for 1.5 hours. THF (150 mL) and water (900 mL) were added thereto, and the mixture was washed with ethyl acetate (600 mL). To the water layer, 6 mol/L hydrochloric acid (50 mL) and THF (600 mL) were added. The precipitate was collected by filtration, and washed with water (300 mL), and then dried to obtain the title compound (12 g). The filtrate was extracted with THF (400 mL×2), and washed with water a saturated saline solution (500 mL). The resulting product was dried over anhydrous sodium sulfate, and then solvent was removed by evaporation under reduced pressure. The resulting product was washed with ethyl acetate (200 mL) to obtain the title compound (3.9 g). The title compound (16 g) was obtained together.

Example 86

N-[4-(4-amino-7-cyclopentyl-7H-pyrrolo[2,3-d]pyrimidin-5-yl)phenyl]-1-(4-fluorophenyl)-4-iodo-2-oxo-1,2-dihydro-3-pyridinecarboxamide 4-(4-amino-7-cyclopentyl-7H-pyrrolo[2,3-d]pyrimidin-5-yl)aniline (570 mg) and the compound (700 mg) produced in Example 85 were used and subjected to the procedure having the same object as in Example 6 to obtain the title compound (360 mg) having the following physical property values.
TLC: Rf 0.40 (ethyl acetate:methanol=19:1);
$^1$H-NMR (DMSO-$d_6$): δ 1.62-1.78, 1.80-2.00, 2.04-2.21, 5.03-5.19, 6.83, 7.33-7.82, 8.31, 10.59.

Example 86(1)

N-[4-(4-amino-7-cyclopentyl-7H-pyrrolo[2,3-d]pyrimidin-5-yl)phenyl]-1-(4-fluorophenyl)-2-oxo-4-(3H-[1,2,3]triazolo[4,5-b]pyridine-3-yloxy)-1,2-dihydro-3-pyridinecarboxamide As a byproduct of Example 86, the title compound (300 mg) having the following physical property values was obtained.
TLC: Rf 0.17 (ethyl acetate:methanol=19:1);
(LC-MS/ELSD): (retention time: 0.83 minutes);

Example 87

N-[4-(4-amino-7-cyclopentyl-7H-pyrrolo[2,3-d]pyrimidin-5-yl)phenyl]-4-ethoxy-1-(4-fluorophenyl)-2-oxo-1,2-dihydro-3-pyridinecarboxamide

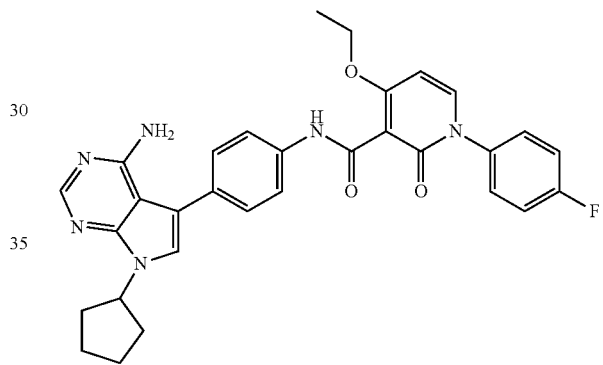

The compound (110 mg) produced in Example 86 was dissolved in a mixed solution of THF (2 mL) and ethanol (2 mL), 20% sodium ethoxide-ethanol solution (180 mg) was added thereto. The resulting mixture was stirred at room temperature for two hours. The reaction solution was concentrated under reduced pressure. To the obtained residue, a saturated aqueous solution of ammonium chloride was added, followed by extraction with ethyl acetate. The organic layer was dried over magnesium sulfate, filtered, and then concentrated under reduced pressure. The obtained residue was purified by column chromatography on silica gel (ethyl acetate:methanol=100:0→80:20) to obtain the title compound (31 mg) having the following physical property values.
TLC: Rf 0.32 (ethyl acetate:methanol=9:1);
$^1$H-NMR (CDCl$_3$): δ 1.74-2.00, 2.20-2.32, 5.08, 5.15-5.28, 6.37, 7.01, 7.20-7.30, 7.35-7.43, 7.51, 7.78, 8.32, 11.38.

Example 87(1)

N-[4-(4-amino-7-cyclopentyl-7H-pyrrolo[2,3-d]pyrimidin-5-yl)phenyl]-1-(4-fluorophenyl)-4-hydroxy-2-oxo-1,2-dihydro-3-pyridinecarboxamide As a byproduct of Example 87, the title compound (3.6 mg) having the following physical property values was obtained.

TLC: Rf 0.57 (ethyl acetate:methanol=9:1);
$^1$H-NMR (CHCl$_3$): δ 1.75-1.99, 2.21-2.33, 5.19, 5.18-5.24, 6.34, 7.08, 7.18-7.28, 7.33-7.37, 7.57, 8.34, 11.84.

Example 88 ethyl 5-bromo-1-ethyl-2-hydroxy-1,6-dihydropyridine-3-carboxylate 5-bromo-2-hydroxypyridine-3-carboxylic acid (CAS registration No.: 104612-36-4) (3.7 g) was dissolved in ethanol in a sealed tube. To the resulting solution, cesium carbonate (8.0 g) and iodoethane (5.9 g) were added. The resulting mixture was stirred at 80° C. for three hours. The reaction solution was concentrated under reduced pressure. The obtained residue was purified by column chromatography on silica gel (hexane:ethyl acetate=80:20→50:50) to obtain the title compound (2.2 g) having the following physical property values.
$^1$H-NMR (CDCl$_3$): δ 1.36-1.41, 4.00-4.05, 4.34-4.39, 7.63, 8.13.

Example 89 ethyl 2-acetyl-1-ethyl-2-oxo-1,2-dihydropyridine-3-carboxylate

The compound (1.8 g) produced in Example 89 was dissolved in anhydrous DMF (20 mL), and palladium acetate (75 mg) and 1,3-bis(diphenylphosphino)propane (410 mg) were added thereto. The resulting mixture was subjected to deaeration for 10 minutes, and then subjected to nitrogen substitution, and butyl vinyl ether (4.3 mL) and triethylamine (2.4 mL) were added thereto. Under nitrogen atmosphere, the reaction solution was stirred at 120° C. for 72 hours. The reaction solution was allowed to cool to room temperature, and then distilled with water and ethyl acetate. The organic layer was dried over sodium sulfate, filtered, and concentrated under reduced pressure. The obtained residue was purified by column chromatography on silica gel (hexane:ethyl acetate=80:20→33:67) to obtain the title compound (1.2 g) having the following physical property values.
$^1$H-NMR (CDCl$_3$): δ 1.37-1.45, 2.50, 4.07-4.15, 4.36-4.43, 8.35, 8.59.

Example 90

5-acetyl-N-[4-(4-amino-7-cyclopentyl-7H-pyrrolo[2,3-d]pyrimidin-5-yl)phenyl]-1-ethyl-2-oxo-1,2-dihydro-3-pyridinecarboxamide 4-(4-chloro-7-cyclopentyl-7H-pyrrolo[2,3-d]pyrimidin-5-yl)aniline (140 mg) and the compound (240 mg) produced in Example 89 were used and subjected to the procedure having the same object as in Example 23→Example 6→Example 3 to obtain the title compound (120 mg) having the following physical property values.
(LC-MS/ELSD): (retention time: 0.82 minutes);
$^1$H-NMR (CDCl$_3$): δ 1.50, 1.78-1.92, 2.22-2.28, 2.59, 4.17-4.26, 5.06, 5.21-5.25, 7.04, 7.48-7.51, 7.83-7.86, 8.34, 8.43, 9.09, 11.79.

Example 91 tert-butyl 5-bromo-2-hydroxy nicotinate 5-bromo-2-hydroxypyridine-3-carboxylic acid (2.0 mg) and thionyl chloride (1.3 mL) were dissolved in a mixed solution of THF (10 mL) and dichloromethane (10 mL), and the resulting mixed solution was stirred at room temperature for 16 hours. The reaction solution was concentrated under reduced pressure. To the obtained residue, triethylamine (4.5 mL) was added and then tert-butanol (20 mL) was added. The resulting mixture was stirred at room temperature for one hour. The reaction solution was placed in ice water, and the resulting mixture was extracted with ethyl acetate. The organic layer was dried over sodium sulfate, filtered, and then concentrated under reduced pressure. The obtained residue was purified by column chromatography on silica gel (hexane:ethyl acetate=100:0→40:60) to obtain the title compound (1.5 g) having the following physical property values.
$^1$H-NMR (CDCl$_3$): δ 1.62, 8.18, 8.39, 11.53.

Example 92

N-[4-(4-amino-7-methyl-7H-pyrrolo[2,3-d]pyrimidin-5-yl)phenyl]-5-cyclopropyl-2-oxo-1-phenyl-1,2-dihydro-3-pyridinecarboxamide

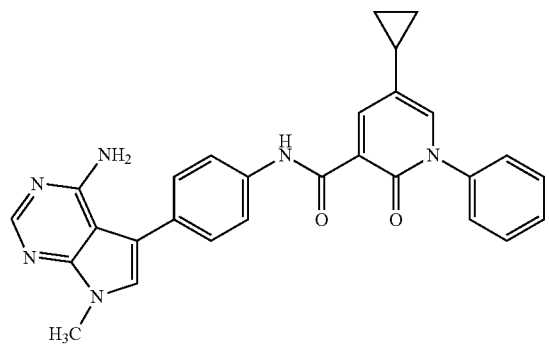 [SMILES: Cn1cc(-c2ccc(NC(=O)c3cc(C4CC4)cn(-c4ccccc4)c3=O)cc2)c2c(N)ncnc21]

The compound (200 mg) produced in Example 91, cyclopropylboronic acid (130 mg), and the compound (25 mg) produced in Example 3 were used and subjected to the procedure having the same object as in Example 27→Example 2→Example 8→Example 6 to obtain the title compound (20 mg) having the following physical property values.
(LC-MS/ELSD): (retention time: 0.81 minutes);
$^1$H-NMR (CDCl$_3$): δ 0.67-0.71, 0.96-1.00, 1.58-1.78, 3.83, 5.08, 6.91, 7.40-7.44, 7.51-7.61, 8.53, 8.54, 8.81, 12.08.

Example 93

2,2-dimethylpropyl 5-bromo-2-oxo-1-phenyl-1,2-dihydropyridine-3-carboxylate 2,2-dimethylpropyl 5-bromo-2-hydroxypyridine-3-carboxylate (2.0 g) was used and subjected to the procedure having the same object as in Example 27 to obtain the title compound (1.5 g) having the following physical property value.
MS (M+H): 350.

Example 94

5-[(2,2-dimethylpropoxy)carbonyl]-6-oxo-1-phenyl-1,6-dihydropyridine-3-carboxylic acid The compound (1.5 g) produced in Example 93 was dissolved in a mixed solution of DMF (10 mL) and tert-butanol (10 mL), subjected to deaeration. After nitrogen substitution thereof, palladium acetate (92 mg), 1,1'-bis (diphenylphosphino) ferrocene (230 mg) and triethylamine (3.0 mL) were added thereto. The resulting mixture was stirred under carbon monoxide atmosphere at room temperature for 16 hours. The reaction solution was filtered through celite, and diluted with dichloromethane. The resulting product was washed with 10% citric acid aqueous solution. The organic layer was dried over sodium sulfate, filtered, and then concentrated under reduced pressure to obtain the title compound (500 mg) having the following physical property values.

$^1$H-NMR (DMSO-d$_6$): δ 0.96, 3.93, 7.46-7.58, 8.38, 8.47, 13.20.

Example 95

N$^3$-[4-(4-amino-7-methyl-7H-pyrrolo[2,3-d]pyrimidin-5-yl)phenyl]-N$^5$-cyclopropyl-2-oxo-1-phenyl-1,2-dihydro-3,5-pyridinedicarboxamide cyclopropyl amine (20 mg), the compound (100 mg) produced in Example 94, and the compound (35 mg) produced in Example 3 were used and subjected to the procedure having the same object as in Example 6→Example 23→Example 6 to obtain the title compound (55 mg) having the following physical property values.

(LC-MS/ELSD): (retention time: 0.71 minutes);
$^1$H-NMR (CDCl$_3$): δ 0.63-0.69, 0.86-0.95, 2.88-2.95, 3.83, 5.09, 6.47, 6.92, 7.40-7.46, 7.54-7.63, 7.79, 8.34, 8.49, 8.88, 11.75.

Examples 95(1) to 95(2)

Amine derivatives corresponding to cyclopropane amine, the compound produced in Example 94, and the compound produced in Example 3 were used and subjected to the procedure having the same object as in Example 95 to obtain the following compounds of Examples.

Example 95(1)

N$^3$-[4-(4-amino-7-methyl-7H-pyrrolo[2,3-d]pyrimidin-5-yl)phenyl]-N$^5$-methyl-2-oxo-1-phenyl-1,2-dihydro-3,5-pyridinedicarboxamide (LC-MS/ELSD): (retention time: 0.67 minutes);
$^1$H-NMR (CDCl$_3$): δ 3.02, 3.83, 5.11, 6.45, 6.92, 7.40-7.46, 7.54-7.63, 7.79, 8.34, 8.50, 8.96, 11.76.

Example 95(2)

N$^3$-[4-(4-amino-7-methyl-7H-pyrrolo[2,3-d]pyrimidin-5-yl)phenyl]-N$^5$,N$^5$-dimethyl-2-oxo-1-phenyl-1,2-dihydro-3,5-pyridinedicarboxamide trifluoroacetate (LC-MS/ELSD): (retention time: 0.69 minutes);
$^1$H-NMR (CD$_3$OD): δ 3.05, 3.81, 7.23, 7.42-7.62, 7.85, 7.97, 8.20, 8.69, 11.95.

Example 96

N-[4-(4-amino-7-methyl-7H-pyrrolo[2,3-d]pyrimidin-5-yl)phenyl]-5-(1-methyl-1H-pyrazol-4-yl)-2-oxo-1-phenyl-1,2-dihydro-3-pyridinecarboxamide The compound (150 mg) produced in Example 93, 1-methyl-4-(4,4,5,5-tetramethyl-1,3,2-dioxaborolan-2-yl)-1H-pyrazole (85 mg), and the compound (22 mg) produced in Example 3 were used and subjected to the procedure having the same object as in Example 2→Example 23→Example 6 to obtain the title compound (31 mg) having the following physical property values.

(LC-MS/ELSD): (retention time: 0.72 minutes);
$^1$H-NMR (CDCl$_3$): δ 3.73, 3.85, 6.06, 7.29, 7.44, 7.53-7.61, 7.81, 7.92, 8.14, 8.24, 8.31, 8.75, 12.12.

Example 97

2,2-dimethylpropyl 5-(3-hydroxy-3-methylbut-1-yn-2-yl)-2-oxo-1-phenyl-1,2-dihydropyridine-3-carboxylate The compound (100 mg) produced in Example 93 was dissolved in acetonitrile (10 mL). To the resulting solution, 2-methyl-3-butyn-2-ol (51 mg), tris(tert-butyl)phosphine (1.0 mL), tetrakis(triphenylphosphine)palladium (0) (32 g), copper iodide (I) (3.0 mg), and triethylamine (0.2 mL) were added. The resulting mixture was stirred at 70° C. for 16 hours. The reaction solution was put to ice water, followed by extraction with ethyl acetate. The organic layer was dried over sodium sulfate, filtered, and then concentrated under reduced pressure. The obtained residue was purified by column chromatography on silica gel (hexane:ethyl acetate=100:0→30:70) to obtain the title compound (55 mg) having the following physical property values.

$^1$H-NMR (CDCl$_3$): δ 1.02, 1.58, 4.01, 7.26-7.38, 7.44-7.49, 7.71, 8.14.

Example 98

N-[4-(4-amino-7-methyl-7H-pyrrolo[2,3-d]pyrimidin-5-yl)phenyl]-5-(3-hydroxy-3-methyl-1-butyn-1-yl)-2-oxo-1-phenyl-1,2-dihydro-3-pyridinecarboxamide The compound (50 mg) produced in Example 97 and the compound (24 mg) produced in Example 3 were used and subjected to the procedure having the same object as in Example 23→Example 6 to obtain the title compound (45 mg) having the following physical property values.

(LC-MS/ELSD): (retention time: 0.77 minutes);
$^1$H-NMR (DMSO-d$_6$): δ 1.46, 3.73, 5.46, 6.05, 7.29, 7.31, 7.55-7.57, 7.77, 8.15, 8.27, 8.42, 11.80.

Example 99 ethyl 2-oxo-1-phenyl-1,2-dihydro-1,7-naphthyridine-3-carboxylate

The compound (557 mg) produced in Example 18 was dissolved in toluene (10 mL). To the resulting solution, 3-bromopyridine-4-carboxaldehyde (500 mg), tris(dibenzylideneacetone)dipalladium (0) (123 mg), 4,5-bis(diphenylphosphino)-9,9-dimethylxanthene (155 mg), and cesium carbonate (1751 mg) were added. The resulting mixture was stirred at 150° C. for one hour. Water was added to the reaction solution, followed by extraction with ethyl acetate. The organic layer was dried over sodium sulfate, filtered, and concentrated under reduced pressure. The obtained residue was purified by chromatography on silica gel (ethyl acetate) to obtain the title compound (245 mg) having the following physical property values.

TLC: Rf 0.23 (hexane:ethyl acetate=1:1);

$^1$H-NMR (CDCl$_3$): δ 1.41, 4.43, 7.29-7.33, 7.52-7.65, 8.13, 8.41, 8.47.

Example 100

N-[4-(4-amino-7-methyl-7H-pyrrolo[2,3-d]pyrimidin-5-yl)phenyl]-2-oxo-1-phenyl-1,2-dihydro-1,7-naphthyridine-3-carboxamide The compound (200 mg) produced in Example 99 and the compound (65 mg) produced in Example 3 were used and subjected to the procedure having the same object as in Example 23→Example 6 to obtain the title compound (100 mg) having the following physical property values.
TLC: Rf 0.75 (dichloromethane:methanol=9:1);
$^1$H-NMR (DMSO-d$_6$): δ 3.78, 6.15, 7.36, 7.50, 7.58-7.76, 7.89, 8.02, 8.14, 8.19, 8.60, 9.18, 11.86.

Example 101 methyl 5-acetyl-6-methyl-2-oxo-1,2-dihydropyridine-3-carboxylate 5-acetyl-6-methyl-2-oxo-1,2-dihydropyridine-3-carboxylic acid (CAS registration No.: 88302-06-1) (100 mg) was dissolved in methanol (20 mL), and oxalyl chloride (0.43 mL) was dropped thereto at 0° C. The resulting mixture was stirred at room temperature for three hours. The reaction solution was concentrated under reduced pressure. A saturated sodium hydrogen carbonate was added to the obtained residue, followed by extraction with dichloromethane. The organic layer was dried over magnesium sulfate, filtered, and then concentrated under reduced pressure to obtain the title compound (400 mg) having the following physical property values.
$^1$H-NMR (CDCl$_3$): δ 2.54, 2.79, 3.94, 8.72, 12.34.

Example 102

5-acetyl-N-[4-(4-amino-7-methyl-7H-pyrrolo[2,3-d]pyrimidin-5-yl)phenyl]-6-methyl-2-oxo-1-phenyl-1,2-dihydro-3-pyridinecarboxamide The compound (500 mg) produced in Example 101 and the compound (38 mg) produced in Example 3 were used and subjected to the procedure having the same object as in Example 27→Example 23→Example 6 to obtain the title compound (6.0 mg) having the following physical property values.
(LC-MS/ELSD): (retention time: 0.76 minutes);
$^1$H-NMR (CDCl$_3$): δ 2.44, 2.68, 3.84, 6.94, 7.21-7.23, 7.42, 7.59-7.67, 7.80, 8.31, 9.14, 11.57.

Example 103 methyl 5-bromo-1-[(1R)-2-hydroxy-1-phenylethyl]-2-oxo-1,2-dihydropyridine-3-carboxylate The compound (1.6 g) produced in Example 53 was dissolved in DMF (6 mL), and N-bromosuccinimide (1.1 g) was added thereto. The resulting mixture was stirred at room temperature for 16 hours. The reaction solution was placed in ice water, and extracted with ethyl acetate. The organic layer was washed with water and a saturated saline solution, dried over sodium sulfate, filtered, and then concentrated under reduced pressure to obtain the title compound (1.2 g) having the following physical property value.
MS (M+H): 353.

Example 104

N-[4-(4-amino-7-methyl-7H-pyrrolo[2,3-d]pyrimidin-5-yl)phenyl]-5-bromo-1-[(1R)-2-hydroxy-1-phenylethyl]-2-oxo-1,2-dihydro-3-pyridinecarboxamide The compound (1.2 g) produced in Example 103 and the compound (60 mg) produced in Example 3 were used and subjected to the procedure having the same object as in Example 23→Example 6 to obtain the title compound (50 mg) having the following physical property values.
(LC-MS/ELSD): (retention time: 0.76 minutes);
$^1$H-NMR (CDCl$_3$): δ 3.84, 4.37, 5.12, 6.41, 6.93, 7.32-7.40, 7.40-7.51, 7.76-7.86, 8.33, 8.67, 11.93.

Example 105

N-[4-(4-amino-7-methyl-7H-pyrrolo[2,3-d]pyrimidin-5-yl)phenyl]-5-cyclopropyl-1-[(1R)-2-hydroxy-1-phenylethyl]-2-oxo-1,2-dihydro-3-pyridinecarboxamide The compound (50 mg) produced in Example 104 and cyclopropylboronic acid (12 mg) were used and subjected to the procedure having the same object as in Example 2 to obtain the title compound (11 mg) having the following physical property values.
(LC-MS/ELSD): (retention time: 0.81 minutes);
$^1$H-NMR (DMSO-d$_6$): δ 0.59-0.64, 0.90-0.97, 1.81-1.90, 3.81, 4.20-4.26, 4.33-4.40, 6.33-6.37, 7.16, 7.32-7.38, 7.39-7.42, 7.47-7.50, 7.78-7.83, 7.83, 8.15, 8.30, 12.16.

Example 106

5-iodo-2-oxo-1-phenyl-1,2-dihydropyridine-3-carboxylic acid 2-oxo-1-phenyl-1,2-dihydropyridine-3-carboxylic acid (CAS registration No.: 868171-81-7) (2.0 g) was dissolved in dichloromethane (10 mL) and trifluoroacetic acid (10 mL), and N-iodosuccinimide (2.9 g) was added thereto. The resulting mixture was stirred at room temperature for two hours. Water was added, and then dichloromethane was added, followed by separating the solution. The organic layer was washed with water and a saturated saline solution, and dried over anhydrous sodium sulfate. The solvent was removed by evaporation under reduced pressure. The obtained residue was dissolved in a small amount of ethyl acetate, and crystallized by addition of hexane. The precipitate was filtered to obtain the title compound (2.1 g) having the following physical property values.
TLC: Rf 0.45 (ethyl acetate, NH silica);
$^1$H-NMR (DMSO-d$_6$): δ 7.49-7.56, 8.48, 14.03.

Example 107 tert-butyl [3-(5-{[4-(4-amino-7-methyl-7H-pyrrolo[2,3-d]pyrimidin-5-yl)phenyl]carbamoyl}-6-oxo-1-phenyl-1,6-dihydropyridine-3-yl)prop-2-yn-1-yl]carbamate The compound (500 mg) produced in Example 106, the compound (390 mg) produced in Example 3, and N-(tert-butoxycarbonyl)propargylamine (CAS registration No.:

92136-39-5) instead of 2-methyl-3-butyn-2-ol were used and subjected to the same procedure as in Example 6→Example 97 to obtain the title compound (160 mg) having the following physical property values.

TLC: Rf 0.35 (hexane:ethyl acetate=2:3);
$^1$H-NMR (DMSO-d$_6$): δ 1.39, 3.72, 3.98, 6.02, 7.29-7.54, 7.76, 7.78, 8.30, 8.41, 11.77.

Example 108

N-[4-(4-amino-7-methyl-7H-pyrrolo[2,3-d]pyrimidin-5-yl)phenyl]-5-(3-aminopropyl)-2-oxo-1-phenyl-1,2-dihydro-3-pyridinecarboxamide The compound (200 mg) produced in Example 107 was used and subjected to the same procedure as in Example 25 to obtain the title compound (83 mg) having the following physical property values.

TLC: Rf 0.15 (ethyl acetate, NH silica);
$^1$H-NMR (CD$_3$OD): δ 1.97, 2.66, 2.97, 3.79, 7.14, 7.43-7.60, 7.74, 7.77, 7.85, 8.14, 8.60.

Example 109

N-[4-(4-amino-7-methyl-7H-pyrrolo[2,3-d]pyrimidin-5-yl)phenyl]-5-[3-(2-butynoylamino)propyl]-2-oxo-1-phenyl-1,2-dihydro-3-pyridinecarboxamide The compound (50 mg) produced in Example 108 was used and subjected to the same procedure as in Example 26 to obtain the title compound (21 mg) having the following physical property values.

TLC: Rf 0.35 (ethyl acetate:methanol=9:1);
$^1$H-NMR (CDCl$_3$): δ 1.91, 1.93, 2.58, 3.35, 3.83, 5.11, 5.83, 6.92, 7.45-7.57, 7.82, 8.34, 8.65, 12.09.

Example 110

5-(4-azide-7-methyl-7H-pyrrolo[2,3-d]pyrimidin-5-yl)pyridine-2-amine

The compound (1.0 g) produced in Example 43 was dissolved in DMF (8 mL). Sodium azide (0.50 g) was added thereto, and the temperature was increased to 80° C. The resulting mixture was stirred for six hours. The reaction solution was diluted with ethyl acetate. Water was added to the reaction solution and the organic layer was extracted. The organic layer was washed with a saturated saline solution, and then dried over anhydrous sodium sulfate. The solvent was removed by evaporation under reduced pressure. Precipitated solid was washed with a hexane-ethyl acetate mixed solvent to obtain the title compound (0.96 g) having the following physical property values.

(LC-MS/ELSD): (retention time: 0.49 minutes);
$^1$H-NMR (DMSO-d$_6$): δ 3.98, 6.03, 6.58, 8.02, 8.20, 8.78, 9.89.

Example 111

N-[5-(4-amino-7-methyl-7H-pyrrolo[2,3-d]pyrimidin-5-yl)-2-pyridinyl]-5-[3-(2-butynoylamino)propyl]-2-oxo-1-phenyl-1,2-dihydro-3-pyridinecarboxamide The compound (770 mg) produced in Example 106 and the compound (500 mg) produced in Example 110 were used and subjected to the procedure having the same object as in Example 6→Example 108→Example 25→Example 26 to obtain the title compound (42 mg) having the following physical property values.

TLC: Rf 0.76 (ethyl acetate:methanol=5:1, NH silica);
$^1$H-NMR (CDCl$_3$): δ 1.89, 1.93, 2.58, 3.37, 3.85, 5.00, 5.80, 6.96, 7.43-7.57, 7.82, 8.36, 8.40, 8.44, 8.62, 12.54.

Example 112 di-tert-butyl [(5-{[5-(4-azide-7-methyl-7H-pyrrolo[2,3-d]pyrimidin-5-yl)pyridine-2-yl]carbamoyl}-3-bromo-6-oxo-1-phenyl-1,6-dihydropyridine-2-yl)methyl]imidodicarbonate The compound (590 mg) produced in Example 23 and the compound (300 mg) produced in Example 110 were used and subjected to the same procedure as in Example 6 to obtain the title compound (720 mg) having the following physical property values. TLC: Rf 0.68 (ethyl acetate, NH silica);

$^1$H-NMR (DMSO-d$_6$): δ 1.39, 4.07, 4.75, 7.39-7.62, 8.37, 8.43, 8.66, 8.78, 9.25, 10.01, 12.15.

Example 113 di-tert-butyl [(5-{[5-(4-amino-7-methyl-7H-pyrrolo[2,3-d]pyrimidin-5-yl)pyridine-2-yl]carbamoyl}-3-bromo-6-oxo-1-phenyl-1,6-dihydropyridine-2-yl)methyl]imidodicarbonate The compound (720 mg) produced in Example 112 was dissolved in water (1 mL) and THF (20 mL). To the resulting mixture, 1 mol/L THF solution of trimethylphosphine (2.8 mL) was added. The resulting mixture was stirred at a bath temperature (60° C.) for two hours. The solvent was removed by evaporation under reduced pressure, followed by purification by column chromatography on silica gel (ethyl acetate:methanol, 90:10, NH silica) to obtain the title compound (590 mg) having the following physical property values.

TLC: Rf 0.33 (ethyl acetate);
$^1$H-NMR (CDCl$_3$): δ 1.42, 3.85, 4.73, 4.99, 6.96, 7.26-7.56, 7.81, 8.37, 8.41, 8.78, 12.20.

Example 114

6-(aminomethyl)-N-[5-(4-amino-7-methyl-7H-pyrrolo[2,3-d]pyrimidin-5-yl)-2-pyridinyl]-2-oxo-1-phenyl-1,2-dihydro-3-pyridinecarboxamide The compound (350 mg) produced in Example 113 was used and subjected to the procedure having the same object as in Example 25 to obtain the title compound (200 mg) having the following physical property values.

TLC: Rf 0.64 (ethyl acetate:methanol=10:1, NH silica);
$^1$H-NMR (DMSO-d$_6$): δ 1.97, 3.31, 3.78, 6.21, 7.02, 7.42-7.67, 7.91, 8.19, 8.38-8.41, 8.68, 12.35.

Example 115

N-[5-(4-amino-7-methyl-7H-pyrrolo[2,3-d]pyrimidin-5-yl)-2-pyridinyl]-6-[(2-butynoyl amino)methyl]-2-oxo-1-phenyl-1,2-dihydro-3-pyridinecarboxamide The compound (50 mg) produced in Example 114 was used and subjected to the same procedure as in Example 26 to obtain the title compound (43 mg) having the following physical property values.

TLC: Rf 0.61 (ethyl acetate:methanol=8:2, NH silica);
$^1$H-NMR (DMSO-d$_6$): δ 2.03, 3.78, 3.88, 6.22, 6.64, 7.43, 7.44-7.50, 7.56-7.75, 7.91, 8.19, 8.35-8.44, 8.66, 9.15, 12.27.

Examples 115(1) to 115(2)

The compound produced in Example 114 and the corresponding carboxylic acid derivative instead of 2-butynoate were used and subjected to the procedure having the same object as in Example 115 to obtain compounds of the following Examples.

Example 115(1)

N-[5-(4-amino-7-methyl-7H-pyrrolo[2,3-d]pyrimidin-5-yl)-2-pyridinyl]-6-{[(cyanoacetyl)amino]methyl}-2-oxo-1-phenyl-1,2-dihydro-3-pyridinecarboxamide TLC: Rf 0.49 (ethyl acetate:methanol=10:1, NH silica);
$^1$H-NMR (DMSO-d$_6$): δ 3.37, 3.78, 3.92, 6.23, 6.75, 7.43, 7.46-7.70, 7.91, 8.19, 8.40, 8.41, 8.64, 8.82, 12.28.

Example 115(2)

N-[5-(4-amino-7-methyl-7H-pyrrolo[2,3-d]pyrimidin-5-yl)-2-pyridinyl]-6-({[(2E)-4-(dimethylamino)-2-butenoy]amino}methyl)-2-oxo-1-phenyl-1,2-dihydro-3-pyridinecarboxamide TLC: Rf 0.36 (ethyl acetate:methanol=10:1, NH silica);
$^1$H-NMR (DMSO-d$_6$): δ 2.18, 2.98, 3.78, 3.95, 6.08-6.19, 6.23, 6.54-6.75, 7.43, 7.46-7.49, 7.58-7.74, 7.91, 8.19, 8.31-8.48, 8.54-8.72, 12.29.

Example 116

6-(aminomethyl)-N-[5-(4-amino-7-methyl-7H-pyrrolo[2,3-d]pyrimidin-5-yl)-2-pyridinyl]-5-bromo-2-oxo-1-phenyl-1,2-dihydro-3-pyridinecarboxamide The compound (60 mg) produced in Example 112 was used and subjected to the procedure having the same object as in Example 8 to obtain the title compound (41 mg) having the following physical property values.
TLC: Rf 0.68 (ethyl acetate:methanol=10:1, NH silica);
$^1$H-NMR (DMSO-d$_6$): δ 1.75, 3.50, 3.78, 6.23, 7.43, 7.53-7.68, 7.93, 8.19, 8.37, 8.42, 8.66, 12.18.

Example 117

N-[5-(4-amino-7-methyl-7H-pyrrolo[2,3-d]pyrimidin-5-yl)-2-pyridinyl]-5-bromo-6-[(2-butynoylamino)methyl]-2-oxo-1-phenyl-1,2-dihydro-3-pyridine carboxamide The compound (25 mg) produced in Example 116 was used and subjected to the procedure having the same object as in Example 26 to obtain the title compound (20 mg) having the following physical property values.
TLC: Rf 0.66 (ethyl acetate:methanol=8:2, NH silica);
$^1$H-NMR (DMSO-d$_6$): δ 2.00, 3.78, 4.05, 6.24, 7.44, 7.47-7.63, 7.94, 8.20, 8.37, 8.43, 8.68, 8.81, 12.16.

Example 118

7-benzyl-5,6,7,8-tetrahydro-1,7-naphthyridine-2(1H)-one

To 1,7-naphthyridine-2(1H)-one (CAS registration No.: 54920-82-0) (900 mg), ethanol (20 mL) and benzyl bromide (0.8 mL) were added. The resulting mixture was heated and stirred at 80° C. for 18 hours. The resulting mixture was cooled to 0° C., and then sodium borohydride (1100 mg) was added thereto. The resulting product was stirred at 0° C. for 10 minutes, and then hydrochloric acid was added thereto. The resulting mixture was stirred at room temperature for 90 minutes. The resulting product mixture was neutralized with sodium hydroxide, and then ethyl acetate was added to extract the organic layer. The organic layer was extracted. The organic layer was washed with a saturated saline solution, and then dried over anhydrous sodium sulfate, and the solvent was removed by evaporation under reduced pressure. Thereafter, the resulting solid was washed with ethyl acetate to obtain the title compound (900 mg) having the following physical property values.
$^1$H-NMR (CD$_3$OD): δ 2.66, 2.80, 3.45, 3.75, 6.40, 7.29-7.44.

Example 119

5,6,7,8-tetrahydro-1,7-naphthyridine-2(1H)-one trifluoroacetate

The compound (800 mg) produced in Example 118 was dissolved in methanol (10 mL), and trifluoroacetic acid (0.270 mL) and palladium carbon (160 mg) were added thereto. The resulting solution was stirred under the atmosphere of hydrogen gas at room temperature for five hours. The reaction solution was filtered through celite and the solvent was removed by evaporation under reduced pressure to obtain the title compound (800 mg) having the following physical property values.
$^1$H-NMR (CD$_3$OD): δ 2.89, 3.51, 4.21, 6.53, 7.48.

Example 120 tert-butyl 2-oxo-2,5,6,8-tetrahydro-1,7-naphthyridine-7(1H)-carboxylate

The compound (800 mg) produced in Example 119 was dissolved in THF (10 mL), and triethylamine (1.3 mL) and di-tert-butyl dicarbonate (0.850 mL) were added thereto. The resulting mixture was stirred at room temperature for three hours. Water was added to the reaction solution, followed by extraction with ethyl acetate. The organic layer was washed with a saturated saline solution, dried over anhydrous sodium sulfate, and the solvent was removed by evaporation under reduced pressure. Thereafter, the resulting solid was washed with an MTBE solvent to obtain the title compound (760 mg) having the following physical property values.
(LC-MS/ELSD): (retention time: 0.70 minutes);
$^1$H-NMR (CD$_3$OD): δ 1.52, 2.61, 3.66, 4.43, 6.42, 7.43.

Example 121 tert-butyl 3-bromo-2-oxo-2,5,6,8-tetrahydro-1,7-naphthyridine-7(1H)-carboxylate

The compound (490 mg) produced in Example 120 was dissolved in THF (5 mL), and N-bromosuccinimide (360 mg) was added thereto. The resulting mixture was stirred at room temperature for two hours. The reaction solution was diluted with ethyl acetate, water was added, and the organic layer was extracted. The organic layer was washed with a saturated saline solution, dried over anhydrous sodium sulfate, and a solvent was removed by evaporation under reduced pressure to obtain the title compound (560 mg) having the following physical property values.

TLC: Rf 0.17 (ethyl acetate:methanol=10:1);

$^1$H-NMR (CD$_3$OD): δ 1.52, 2.61, 3.65, 4.39, 7.83.

Example 122

7-tert-butyl 3-methyl 2-oxo-1-phenyl-2,5,6,8-tetrahydro-1,7-naphthyridine-3,7(1H)-dicarboxylate The compound (1400 mg) produced in Example 121 was used and subjected to the procedure having the same object as in Example 27→Example 28 to obtain the title compound (96 mg) having the following physical property values.

(LC-MS/ELSD): (retention time: 1.01 minutes);

TLC: Rf 0.54 (hexane:ethyl acetate=1:1);

Example 123

N-[4-(4-Amino-7-methyl-7H-pyrrolo[2,3-d]pyrimidin-5-yl)phenyl]-7-(2-butynoyl)-2-oxo-1-phenyl-1,2,5,6,7,8-hexahydro-1,7-naphthyridine-3-carboxamide

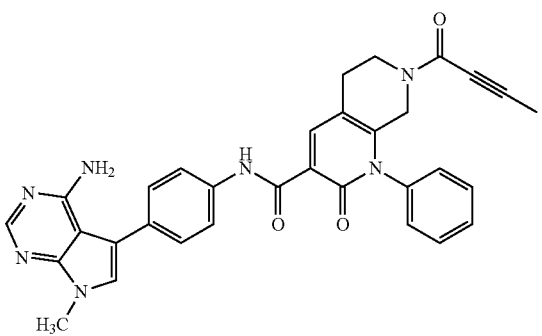 [SMILES: CC#CC(=O)N1CCc2cc(C(=O)Nc3ccc(-c4cn(C)c5ncnc(N)c45)cc3)c(=O)n(-c3ccccc3)c2C1]

The compound (80 mg) produced in Example 122 and the compound (20 mg) produced in Example 3 were used and subjected to the procedure having the same object as in Example 23→Example 6→Example 8→Example 26 to obtain the title compound (5 mg) having the following physical property values.

TLC: Rf 0.40 (ethyl acetate:methanol=10:1);

$^1$H-NMR (CDCl$_3$): (observed as a rotamer mixture), δ 1.89 (2.05), 2.82 (2.88), 3.83, 3.85 (3.99), 4.22 (4.35), 5.11, 6.91, 7.22-7.34, 7.42, 7.59-7.80, 8.33, 8.56, 11.84.

Example 124

6-(tert-butoxycarbonyl)-2,5-dioxo-1-phenyl-1,2,5,6,7,8-hexahydro-1,6-naphthyridine-3-carboxylic acid Ethyl (2E)-2-cyano-3-ethoxyprop-2-enoate (2400 mg) and tert-butyl 2,4-dioxopiperidine-1-carboxylate (CAS registration No.: 845267-78-9) (3000 mg) were used and subjected to the procedure having the same object as in Example 4→Example 5 to obtain the title compound (84 mg) having the following physical property values.

MS (M+H): 385.

$^1$H-NMR (DMSO-d$_6$): δ 1.46, 2.62, 3.82, 7.43, 7.56-7.62, 8.74, 13.33.

Example 125

N-{4-[4-amino-7-(2-hydroxy-2-methylpropyl)-7H-pyrrolo[2,3-d]pyrimidin-5-yl]phenyl}-2,5-dioxo-1-phenyl-1,2,5,6,7,8-hexahydro-1,6-naphthyridine-3-carboxamide A compound (30 mg) obtained by subjecting the compound produced in Example 11 to the procedure having the same object as in Example 2→Example 3 and compound (43 mg) produced in Example 124 were used and subjected to the procedure having the same object as in Example 6→Example 8 to obtain the title compound (12 mg) having the following physical property values.

(LC-MS/ELSD): (retention time: 0.61 minutes);

$^1$H-NMR (DMSO-d$_6$): δ 1.14, 2.44-2.68, 4.22, 7.48-7.70, 7.89, 8.01, 8.47, 8.99, 11.77.

Example 126

2-methyl-2-propanyl 3-{[5-(4-amino-7-methyl-7H-pyrrolo[2,3-d]pyrimidin-5-yl)-2-pyridinyl]carbamoyl}-2,5-dioxo-1-phenyl-1,5,7,8-tetrahydro-1,6-naphthyridine-6(2H)-carboxylate The compound (95 mg) produced in Example 124 and the compound (60 mg) produced in Example 43 were used and subjected to the procedure having the same object as in Example 6→Example 3 to obtain the title compound (68 mg) having the following physical property values.

(LC-MS/ELSD): (retention time: 0.76 minutes);

MS (M+H): 607.

Example 126(1)

2-methyl-2-propanyl 3-({5-[4-amino-7-(2-hydroxy-2-methylpropyl)-7H-pyrrolo[2,3-d]pyrimidin-5-yl]-2-pyridinyl}carbamoyl)-2,5-dioxo-1-phenyl-1,5,7,8-tetrahydro-1,6-naphthyridine-6(2H)-carboxylate The compound (78 mg) produced in Example 124 and the corresponding pyrrolopyrimidine derivative (60 mg) instead of the compound produced in Example 43 were used and subjected to the procedure having the same object as in Example 126 to obtain the title compound (69 mg) having the following physical property values.

(LC-MS/ELSD): (retention time: 0.75 minutes);
MS (M+H): 665.

Example 127

N-[5-(4-amino-7-methyl-7H-pyrrolo[2,3-d]pyrimidin-5-yl)-2-pyridinyl]-2,5-dioxo-1-phenyl-1,2,5,6,7,8-hexahydro-1,6-naphthyridine-3-carboxamide The compound (52 mg) produced in Example 126 was used and subjected to the procedure having the same object as in Example 8 to obtain the title compound (26 mg) having the following physical property values.

(LC-MS/ELSD): (retention time: 0.57 minutes);
$^1$H-NMR (DMSO-$d_6$): δ 2.49-2.60, 3.73, 6.19, 7.38, 7.44-7.50, 7.52-7.66, 7.86-7.90, 7.96, 8.15, 8.34-8.37, 8.96, 12.01.

Example 127(1)

N-{5-[4-amino-7-(2-hydroxy-2-methylpropyl)-7H-pyrrolo[2,3-d]pyrimidin-5-yl]-2-pyridinyl}-2,5-dioxo-1-phenyl-1,2,5,6,7,8-hexahydro-1,6-naphthyridine-3-carboxamide The compound (63 mg) produced in Example 126(1) was used and subjected to the procedure having the same object as in Example 127 to obtain the title compound (46 mg) having the following physical property values.

(LC-MS/ELSD): (retention time: 0.56 minutes);
$^1$H-NMR (DMSO-$d_6$): δ 1.06, 2.51, 3.28-3.36, 4.10, 4.83, 6.19, 7.35, 7.46-7.49, 7.54-7.66, 7.88-7.92, 7.96, 8.13, 8.36, 8.37-8.39, 8.97, 12.02.

Example 128

5-(4-aminophenyl)6-trifluoromethyl-7-methyl-7H-pyrrolo[2,3-d]pyrimidine-4-amine

The compound (480 mg) produced in Example 3 was dissolved in methylene chloride (8 mL) and water (3 mL), and sodium trifluoromethanesulfinate (930 mg) and tert-butyl hydroperoxide (2 mL) were added thereto. The resulting mixture was stirred at room temperature for 24 hours. The reaction solution was diluted with ethyl acetate, and water was added thereto, and the organic layer was extracted. The organic layer was washed with a saturated saline solution, dried over anhydrous sodium sulfate, and the solvent was removed by evaporation under reduced pressure. Thereafter, the resulting product was purified by column chromatography on silica gel (ethyl acetate:methanol=10:1) to obtain the title compound (38 mg) having the following physical property values.

TLC: Rf 0.57 (ethyl acetate:methanol=10:1);
$^1$H-NMR (CDCl$_3$): δ 3.91, 5.16, 6.76, 7.17, 8.34.

Example 129

N-{4-[4-amino-7-methyl-6-(trifluoromethyl)-7H-pyrrolo[2,3-d]pyrimidin-5-yl]phenyl}-2,5-dioxo-1-phenyl-1,2,5,6,7,8-hexahydro-3-quinolinecarboxamide

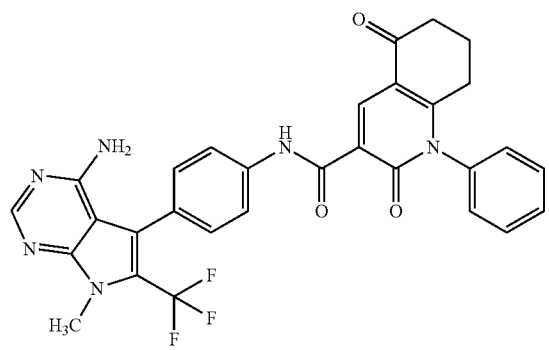 [SMILES: Cn1c(C(F)(F)F)c(-c2ccc(NC(=O)c3cc4c(n(-c5ccccc5)c3=O)CCCC4=O)cc2)c2c(N)ncnc21]

The compound (8 mg) produced in Example 128 and the compound (8 mg) produced in Example 5 were used and subjected to the procedure having the same object as in Example 6 to obtain the title compound (10 mg) having the following physical property values.

TLC: Rf 0.59 (ethyl acetate:methanol=10:1);
$^1$H-NMR (CDCl$_3$): δ 2.09-2.13, 2.55-2.64, 3.92, 4.92, 7.26-7.29, 7.35, 7.61-7.69, 7.80, 8.37, 9.33, 11.50.

Example 130

N-[4-(4-amino-7-methyl-7H-pyrrolo[2,3-d]pyrimidin-5-yl)phenyl]-2,5-dioxo-1-phenyl-2,5,6,7-tetrahydro-1H-cyclopenta[b]pyridine-3-carboxamide Methyl 2,5-dioxo-2,5,6,7-tetrahydro-1H-cyclopenta[b]pyridine-3-carboxylate (400 mg), phenylboric acid (470 mg), and the compound (68 mg) produced in Example 3 were used and subjected to the procedure having the same object as in Example 27 Example 23→Example 6 to obtain the title compound (95 mg) having the following physical property values.

TLC: Rf 0.44 (dichloromethane:methanol=9:1);
$^1$H-NMR (DMSO-$d_6$): δ 2.56-2.63, 2.69-2.77, 3.72, 6.06, 7.29, 7.42, 7.55, 7.59-7.69, 7.80, 8.13, 8.58, 11.47.

Examples 130(1) to 130(2)

Methyl 2,5-dioxo-2,5,6,7-tetrahydro-1H-cyclopenta[b]pyridine-3-carboxylate, phenylboric acid, and the corresponding pyrrolopyrimidine derivative instead of the compound produced in Example 3 were used and subjected to the procedure having the same object as in Example 130 to obtain the following compounds of Examples.

Example 130(1)

N-{4-[4-amino-7-(2-hydroxy-2-methylpropyl)-7H-pyrrolo[2,3-d]pyrimidin-5-yl]phenyl}-2,5-dioxo-1-phenyl-2,5,6,7-tetrahydro-1H-cyclopenta[b]pyridine-3-carboxamide (LC-MS/ELSD): (retention time: 0.64 minutes);
$^1$H-NMR (DMSO-$d_6$): δ 1.11, 2.59-2.67, 2.72-2.84, 4.14, 4.88, 6.13, 7.32, 7.49, 7.58-7.73, 7.85, 8.17, 8.64, 11.53.

Example 130(2)

N-[5-(4-amino-7-methyl-7H-pyrrolo[2,3-d]pyrimidin-5-yl)-2-pyridinyl]-2,5-dioxo-1-phenyl-2,5,6,7-tetrahydro-1H-cyclopenta[b]pyridine-3-carboxamide (LC-MS/ELSD): (retention time: 0.61 minutes);
$^{1}$H-NMR (DMSO-$d_6$): δ 2.54-2.65, 2.68-2.79, 3.74, 6.21, 7.40, 7.51-7.72, 7.84-7.95, 8.16, 8.35, 8.38-8.41, 8.64, 11.87.

Example 131

N-{4-[4-amino-7-(3-hydroxycyclopentyl)-7H-pyrrolo[2,3-d]pyrimidin-5-yl]phenyl}-2-oxo-1-phenyl-1,2-dihydro-3-pyridinecarboxamide The compound (530 mg) produced in Example 13, 4-(4,4,5,5-tetramethyl-1,3,2-dioxaborolan-2-yl)aniline (410 mg), and the corresponding carboxylic acid derivative (72 mg) instead of the compound produced in Example 5 were used and subjected to the procedure having the same object as in Example 53→Example 2→Example 6→Example 55→Example 3 to obtain the title compound (35 mg) having the following physical property values.

(LC-MS/ELSD): (retention time: 4.00 minutes);
$^{1}$H-NMR (DMSO-$d_6$): δ 1.74-1.85, 1.99-2.17, 2.30-2.45, 4.22-4.26, 5.00, 5.12-5.20, 6.06, 6.72, 7.44, 7.47, 7.52-7.60, 7.79, 8.11, 8.12, 8.60, 12.03.

Example 132

N-[4-(4-amino-7H-pyrrolo[2,3-d]pyrimidin-5-yl)phenyl]-2-oxo-1-[(1 S)-1-phenylethyl]-1,2-dihydro-3-pyridinecarboxamide 5-(4-aminophenyl)-7-((2-(trimethylsilyl)ethoxy)methyl)-7H-pyrrolo[2,3-d]pyrimidine-4-amine (100 mg) and the corresponding carboxylic acid derivative (68 mg) instead of the compound produced in Example 5 were used and subjected to the procedure having the same object as in Example 6→Example 17 to obtain the title compound (71 mg) having the following physical property values.

TLC: Rf 0.66 (ethyl acetate:methanol=5:1);
$^{1}$H-NMR (DMSO-$d_6$): δ 1.78, 6.19, 6.36, 6.66, 7.26, 7.29-7.42, 7.45, 7.79, 8.12, 8.47, 11.89, 12.19.

Example 132(1)

N-[4-(4-amino-7H-pyrrolo[2,3-d]pyrimidin-5-yl)phenyl]-4,6-dimethyl-2-oxo-1-phenyl-1,2-dihydro-3-pyridinecarboxamide 5-(4-aminophenyl)-7-((2-(trimethylsilyl)ethoxy)methyl)-7H-pyrrolo[2,3-d]pyrimidine-4-amine (100 mg) and the corresponding carboxylic acid derivative (68 mg) instead of the compound produced in Example 5 were used and subjected to the procedure having the same object as in Example 132 to obtain the title compound (44 mg) having the following physical property values.

TLC: Rf 0.56 (ethyl acetate:methanol=5:1);
$^{1}$H-NMR (DMSO-$d_6$): δ 1.94, 2.37, 5.99, 6.36, 7.18, 7.29, 7.39, 7.46-7.59, 7.74, 8.08, 11.02, 11.74.

Experiment Example

Biological Experiment Examples are described below. Based on these experiment methods, the advantageous effect of the compound of the present invention was verified.

Biological Experiment Example 1

Measurement of Axl Inhibitory Activity (In Vitro Test)

The Axl enzyme inhibitory activity was measured by using LanthaScreen (registered trademark) system (Invitrogen) based on the attached instruction. The reagents used are shown below.

Reaction buffer solution: A solution containing 50 mmol/L HEPES (pH7.5), 0.01% Brij35, 10 mmol/L $MgCl_2$ and 1 mmol/L EGTA was prepared by using purified water.

Test substance solution: A solution containing a test compound of 5-fold concentration with respect to the final concentration was prepared by 20-fold diluting a DMSO solution of the test compound of each concentration with the reaction buffer solution.

Enzyme solution: A solution containing 400 ng/mL Axl enzyme was prepared by using the reaction buffer solution.

Substrate solution: A solution containing 45 μmmol/L ATP and 500 nmmol/L Fluorescein-Poly GT (Invitrogen) was prepared by using the reaction buffer solution.

Detection solution: A solution containing 20 mM EDTA and 4 nM PY20 (Invitrogen) was prepared by using Dilution B (Invitrogen).

A 10 mmol/L DMSO solution of the test compound was dispensed into a 96-well plate (Nunc), and, furthermore, a 3-fold dilution series was prepared using DMSO. In each well of the 96-well plate for measurement, 5 μL each of the reaction buffer solution containing DMSO was added to a Blank group and a medium group, and 5 μL of the test substance solution was added to the test substance group, respectively. Next, 10 μL/well of the reaction buffer solution was added to the Blank group, and 10 μL/well each of the enzyme solution was added to the medium group and the test compound group, followed by stirring at room temperature for 10 minutes. After the completion of stirring, 10 μL each of the substrate solution was added into each well, followed by stirring at room temperature with light shielded for one hour. After the completion of reaction, 25 μL each of the detection solution was added to each well, and stood still at room temperature with light shielded for 30 minutes. After standing still, fluorescence intensity at 520 nm and 495 nm at the time of irradiation with exciting light of 340 nm was measured by using Analyst GT (Molecular Devices). The phosphorylation of the artificial substrate was quantified by Time-resolved Fluorescence Resonance Energy Transfer (TR-FRET). The TR-FRET ratio was calculated by dividing 520 nm fluorescence signal by 495 nm fluorescence signal for each well, and the inhibition rate (%) in the test compound group was calculated based on the following mathematical formula.

$$\text{Inhibition rate (\%)} = \{1 - (\text{TR-FRET ratio of test compound group} - A)/(B - A)\} \times 100 \quad [\text{Math. 1}]$$

A: Average value of TR-FRET ratios of Blank group
B: Average value of TR-FRET ratios of medium group Values of 50% inhibition rate (IC50 values) of the test compound were calculated from the inhibition curve based on the inhibition rate of the test compounds in each concentration.

As a result, in the compounds of the present invention, IC50 values of the compound of, for example, Examples 45(24), 26, and 30 were 0.0097 µM, 0.0017 µM, and 0.0080 µM, respectively.

Biological Example 2

Measurement of Proliferation Suppression Rate by Using Mouse Pro-B Cell Line (Ba/F3 Axl) Stably Expressing Axl A 0.1 mmol/L DMSO solution of the test compound was dispensed into a 96-well plate, and further a 3-fold dilution series was prepared using DMSO. DMSO solutions of test compounds, having various concentrations, were further 500-fold diluted with a RPMI1640 medium (containing 10% HI-FBS and 1% penicillin) and a diluted solution of the test compound having 500-fold concentration with respect to the final concentration was prepared. In each well of the 96-well plate (BD Biosciences) for measurement, 50 µL of a RPMI medium was added to the Blank group, 50 µL of a RPMI medium containing 0.2% DMSO was added to the medium group, and 50 µL of the diluted solution of the test compound was added to the test compound group, respectively. Ba/F3 Axl was diluted with a medium to have a density of $2 \times 10^5$ cells/mL to prepare a cell suspension. In each well of the 96-well plate for measurement, 50 µL each of the RPMI medium was added to the Blank group, and 50 µL each of the cell suspension was added to the medium group and the test compound group, respectively, and the groups were stood still at 37° C. at 5% $CO_2$ for 48 hours. After standing still, Relative Light Unit (RLU) was measured by using CELLTITER-GLO (registered trademark) LUMINESCENT CELL VIABILITY ASSAY (Promega). The measurement was carried out according to the attached instruction. To each well, 100 µL each of light-emitting solution was added. The plate was stirred at room temperature for 3 min and then stood still at room temperature with light shielded for 10 minutes, and RLU was measured by using Microplate Reader (SpectraMax M5e, Molecular Devices). The average values of RLU of the Blank group and the medium group were respectively calculated, and the proliferation suppression rate of the test compound group was calculated.

Proliferation suppression rate (%)={1−(RLU of test compound group−A)/(B−A)}×100    [Math. 2]

A: Average value of RLU of Blank group
B: Average value of RLU of medium group

A value of 50% inhibition rate (IC50 value) of the test compound was calculated from the inhibition curve based on the inhibition rate in each concentration of the test compound.

As a result, in the compounds of the present invention, IC50 values of the compounds of, for example, Examples 45(24), 26, and 30 were 0.0070 µM, 0.0008 µM, and 0.0106 µM, respectively.

FORMULATION EXAMPLE

Formulation Example 1

The components indicated below were mixed by a standard method, followed by making the mixture into tablets to obtain 10,000 tablets each containing 10 mg of active ingredient.

| | |
|---|---:|
| N-[4-(4-amino-7-methyl-7H-pyrrolo[2,3-d]pyrimidine-5-yl)phenyl]-6-[(2-butynoylamino)mehyl]-2-oxo-1-phenyl-1,2-dihydro-3-pyridinecarboxamide | 100 g |
| calcium carboxymethyl cellulose (disintegrant) | 20 g |
| magnesium stearate (lubricant) | 10 g |
| microcrystalline cellulose | 870 g |

Formulation Example 2

The components indicated below were mixed by routine procedures, and then filtered through a dedusting filter and a dust-removing filter. Then, 5 ml each of the obtained product was filled in an ampoule and sterilized by heat in an autoclave, to obtain 10,000 ampoules. One ampoule contains 20 mg of active ingredients.

| | |
|---|---:|
| N-[4-(4-amino-7-methyl-7H-pyrrolo[2,3-d]pyrimidin-5-yl)phenyl]-2-oxo-1-phenyl-5-(trifluoromethyl)-1,2-dihydro-3-pyridinecarboxamide trifluoroacetate | 200 g |
| mannitol | 20 g |
| distilled water | 50 L |

INDUSTRIAL APPLICABILITY

A compound of the present invention has strong Axl inhibitory activity, and therefor is useful for treating Axl-related diseases, for example, cancers, kidney diseases, immune-system diseases, and circulatory system diseases.

The invention claimed is:
1. A compound represented by the general formula (1):

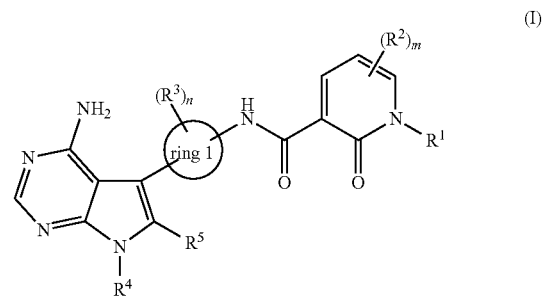

wherein $R^1$ represents (1) a C1-8 alkyl group optionally substituted with one to five $R^{11}$, (2) a C3-7 carbon ring optionally substituted with one to five $R^{12}$, or (3) a 4- to 7-membered heterocycle optionally substituted with one to five $R^{13}$, wherein when the C1-8 alkyl group represented by $R^1$ is a branched alkyl group, the C1-3 alkyl groups branched from the same carbon atom together optionally form a saturated C3-7 carbon ring, $R^2$ represents (1) a C1-8 alkyl group optionally substituted with one to five $R^{21}$, (2) a C2-8 alkenyl group optionally substituted with one to five $R^{22}$, (3) a C2-8 alkynyl group optionally substituted with one to five $R^{23}$, (4) an —$OR^{24}$ group, (5) a C3-7 carbocyclic ring optionally substituted with one to five $R^{25}$, (6) 4- to 7-membered heterocycle optionally substituted with one to five $R^{26}$, (7) a halogen atom, (8) a $C(O)R^{27}$ group, or (9) a $C(O)NR^{28}R^{29}$ group, wherein, when m is 2 or more, $R^2$s are on neighboring carbon atoms, and each $R^2$ represents a C1-3 alkyl group optionally substituted with an amino group or a C2-3 alkenyl group optionally substituted with an amino group, when $R^2$s bonded to the neighboring carbon atoms together with the carbon atoms may form a 5- to 7-membered cyclic group optionally substituted with one to three $R^{20}$, $R^3$ represents (1) a C1-4 alkyl group, (2) a halogen atom, (3) a C1-4 haloalkyl group, or (4) an —$OR^{31}$ group, $R^4$ represents (1) a hydrogen atom, (2) a C1-8 alkyl group optionally substituted with one to five $R^{41}$, (3) a C3-10 carbocyclic ring optionally substituted with one to five $R^{42}$, or (4) a 4- to 10-membered heterocycle optionally substituted with one to five $R^{43}$, $R^5$ represents (1) a hydrogen atom, (2) a C1-4 alkyl group, (3) a halogen atom, or (4) a C1-4 haloalkyl group, $R^{11}$ represents (1) an —$OR^{101}$ group, (2) an $SO_2R^{102}$ group, (3) an $NR^{103}R^{104}$ group, or (4) a C3-7 carbon ring optionally substituted with one to three halogen atoms, $R^{12}$ represents (1) a C1-4 alkyl group optionally substituted with an amino group, or (2) a C1-4 haloalkyl group, and (3) a halogen atom, $R^{13}$ represents (1) a C1-4 alkyl group optionally substituted with an amino group, or (2) a C1-4 haloalkyl group, and (3) a halogen atom, $R^{101}$ represents (1) a hydrogen atom, or (2) a C1-4 alkyl group, $R^{102}$ represents (1) a hydrogen atom, or (2) a C1-4 alkyl group, $R^{103}$ and $R^{104}$ each independently represent (1) a hydrogen atom, or (2) a C1-4 alkyl group, $R^{20}$ represents (1) a C1-4 alkyl group, (2) a halogen atom, (3) a C1-4 haloalkyl group, (4) an oxo group, (5) an —$OR^{201}$ group, or (6) a $COOR^{205}$ group, wherein when two $R^{20}$s represent a C1-3 alkyl group and are on the same carbon atom, the $R^{20}$s together may form a C3-7 saturated carbon ring, $R^{21}$, $R^{22}$, and $R^{23}$ each independently represent (1) a hydrogen atom, (2) —$OR^{202}$, or (3) $NR^{203}R^{204}$, $R^{24}$ represents (1) a hydrogen atom, (2) a C1-4 alkyl group, or (3) 4- to 10-membered heterocycle, $R^{25}$ and $R^{26}$ each independently represent (1) a C1-4 alkyl group, or (2) a halogen atom, $R^{27}$ represents (1) a hydrogen atom, (2) a C1-4 alkyl group, or (3) a C3-7 carbocyclic ring, $R^{28}$ and $R^{29}$ each independently represent (1) a hydrogen atom, (2) a C1-4 alkyl group, or (3) a C3-7 carbocyclic ring, $R^{201}$ represents (1) a hydrogen atom, or (2) a C1-4 alkyl group, $R^{202}$ represents (1) a hydrogen atom, or (2) a C1-4 alkyl group, $R^{203}$ and $R^{204}$ each independently represents (1) a hydrogen atom, (2) a C1-4 alkyl group, or (3) a $C(O)R^{210}$ group, $R^{205}$ represents (1) a hydrogen atom, or (2) a C1-4 alkyl group, $R^{210}$ represents (1) a C1-4 alkyl group optionally substituted with $NR^{211}R^{212}$ or a cyano group, (2) a C2-4 alkenyl group optionally substituted with $NR^{213}R^{214}$ or a cyano group, or (3) a C2-4 alkynyl group optionally substituted with $NR^{215}R^{216}$ or a cyano group, $R^{211}$, $R^{212}$, $R^{213}$, $R^{214}$, $R^{215}$, and $R^{216}$ each independently represent (1) a hydrogen atom, or (2) a C1-4 alkyl group, $R^{31}$ represents (1) a hydrogen atom, (2) a C1-4 alkyl group, or (3) a C1-4 haloalkyl group, $R^{41}$ represents (1) an —$OR^{401}$ group, (2) an $SO_2R^{402}$ group, (3) an $NR^{403}R^{404}$ group, or (4) 5- to 7-membered cyclic group optionally substituted with one to three $R^{405}$, $R^{42}$ represents (1) a C1-4 alkyl group optionally substituted with a hydroxyl group or an $NR^{406}R^{407}$ group, (2) a halogen atom, (3) a hydroxyl group, or (4) an oxo group, $R^{43}$ represents (1) a C1-4 alkyl group optionally substituted with a hydroxyl group or an $NR^{408}R^{409}$ group, (2) a halogen atom, (3) a hydroxyl group, or (4) an oxo group, $R^{401}$ represents (1) a hydrogen atom, or (2) a C1-4 alkyl group, $R^{402}$ represents (1) a hydrogen atom, or (2) a C1-4 alkyl group, $R^{403}$ and $R^{404}$ each independently represent (1) a hydrogen atom, or (2) a C1-4 alkyl group, $R^{405}$ represents (1) a halogen atom, (2) a hydroxyl group, (3) an amino group, or (4) a C1-4 alkyl group, $R^{406}$, $R^{407}$, $R^{408}$, and $R^{409}$ each independently represent (1) a hydrogen atom, or (2) a C1-4 alkyl group, ring1 represents a 5- to 7-membered cyclic group, when a plurality of $R^{11}$, $R^{12}$, $R^{13}$, $R^{20}$, $R^{21}$, $R^{22}$, $R^{23}$, $R^{25}$, $R^{26}$, $R^{41}$, $R^{42}$, $R^{43}$, or $R^{405}$ is present, any of them may be the same as or different from each other, m is an integer from 0 to 3, n is an integer from 0 to 3, when m is 2 or more, a plurality of $R^2$s may be the same as or different from each other, when n is 2 or more, a plurality of $R^3$s may be the same as or different from each other, a salt thereof or an N-oxide thereof.

2. The compound according to claim 1, wherein the ring1 is benzene or pyridine, a salt thereof, or an N-oxide thereof.

3. The compound according to claim 1, which is represented by the general formula (I-1):

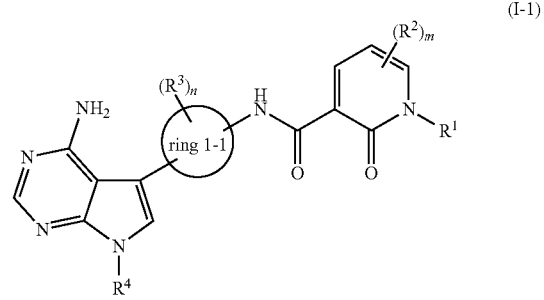

wherein ring 1-1 represents benzene or pyridine, and the other reference marks mean the same as those in claim 1, a salt thereof, or an N-oxide thereof.

4. The compound according to claim 1, which is: (1) N-[5-(4-amino-7-methyl-7H-pyrrolo[2,3-d]pyrimidin-5-yl)-2-pyridinyl]-2',5'-dioxo-1'-phenyl-2',5',6',8'-tetrahydro-1'H-spiro[cyclopropane-1,7'-quinoline]-3'-carboxamide, (2)N-[4-(4-amino-7-methyl-7H-pyrrolo[2,3-d]pyrimidin-5-yl)phenyl]-2-oxo-1-phenyl-5-(trifluoromethyl)-1,2-dihydro-3-pyridinecarboxamide, (3)N-[4-(4-amino-7-methyl-7H-pyrrolo[2,3-d]pyrimidin-5-yl)phenyl]-6-[(2-butynoylamino)methyl]-2-oxo-1-phenyl-1,2-dihydro-3-pyridinecarboxamide, (4) N-[4-(4-amino-7-methyl-7H-pyrrolo[2,3-d]pyrimidin-5-yl)phenyl]-2,5-dioxo-1-phenyl-1,2,5,6,7,8-hexahydro-3-quinolinecarboxamide, (5)N-[4-(4- amino-7-cyclopentyl-7H-pyrrolo[2,3-d]pyrimidin-5-yl)phenyl]-2-oxo-1-phenyl-1,2-dihydro-3-pyridinecarboxamide, (6) N-{4-[4-amino-7-(2-hydroxy-2-methylpropyl)-7H-pyrrolo[2,3-d]pyrimidin-5-yl]phenyl}-2,5-dioxo-1-phenyl-1,2,5,6,7,8-hexahydro-3-quinolinecarboxamide, (7)N-[4-(4-amino-7-methyl-7H-pyrrolo[2,3-d]pyrimidin-5-yl)phenyl]-2-oxo-1-phenyl-1,2-dihydro-3-quinolinecarboxamide, (8)N-[4-{4-amino-7-[cis-3-(hydroxymethyl)cyclobutyl]-7H-pyrrolo[2,3-d]pyrimidin-5-yl}phenyl)-2,5-dioxo-1-phenyl-1,2,5,6,7,8-hexahydro-3-quinolinecarboxamide, (9)N-[5-(4-amino-7-methyl-7H-pyrrolo[2,3-d]pyrimidin-5-yl)-2-pyridinyl]-2,5-dioxo-1-phenyl-1,2,5,6,7,8-hexahydro-3-quinolinecarboxamide, (10)N-[4-(4-amino-7-methyl-7H-pyrrolo[2,3-d]pyrimidin-5-yl)phenyl]-1-[(1R)-2-hydroxy-1-phenylethyl]-2-oxo-1,2-dihydro-3-pyridinecarboxamide, (11) N-[4-(4-amino-7-cyclopentyl-7H-pyrrolo[2,3-d]pyrimidin-5-yl)phenyl]-4-ethoxy-1-(4-fluorophenyl)-2-oxo-1,2-dihydro-3-pyridinecarboxamide, (12)N-[4-(4-amino-7-methyl-7H-pyrrolo[2,3-d]pyrimidin-5-yl)phenyl]-5-cyclopropyl-2-oxo-1-phenyl-1,2-dihydro-3-pyridinecarboxamide, (13)N-[4-(4-amino-7-methyl-7H-pyrrolo[2,3-d]pyrimidin-5-yl)phenyl]-7-(2-butynoyl)-2-oxo-1-phenyl-1,2,5,6,7,8-hexahydro-1,7-naphthyridine-3-carboxamide, (14) N-{4-[4-amino-7-methyl-6-(trifluoromethyl)-7H-pyrrolo[2,3-d]pyrimidin-5-yl]phenyl}-2,5-dioxo-1-phenyl-1,2,5,6,7,8-hexahydro-3-quinolinecarboxamide, a salt thereof, or an N-oxide thereof.

5. A pharmaceutical composition containing the compound represented by the general formula (I) as defined in claim 1, a salt thereof, or an N-oxide thereof.

6. A method for treating an Axl-related disease, or suppressing metastasis of tumor cells, the method including administering an effective amount of the compound represented by the general formula (I) as defined in claim 1, a salt thereof, or an N-oxide thereof to a mammal.

7. The method according to claim 6, wherein the cancer is acute myeloid leukemia, chronic myeloid leukemia, melanoma, breast cancer, pancreatic cancer, glioma, esophageal adenocarcinoma, large intestine cancer, renal cell carcinoma, thyroid cancer, non-small cell lung cancer, prostate cancer, stomach cancer, uveal malignant melanoma, ovarian cancer, endometrial cancer, or lymphoma.

* * * * *

UNITED STATES PATENT AND TRADEMARK OFFICE
CERTIFICATE OF CORRECTION

| | | |
|---|---|---|
| PATENT NO. | : 9,586,967 B2 | Page 1 of 1 |
| APPLICATION NO. | : 15/034905 | |
| DATED | : March 7, 2017 | |
| INVENTOR(S) | : Takayuki Inukai et al. | |

It is certified that error appears in the above-identified patent and that said Letters Patent is hereby corrected as shown below:

In the Claims

Column 104, Line 10, Claim 6, Line 1: Delete "an Axl related disease" and insert --a cancer--

Signed and Sealed this
Sixth Day of June, 2017

Michelle K. Lee
*Director of the United States Patent and Trademark Office*